(12) United States Patent
Sanghera et al.

(10) Patent No.: US 11,229,500 B2
(45) Date of Patent: Jan. 25, 2022

(54) DIRECTIONAL STIMULATION LEADS AND METHODS

(71) Applicant: AtaCor Medical, Inc., San Clemente, CA (US)

(72) Inventors: Rick Sanghera, San Clemente, CA (US); Alan Marcovecchio, San Clemente, CA (US); Sean P. McGeehan, Encinitas, CA (US)

(73) Assignee: ATACOR MEDICAL, INC., San Clemente, CA (US)

( * ) Notice: Subject to any disclaimer, the term of this patent is extended or adjusted under 35 U.S.C. 154(b) by 272 days.

(21) Appl. No.: 16/453,932

(22) Filed: Jun. 26, 2019

(65) Prior Publication Data

US 2019/0336241 A1    Nov. 7, 2019

Related U.S. Application Data

(63) Continuation of application No. 15/644,714, filed on Jul. 7, 2017, now Pat. No. 10,743,960, which is a
(Continued)

(51) Int. Cl.
*A61B 90/00* (2016.01)
*A61N 1/05* (2006.01)
(Continued)

(52) U.S. Cl.
CPC .............. *A61B 90/39* (2016.02); *A61B 90/02* (2016.02); *A61N 1/0504* (2013.01);
(Continued)

(58) Field of Classification Search
CPC ................ A61N 1/0587; A61N 1/3621; A61N 1/36521; A61N 1/36542; A61N 1/36557;
(Continued)

(56) References Cited

U.S. PATENT DOCUMENTS 3,416,534 A * 12/1968 Quinn .................. A61N 1/0587
607/131
3,485,247 A * 12/1969 Ackerman ........... A61N 1/0587
607/122
(Continued)

FOREIGN PATENT DOCUMENTS

EP          0668087        8/1995
EP          1530983 A2     5/2005
(Continued)

OTHER PUBLICATIONS

International Search Report and Written Opinion dated Sep. 21, 2020, International Application No. PCT/US2020/035268.
(Continued)

*Primary Examiner* — Carl H Layno
*Assistant Examiner* — Michael J Lau
(74) *Attorney, Agent, or Firm* — Pillsbury Winthrop Shaw Pittman LLP

(57) ABSTRACT

Systems, methods and devices for delivering stimulating energy with a lead having a directional electrode are disclosed. The lead includes a directional electrode having an electrically active portion configured to emanate stimulating energy from an exposed portion of the directional electrode. The lead also has an electrically insulating portion around at least part of the circumference of the lead. The electrically insulating portion is configured to insulate surrounding muscle and/or tissue from the stimulating energy when the lead is implanted in the patient.

18 Claims, 23 Drawing Sheets

Related U.S. Application Data continuation-in-part of application No. 14/846,578, filed on Sep. 4, 2015, now Pat. No. 11,051,847.

(60) Provisional application No. 62/360,110, filed on Jul. 8, 2016, provisional application No. 62/083,516, filed on Nov. 24, 2014, provisional application No. 62/146,569, filed on Apr. 13, 2015, provisional application No. 62/045,683, filed on Sep. 4, 2014.

(51) Int. Cl.
- *A61N 1/362* (2006.01)
- *A61N 1/365* (2006.01)
- *A61N 1/378* (2006.01)
- *A61N 1/372* (2006.01)
- *A61N 1/39* (2006.01)
- *A61N 1/375* (2006.01)

(52) U.S. Cl.
CPC ......... *A61N 1/0563* (2013.01); *A61N 1/0587* (2013.01); *A61N 1/362* (2013.01); *A61N 1/3621* (2013.01); *A61N 1/36521* (2013.01); *A61N 1/36542* (2013.01); *A61N 1/36557* (2013.01); *A61N 1/3787* (2013.01); *A61N 1/37217* (2013.01); *A61N 1/37264* (2013.01); *A61N 1/3956* (2013.01); *A61B 2090/3966* (2016.02); *A61B 2090/3983* (2016.02); *A61N 1/059* (2013.01); *A61N 1/3752* (2013.01)

(58) Field of Classification Search
CPC ............ A61N 1/37217; A61N 1/37264; A61N 1/3956; A61B 2090/3966; A61B 2090/3983
USPC ......................................................... 607/119
See application file for complete search history.

(56) References Cited

U.S. PATENT DOCUMENTS

| | | |
|---|---|---|
| 4,030,509 A | 6/1977 | Heilman |
| 4,146,037 A | 3/1979 | Flynn |
| 4,270,549 A | 6/1981 | Heilman |
| 4,280,510 A | 7/1981 | ONeill |
| 4,291,707 A | 9/1981 | Heilman |
| 4,306,560 A | 12/1981 | Harris |
| 4,437,475 A | 3/1984 | White |
| 4,512,351 A | 4/1985 | Pohndorf |
| 4,532,931 A | 8/1985 | Mills |
| 4,538,624 A | 9/1985 | Tarjan |
| 4,636,199 A | 1/1987 | Victor |
| 4,765,341 A | 8/1988 | Mower |
| 4,787,389 A | 11/1988 | Tarjan |
| 4,832,687 A | 5/1989 | Smith, III |
| 4,846,191 A | 7/1989 | Brockway |
| 4,865,037 A | 9/1989 | Chin |
| 5,036,854 A | 8/1991 | Schollmeyer |
| 5,125,904 A | 6/1992 | Lee |
| 5,129,394 A | 7/1992 | Mehra |
| 5,176,135 A | 1/1993 | Fain |
| 5,203,348 A | 4/1993 | Dahl |
| 5,255,691 A | 10/1993 | Otten |
| 5,255,692 A | 10/1993 | Neubauer |
| 5,273,053 A | 12/1993 | Pohndorf |
| 5,300,106 A | 4/1994 | Dahl |
| 5,312,355 A | 5/1994 | Lee |
| 5,336,252 A * | 8/1994 | Cohen ................. A61M 25/09 606/129 |
| 5,364,361 A | 11/1994 | Battenfield |
| 5,391,156 A | 2/1995 | Hildwein |
| 5,441,504 A | 8/1995 | Pohndorf |
| 5,456,699 A | 10/1995 | Armstrong |
| 5,476,493 A | 12/1995 | Muff |
| 5,509,924 A | 4/1996 | Paspa |
| 5,534,018 A | 7/1996 | Wahlstrand |
| 5,545,205 A | 8/1996 | Schulte |
| 5,562,677 A | 10/1996 | Hildwein |
| 5,571,215 A | 11/1996 | Sterman |
| 5,613,953 A | 3/1997 | Pohndorf |
| 5,690,648 A | 11/1997 | Fogarty |
| 5,716,392 A * | 2/1998 | Bourgeois ............ A61N 1/0502 600/372 |
| 5,728,151 A | 3/1998 | Garrison |
| 5,752,526 A | 5/1998 | Cosgrove |
| 5,776,110 A | 7/1998 | Guy |
| 5,814,076 A | 9/1998 | Brownlee |
| 5,823,946 A | 10/1998 | Chin |
| 5,830,214 A * | 11/1998 | Flom ..................... A61M 1/774 606/41 |
| 5,871,532 A | 2/1999 | Schroeppel |
| 5,895,414 A | 4/1999 | Sanchez-Zambrano |
| 5,904,711 A * | 5/1999 | Flom ..................... A61N 1/3904 607/129 |
| 5,941,819 A | 8/1999 | Chin |
| 5,944,732 A | 8/1999 | Raulerson |
| 5,951,518 A | 9/1999 | Licata |
| 6,024,704 A | 2/2000 | Meador |
| 6,032,079 A | 2/2000 | KenKnight |
| 6,099,547 A | 8/2000 | Gellman |
| 6,104,957 A | 8/2000 | Alo |
| 6,122,552 A | 9/2000 | Tockman |
| 6,159,198 A | 12/2000 | Gardeski |
| 6,228,052 B1 | 5/2001 | Pohndorf |
| 6,283,127 B1 | 9/2001 | Sterman |
| 6,324,414 B1 | 11/2001 | Gibbons |
| 6,415,187 B1 | 7/2002 | Kuzma |
| 6,445,954 B1 | 9/2002 | Olive |
| 6,478,028 B1 | 11/2002 | Paolitto |
| 6,544,247 B1 | 4/2003 | Gardeski |
| 6,651,672 B2 | 11/2003 | Roth |
| 6,706,052 B1 | 3/2004 | Chin |
| 6,718,203 B2 | 4/2004 | Weiner |
| 6,721,597 B1 | 4/2004 | Bardy |
| 6,730,083 B2 | 5/2004 | Freigang |
| 6,733,500 B2 | 5/2004 | Kelley |
| 6,749,574 B2 | 6/2004 | OKeefe |
| 6,770,070 B1 | 8/2004 | Balbierz |
| 6,772,014 B2 | 8/2004 | Coe |
| 6,836,687 B2 | 12/2004 | Kelley |
| 6,866,044 B2 | 3/2005 | Bardy |
| 6,868,291 B1 | 3/2005 | Bonner |
| 6,887,229 B1 | 5/2005 | Kurth |
| 6,890,295 B2 | 5/2005 | Michels |
| 6,918,908 B2 * | 7/2005 | Bonner .............. A61B 18/1485 606/41 |
| 6,999,819 B2 | 2/2006 | Swoyer |
| 7,033,326 B1 | 4/2006 | Pianca |
| 7,050,851 B2 | 5/2006 | Plombon |
| 7,069,083 B2 | 6/2006 | Finch |
| 7,096,064 B2 | 8/2006 | Deno |
| 7,117,039 B2 | 10/2006 | Manning |
| 7,120,496 B2 | 10/2006 | Bardy |
| 7,149,575 B2 | 12/2006 | Ostroff |
| 7,191,015 B2 | 3/2007 | Lamson |
| 7,195,637 B2 | 3/2007 | Mika |
| 7,218,970 B2 | 5/2007 | Ley |
| 7,229,450 B1 | 6/2007 | Chitre |
| 7,272,448 B1 | 9/2007 | Morgan |
| 7,288,096 B2 | 10/2007 | Chin |
| 7,316,667 B2 | 1/2008 | Lindstrom |
| 7,319,905 B1 | 1/2008 | Morgan |
| 7,322,960 B2 | 1/2008 | Yamamoto |
| 7,353,067 B1 * | 4/2008 | Helland ................ A61N 1/0558 607/130 |
| 7,369,899 B2 | 5/2008 | Malinowski |
| 7,373,207 B2 * | 5/2008 | Lattouf .............. A61B 17/0401 607/130 |
| 7,389,134 B1 | 6/2008 | Karicherla |
| 7,398,781 B1 | 7/2008 | Chin |
| 7,450,997 B1 | 11/2008 | Pianca |
| 7,496,408 B2 * | 2/2009 | Ghanem ................. A61N 1/05 607/115 |
| 7,499,758 B2 | 3/2009 | Cates |

(56) References Cited

U.S. PATENT DOCUMENTS

| | | |
|---|---|---|
| 7,515,969 B2 | 4/2009 | Tockman |
| 7,539,542 B1 | 5/2009 | Malinowski |
| 7,627,375 B2 | 12/2009 | Bardy |
| 7,655,014 B2 | 2/2010 | Ko |
| 7,736,330 B2 | 6/2010 | Bardy |
| 7,751,885 B2 | 7/2010 | Bardy |
| 7,761,150 B2 | 7/2010 | Ghanem |
| 7,765,014 B2 | 7/2010 | Eversull |
| 7,801,622 B2 | 9/2010 | Camps |
| 7,837,671 B2 | 11/2010 | Eversull |
| 7,846,088 B2 | 12/2010 | Ness |
| 7,850,610 B2 | 12/2010 | Ferek-Petric |
| 7,890,191 B2 | 2/2011 | Rutten |
| 7,908,015 B2 | 3/2011 | Lazeroms |
| 7,930,028 B2 | 4/2011 | Lang |
| 7,930,040 B1 | 4/2011 | Kelsch |
| 7,967,833 B2 | 6/2011 | Sterman |
| 7,983,765 B1 | 7/2011 | Doan |
| 8,060,207 B2 | 11/2011 | Wallace |
| 8,065,020 B2 | 11/2011 | Ley |
| 8,066,702 B2 | 11/2011 | Rittman, III |
| 8,090,451 B2 | 1/2012 | Tyson, Jr. |
| 8,155,755 B2 | 4/2012 | Flynn |
| 8,157,813 B2 | 4/2012 | Ko |
| 8,260,436 B2 | 9/2012 | Gerber |
| 8,280,527 B2 | 10/2012 | Eckerdal |
| 8,332,036 B2 | 12/2012 | Hastings |
| 8,340,779 B2 | 12/2012 | Harris |
| 8,355,786 B2 | 1/2013 | Malinowski |
| 8,386,052 B2 | 2/2013 | Harris |
| 8,394,079 B2 | 3/2013 | Drake |
| 8,435,208 B2 | 5/2013 | Bardy |
| 8,442,620 B2 | 5/2013 | Silipo |
| 8,452,421 B2 | 5/2013 | Thenuwara |
| 8,457,742 B2 | 6/2013 | Jacobson |
| 8,478,424 B2 | 7/2013 | Tronnes |
| 8,478,426 B2 | 7/2013 | Barker |
| 8,478,431 B2 | 7/2013 | Griswold |
| 8,532,789 B2 | 9/2013 | Smits |
| 8,594,809 B2 | 11/2013 | Yang |
| 8,886,311 B2 | 11/2014 | Anderson |
| 9,622,778 B2 | 4/2017 | Wengreen |
| 9,636,505 B2 | 5/2017 | Sanghera |
| 9,707,389 B2 | 7/2017 | McGeehan |
| 10,130,824 B2 | 11/2018 | Grinberg |
| 10,137,295 B2 | 11/2018 | Marshall |
| 10,471,267 B2 | 11/2019 | Thompson-Nauman |
| 2002/0035381 A1* | 3/2002 | Bardy .............. A61N 1/375 607/4 |
| 2002/0035388 A1 | 3/2002 | Lindemans |
| 2002/0042629 A1* | 4/2002 | Bardy .............. A61N 1/3968 607/5 |
| 2002/0120294 A1 | 8/2002 | Kroll |
| 2003/0045904 A1 | 3/2003 | Bardy |
| 2003/0074041 A1* | 4/2003 | Parry .............. A61N 1/0587 607/130 |
| 2003/0088278 A1 | 5/2003 | Bardy |
| 2003/0097153 A1* | 5/2003 | Bardy .............. A61N 1/3931 607/5 |
| 2003/0114905 A1 | 6/2003 | Kuzma |
| 2003/0114906 A1* | 6/2003 | Booker, III ........ A61N 1/0587 607/122 |
| 2003/0114908 A1 | 6/2003 | Flach |
| 2003/0120264 A1 | 6/2003 | Lattouf |
| 2003/0130581 A1 | 7/2003 | Salo |
| 2003/0187458 A1 | 10/2003 | Carlson |
| 2004/0059348 A1 | 3/2004 | Geske |
| 2004/0088035 A1 | 5/2004 | W Guenst |
| 2004/0102829 A1 | 5/2004 | Bonner |
| 2004/0143284 A1* | 7/2004 | Chin .............. A61B 17/3468 606/192 |
| 2004/0158185 A1 | 8/2004 | Moran |
| 2004/0210293 A1 | 10/2004 | Bardy |
| 2004/0215240 A1 | 10/2004 | Lovett |
| 2004/0230282 A1 | 11/2004 | Cates |
| 2004/0236396 A1 | 11/2004 | Coe |
| 2005/0027328 A1 | 2/2005 | Greenstein |
| 2005/0049663 A1 | 3/2005 | Harris |
| 2005/0131505 A1 | 6/2005 | Yokoyama |
| 2005/0165324 A1 | 7/2005 | Receveur |
| 2005/0192639 A1 | 9/2005 | Bardy |
| 2005/0288731 A1 | 12/2005 | Shames |
| 2005/0288758 A1 | 12/2005 | Jones |
| 2006/0041295 A1 | 2/2006 | Osypka |
| 2006/0047333 A1* | 3/2006 | Tockman .............. A61N 1/0587 607/127 |
| 2006/0085039 A1* | 4/2006 | Hastings ................ A61N 1/365 607/9 |
| 2006/0089699 A1 | 4/2006 | Imran |
| 2006/0116746 A1* | 6/2006 | Chin .................... A61N 1/0587 607/119 |
| 2006/0122676 A1 | 6/2006 | Ko |
| 2006/0129202 A1 | 6/2006 | Armstrong |
| 2006/0136004 A1 | 6/2006 | Cowan |
| 2006/0161205 A1* | 7/2006 | Mitrani .................... A61N 1/05 607/4 |
| 2006/0241711 A1 | 10/2006 | Sathaye |
| 2006/0247672 A1* | 11/2006 | Vidlund ............ A61B 17/3421 606/190 |
| 2006/0247753 A1 | 11/2006 | Wenger |
| 2006/0253181 A1 | 11/2006 | Schulman |
| 2006/0266368 A1 | 11/2006 | Heintz |
| 2007/0023947 A1 | 2/2007 | Ludwig |
| 2007/0088394 A1 | 4/2007 | Jacobson |
| 2007/0100409 A1 | 5/2007 | Worley |
| 2007/0150015 A1 | 6/2007 | Zhang |
| 2007/0150023 A1 | 6/2007 | Ignagni |
| 2007/0179388 A1 | 8/2007 | Larik |
| 2007/0208402 A1 | 9/2007 | Helland |
| 2007/0249992 A1 | 10/2007 | Bardy |
| 2008/0021505 A1* | 1/2008 | Hastings ............ A61N 1/37518 607/9 |
| 2008/0027488 A1* | 1/2008 | Coles .................... A61N 1/056 607/9 |
| 2008/0039866 A1 | 2/2008 | Stetz |
| 2008/0046056 A1* | 2/2008 | O'Connor ............ A61N 1/0587 607/119 |
| 2008/0103575 A1 | 5/2008 | Gerber |
| 2008/0183230 A1* | 7/2008 | Kemmetmueller .. A61N 1/3931 607/5 |
| 2008/0243196 A1 | 10/2008 | Libbus |
| 2008/0243219 A1 | 10/2008 | Malinowski |
| 2008/0269716 A1 | 10/2008 | Bonde |
| 2008/0294217 A1 | 11/2008 | Lian |
| 2008/0300644 A1 | 12/2008 | Sathaye |
| 2009/0054947 A1 | 2/2009 | Bourn |
| 2009/0069803 A1 | 3/2009 | Starkebaum |
| 2009/0157091 A1 | 6/2009 | Buysman |
| 2009/0209970 A1 | 8/2009 | Tanaka |
| 2009/0222021 A1 | 9/2009 | Chang |
| 2009/0259283 A1 | 10/2009 | Brandt |
| 2009/0264780 A1 | 10/2009 | Schilling |
| 2009/0270962 A1 | 10/2009 | Yang |
| 2009/0326346 A1 | 12/2009 | Kracker |
| 2010/0016935 A1 | 1/2010 | Strandberg |
| 2010/0030227 A1 | 2/2010 | Kast |
| 2010/0030228 A1 | 2/2010 | Havel |
| 2010/0056858 A1 | 3/2010 | Mokelke |
| 2010/0082087 A1 | 4/2010 | Silipo |
| 2010/0094252 A1 | 4/2010 | Wengreen |
| 2010/0113963 A1 | 5/2010 | Smits |
| 2010/0125194 A1 | 5/2010 | Bonner |
| 2010/0137879 A1 | 6/2010 | Ko |
| 2010/0152747 A1 | 6/2010 | Padiy |
| 2010/0152798 A1 | 6/2010 | Sanghera |
| 2010/0185268 A1 | 7/2010 | Fowler |
| 2010/0211064 A1 | 8/2010 | Mahapatra |
| 2010/0217298 A1 | 8/2010 | Bardy |
| 2010/0217301 A1 | 8/2010 | Bardy |
| 2010/0241189 A1 | 9/2010 | Dobak |
| 2010/0305428 A1 | 12/2010 | Bonner |
| 2010/0318098 A1 | 12/2010 | Lund |

(56) References Cited

U.S. PATENT DOCUMENTS

| | | | |
|---|---|---|---|
| 2010/0324579 A1 | 12/2010 | Bardy | |
| 2011/0009933 A1 | 1/2011 | Barker | |
| 2011/0024491 A1 | 2/2011 | Jamali | |
| 2011/0066185 A1 | 3/2011 | Wotton, III | |
| 2011/0077708 A1 | 3/2011 | Ostroff | |
| 2011/0125163 A1 | 5/2011 | Rutten | |
| 2011/0152706 A1* | 6/2011 | Christopherson | A61B 5/01 600/529 |
| 2011/0178566 A1 | 7/2011 | Stahmann | |
| 2011/0210156 A1 | 9/2011 | Smith | |
| 2011/0224680 A1 | 9/2011 | Barker | |
| 2011/0224681 A1 | 9/2011 | McDonald | |
| 2011/0230906 A1 | 9/2011 | Modesitt | |
| 2011/0257660 A1 | 10/2011 | Jones | |
| 2012/0016377 A1 | 1/2012 | Geroy | |
| 2012/0029335 A1* | 2/2012 | Sudam | A61N 1/05 600/374 |
| 2012/0037291 A1 | 2/2012 | Goolishian | |
| 2012/0078266 A1 | 3/2012 | Tyson | |
| 2012/0089153 A1 | 4/2012 | Christopherson | |
| 2012/0097174 A1 | 4/2012 | Spotnitz | |
| 2012/0109250 A1 | 5/2012 | Cates | |
| 2012/0123496 A1 | 5/2012 | Schotzko | |
| 2012/0191106 A1 | 7/2012 | Ko | |
| 2012/0209283 A1 | 8/2012 | Zhu | |
| 2012/0209298 A1 | 8/2012 | McClurg | |
| 2012/0302863 A1* | 11/2012 | O'Neill | A61B 90/39 600/407 |
| 2013/0006326 A1 | 1/2013 | Ackermann | |
| 2013/0041345 A1 | 2/2013 | Kilcoin | |
| 2013/0103049 A1 | 4/2013 | Bonde | |
| 2013/0158564 A1 | 6/2013 | Harris | |
| 2013/0178711 A1 | 7/2013 | Avneri | |
| 2013/0226266 A1 | 8/2013 | Murtonen | |
| 2013/0237781 A1 | 9/2013 | Gyrn | |
| 2013/0238067 A1 | 9/2013 | Baudino | |
| 2013/0296880 A1 | 11/2013 | Kelley | |
| 2013/0338707 A1 | 12/2013 | Killion | |
| 2014/0005755 A1 | 1/2014 | Wolf, II | |
| 2014/0018872 A1 | 1/2014 | Siejko | |
| 2014/0180273 A1 | 6/2014 | Nair | |
| 2014/0257421 A1 | 9/2014 | Sanghera | |
| 2014/0330208 A1 | 11/2014 | Christie | |
| 2014/0330248 A1 | 11/2014 | Thompson-Nauman | |
| 2014/0330287 A1 | 11/2014 | Thompson-Nauman | |
| 2014/0330325 A1 | 11/2014 | Thompson-Nauman | |
| 2014/0330326 A1 | 11/2014 | Thompson-Nauman | |
| 2014/0330327 A1 | 11/2014 | Thompson-Nauman | |
| 2014/0330328 A1 | 11/2014 | Christie | |
| 2014/0330329 A1 | 11/2014 | Thompson-Nauman | |
| 2014/0330331 A1 | 11/2014 | Thompson-Nauman | |
| 2015/0013689 A1 | 1/2015 | Shackelford | |
| 2015/0051612 A1 | 2/2015 | Schmidt | |
| 2015/0051615 A1 | 2/2015 | Schmidt | |
| 2015/0088155 A1 | 3/2015 | Stahmann | |
| 2015/0133954 A1 | 5/2015 | Seifert | |
| 2015/0142069 A1 | 5/2015 | Sambelashvili | |
| 2015/0157497 A1 | 6/2015 | Hufford | |
| 2015/0223906 A1 | 8/2015 | O'Neill | |
| 2015/0313633 A1 | 11/2015 | Gross | |
| 2015/0328473 A1 | 11/2015 | Bodner | |
| 2016/0051159 A1 | 2/2016 | Mazaeva | |
| 2016/0067478 A1 | 3/2016 | McGeehan | |
| 2016/0067479 A1 | 3/2016 | Marcovecchio | |
| 2016/0067480 A1 | 3/2016 | Sanghera | |
| 2016/0067488 A1 | 3/2016 | Sanghera | |
| 2016/0144192 A1 | 5/2016 | Sanghera | |
| 2016/0175581 A1 | 6/2016 | Gordon | |
| 2016/0184047 A1 | 6/2016 | Weir | |
| 2017/0224995 A1 | 8/2017 | Sanghera | |
| 2017/0304019 A1 | 10/2017 | Sanghera | |
| 2017/0304634 A1 | 10/2017 | Sanghera | |
| 2018/0021572 A1 | 1/2018 | McGeehan | |
| 2018/0050199 A1 | 2/2018 | Sanghera | |

FOREIGN PATENT DOCUMENTS

| | | |
|---|---|---|
| EP | 2346419 | 7/2011 |
| EP | 2967644 | 1/2016 |
| EP | 2994193 | 3/2016 |
| EP | 3173043 | 5/2017 |
| WO | 2002026315 A1 | 4/2002 |
| WO | 2006115772 A2 | 11/2006 |
| WO | 2013163267 A1 | 10/2013 |
| WO | 2015143327 | 9/2015 |

OTHER PUBLICATIONS

Brown, Charles G., et. al. 'Injuries Associated with Percutaneous Placement of Transthoracic Pacemakers.' Annals of Emergency Medicine 14.3 (1985): 223-28.

Brown, Charles G., et. al. 'Placement Accuracy of Percutaneous Transthoracic Pacemakers.' The American Journal of Emergency Medicine 3.3 (1985): 193-98.

Nagdev, Arun, and Daniel Mantuani. 'A Novel In-plane Technique for Ultrasound-guided Pericardiocentesis.' Tlie American Journal of Emergency Medicine 31.9 (2013): 1424.e5-1424.e9.

Pai, N. V., et. al. 'Relation of Internal Thoracic Artery to Lateral Sternal Border and Its Significance in Clinical Procedures.' International Journal of Biological & Medical Research 4.4 (2013): 3633-636.

PCT/US2017/041265; International Search Report and Written Opinion dated Sep. 25, 2017.

* cited by examiner

700

702 — Determining, using one or more sensors, the location of blood-filled structures in the vicinity of an intercostal space associated with a cardiac notch of the left lung of a patient.

704 — Choosing a region for advancing of a lead through intercostal muscles associated with the cardiac notch of the patient, the region chosen based on the determined location of blood-filled structures, the lead configured to couple with a pulse generator for sensing intrinsic cardiac activity and for generating therapeutic electrical pulses for treating heart conditions in a patient.

706 — Advancing a lead through the intercostal muscles associated with the cardiac notch of the patient.

708 — Ceasing advancement of the lead in response to an indication, from one or more sensors, that the distal end of the lead is at the desired location.

FIG. 7

DIRECTIONAL STIMULATION LEADS AND METHODS

CROSS-REFERENCE TO RELATED APPLICATIONS

This application is a continuation of and claims priority to and benefit of U.S. patent application Ser. No. 15/644,714, now U.S. Pat. No. 10,743,960, filed Jul. 7, 2017, which claims priority to and benefit of U.S. Provisional Patent Application 62/360,110, filed Jul. 8, 2016, and is also a continuation in part of U.S. patent application Ser. No. 14/846,578, now U.S. Pat. No. 11,051,847, filed Sep. 4, 2015, which claims priority to and the benefit of U.S. Provisional Patent Application 62/083,516, filed Nov. 24, 2014, U.S. Provisional Patent Application 62/146,569, filed Apr. 13, 2015, and U.S. Provisional Application 62/045,683, filed Sep. 4, 2014, the disclosures of which are incorporated herein by reference in their entirety.

BACKGROUND

An artificial pacemaker is a medical device that helps control abnormal heart rhythms. A pacemaker uses electrical pulses to prompt the heart to beat at a normal rate. The pacemaker may speed up a slow heart rhythm, control a fast heart rhythm, and coordinate the chambers of the heart. The implantable portions of a pacemaker system generally comprise three main components: a pulse generator, one or more wires called leads, and electrodes found on each lead. The pulse generator produces the electrical signals that make the heart beat. Most pulse generators also have the capability to receive and respond to signals that are sent by the heart. Leads are insulated flexible wires that conduct electrical signals to the heart from the pulse generator. The leads may also relay signals from the heart to the pulse generator. One end of the lead is attached to the pulse generator and the electrode end of the lead is positioned on or in the heart.

SUMMARY

Methods and apparatuses for use in medical procedures are disclosed. Some implementations may include a medical procedure guide that can overlay portions of anatomy of a patient, where the guide may include alignment markings to facilitate proper placement, procedure markings to facilitate determination of a position at which to commence a medical procedure, and/or imaging markers incorporated within the guide to facilitate commencement or completion of the medical procedure in conjunction with imaging.

In some variations, the guide may include critical anatomy markings, or may be flexible to at least partially form to the anatomy of a patient. The guide may be affixed to the patient, for example, with an adhesive, and may be designed to allow for puncture or incision through the guide during a medical procedure.

In other implementations, imaging markers may facilitate determination of the position to commence a medical procedure, to facilitate determination of the presence or absence of interposed lung, or to facilitate the determination of a distance between a sternal margin and a thoracic vain or thoracic artery.

In some implementations imaging markers may be located at particular known depths within the guide to facilitate completion of the medical procedure. The imaging markers may be radiopaque.

In one implementation, the medical procedure may involve insertion of a cardiac therapy lead for pacing or defibrillation and the guide's alignment markings may be configured to line up with at least a portion of the patient's sternum and at least one rib. The procedure markings may also be configured to locate a position proximate the patient's sternum, in the region of a cardiac notch. The imaging markers may also facilitate determination of a proper depth of insertion for the cardiac therapy lead. In some implementations, the guide may also facilitate a determination of the distance between a posterior surface of a sternum and a pericardium and/or facilitate a determination of the patient's sternum thickness.

Methods for inserting a lead for cardiac therapy into an intercostal space associated with the cardiac notch of a patient and proximate to a lateral margin of the patient's sternum are also disclosed, including advancing the distal end of the lead through the intercostal space.

In some implementations, the method includes palpating the lateral margin of the sternum and puncturing the tissue of the patient to facilitate entry into the intercostal space.

In other implementations, the method may include making an incision above the patient's sternum and pressing a distal end of a lead delivery system against the patient's sternum and sliding the distal end of the lead delivery system on the patient's sternum until reaching the lateral margin of the patient's sternum. The method may further include inserting a pulse generator into the incision above the patient's sternum.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 7 is an illustration of an exemplary process flow illustrating a method of placing a pacing lead having features consistent with the current subject matter;

When practical, similar reference numbers denote similar structures, features, or elements.

DETAILED DESCRIPTION

Implantable medical devices (IMDs), such as cardiac pacemakers or implantable cardioverter defibrillators (ICDs), provide therapeutic electrical stimulation to the heart of a patient. This electrical stimulation may be delivered via electrodes on one or more implantable endocardial or epicardial leads that are positioned in or on the heart. This electrical stimulation may also be delivered using a leadless cardiac pacemaker disposed within a chamber of the heart. Therapeutic electrical stimulation may be delivered to the heart in the form of electrical pulses or shocks for pacing, cardioversion or defibrillation.

An implantable cardiac pacemaker may be configured to facilitate the treatment of cardiac arrhythmias. The devices, systems and methods of the present disclosure may be used to treat cardiac arrhythmias including, but not limited to, bradycardia, tachycardia, atrial flutter and atrial fibrillation. Resynchronization pacing therapy may also be provided. While embodiments of the present disclosure refer to a cardiac pacing system, is understood that the implantable medical device may additionally be an implantable defibrillator used to treat disruptive cardiac arrhythmias.

A cardiac pacemaker consistent with the present disclosure may include a pulse generator implanted adjacent the rib cage of the patient, for example, on the ribcage under the pectoral muscles, laterally on the ribcage, within the mediastinum, subcutaneously on the sternum of the ribcage, and the like. One or more leads may be connected to the pulse generator. A lead may be inserted, for example, between two ribs of a patient so that the distal end of the lead is positioned within the mediastinum of the patient adjacent, but not touching, the heart. The distal end of the lead may include an electrode for providing electrical pulse therapy to the patient's heart and may also include at least one sensor for detecting a state of the patient's organs and/or systems. The cardiac pacemaker may include a unitary design where the components of the pulse generator and lead are incorporated within a single form factor. For example, where a first portion of the unitary device resides within the subcutaneous tissue and a second portion of the unitary device is placed through an intercostal space into a location within the mediastinum.

Figure 1:
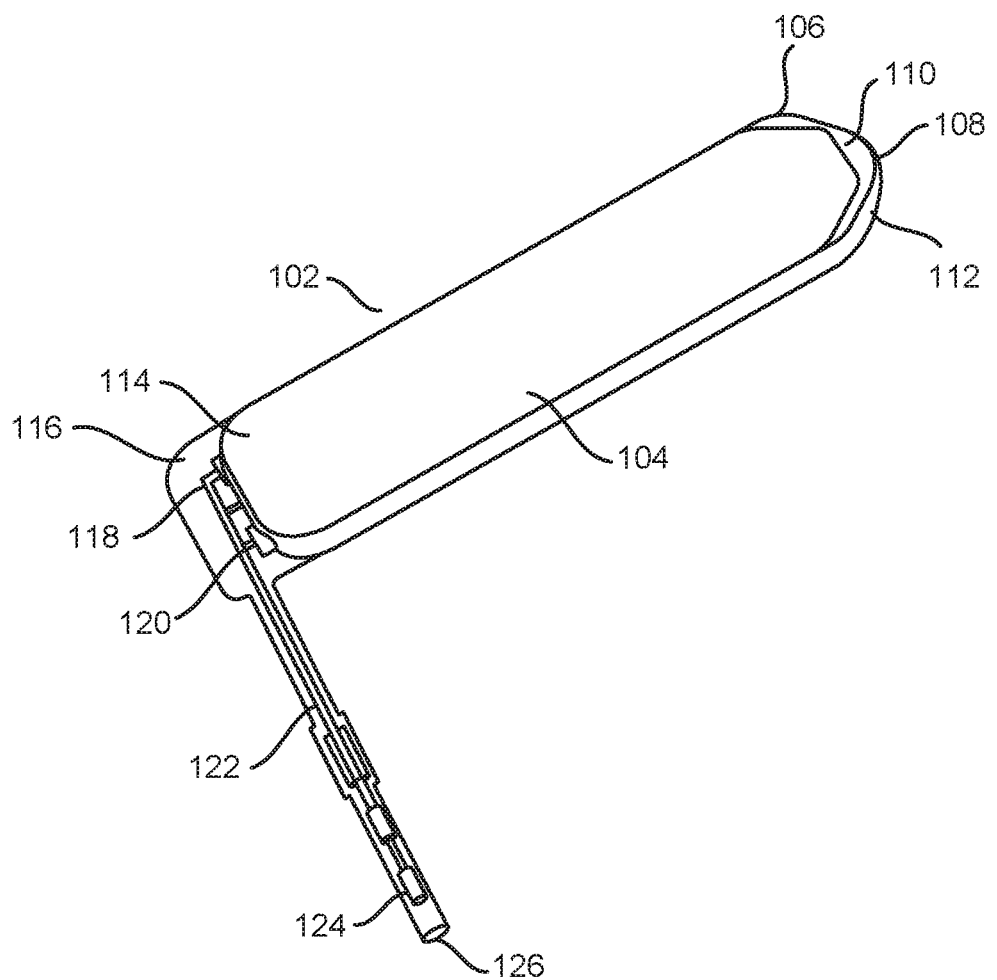
FIG. 1 is a front-view of an exemplary pulse generator having features consistent with implementations of the current subject matter.

FIG. 1 is a front-view 100 of a pulse generator 102 having features consistent with implementations of the current subject matter. The pulse generator 102 may be referred to as a cardiac pacemaker. The pulse generator 102 can include a housing 104, which may be hermetically sealed. In the present disclosure, and commonly in the art, housing 104 and everything within it may be referred to as a pulse generator, despite there being elements inside the housing other than those that generate pulses (for example, processors, storage, battery, etc.).

Housing 104 can be substantially rectangular in shape and the first end of the housing 104 may include a tapered portion 108. The tapered portion can include a first tapered edge 110, tapered inwardly toward the transverse plane. The tapered portion 108 can include a second tapered edge 112 tapered inwardly toward the longitudinal plane. Each of the first tapered edge 110 and the second tapered edge 112 may have a similar tapered edge generally symmetrically disposed on the opposite side of tapered portion 108, to form two pairs of tapered edges. The pairs of tapered edges may thereby form a chisel-shape at the first end 106 of pulse generator 102. When used in the present disclosure, the term "chisel-shape" refers to any configuration of a portion of housing 104 that facilitates the separation of tissue planes during placement of pulse generator 102 into a patient. The "chisel-shape" can facilitate creation of a tightly fitting and properly sized pocket in the patient's tissue in which the pulse generator may be secured. For example, a chisel-shape portion of housing 104 may have a single tapered edge, a pair of tapered edges, 2 pairs of tapered edges, and the like. Generally, the tapering of the edges forms the shape of a chisel or the shape of the head of a flat head screwdriver. In some variations, the second end 114 of the pulse generator can be tapered. In other variations, one or more additional sides of the pulse generator 102 can be tapered.

Housing 104 of pulse generator 102 can include a second end 114. The second end 114 can include a port assembly 116. Port assembly 116 can be integrated with housing 104 to form a hermetically sealed structure. Port assembly 116 may be configured to facilitate the egress of conductors from housing 104 of pulse generator 102 while maintaining a seal. For example, port assembly 116 may be configured to facilitate the egress of a first conductor 118 and a second conductor 120 from housing 104. The first conductor 118 and the second conductor 120 may combine within port assembly 116 to form a twin-lead cable 122. In some variations, the twin-lead cable 122 can be a coaxial cable. The twin-lead cable 122 may include a connection port 124 remote from housing 104. Connection port 124 can be configured to receive at least one lead, for example, a pacing lead. Connection port 124 of the cable 122 can include a sealed housing 126. Sealed housing 126 can be configured to envelope a portion of the received lead(s) and form a sealed connection with the received lead(s).

Port assembly 116 may be made from a different material than housing 104. For example, housing 104 may be made from a metal alloy and port assembly 116 may be made from a more flexible polymer. While port assembly 116 may be manufactured separately from housing 104 and then integrated with it, port assembly 116 may also be designed to be part of housing 104 itself. The port assembly 116 may be externalized from the housing 104 as depicted in FIG. 1. The port assembly 116 may be incorporated within the shape of housing 104 of pulse generator 102.

Figure 2:
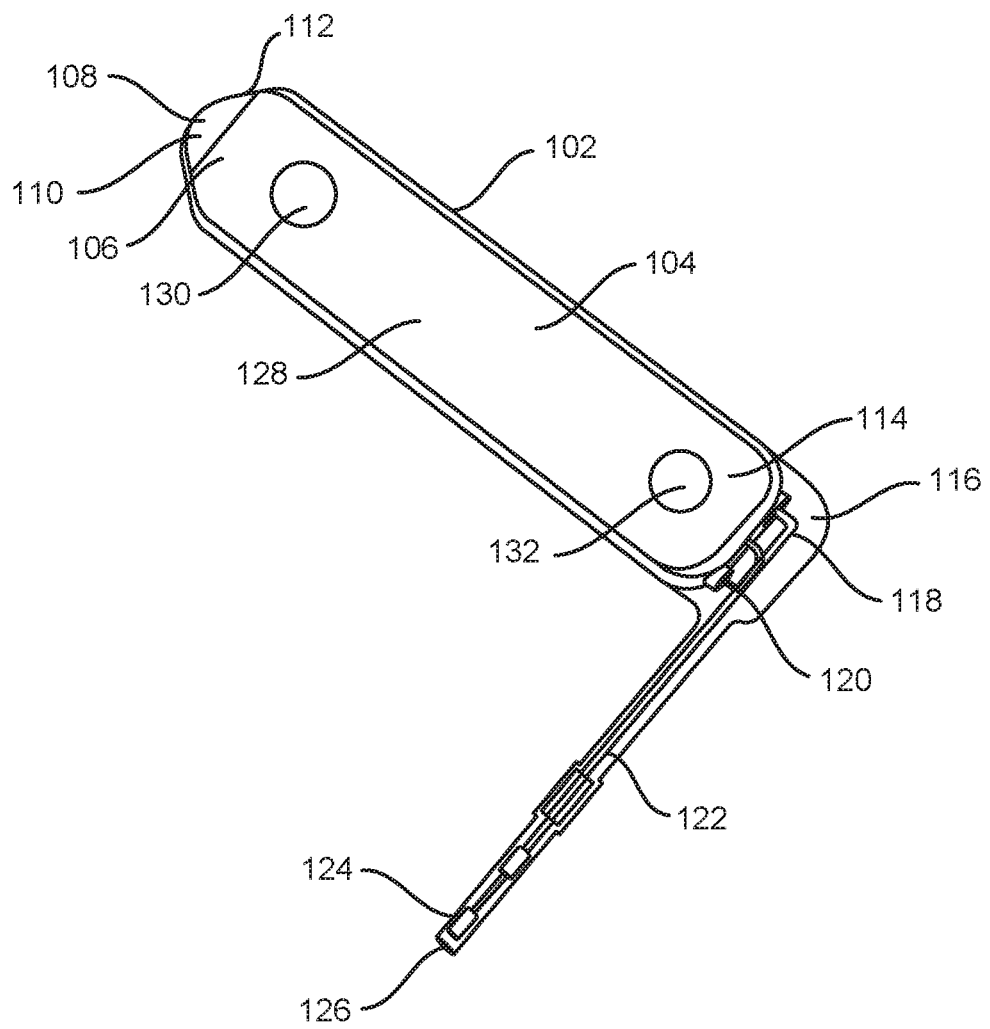
FIG. 2 is a rear-view of an exemplary pulse generator having features consistent with implementations of the current subject matter.

FIG. 2 is a rear-view 200 of pulse generator 102 showing the back-side 128 of housing 104. As shown, pulse generator 102 can include one or more electrodes or sensors disposed within housing 104. As depicted in the example of FIG. 2, housing 104 includes a first in-housing electrode 130 and a second in-housing electrode 132. The various electrodes illustrated and discussed herein may be used for delivering therapy to the patient, sensing a condition of the patient, and/or a combination thereof. A pulse generator consistent with the present disclosure installed at or near the sternum of a patient can monitor the heart, lungs, major blood vessels, and the like through sensor(s) integrated into housing 104.

Figure 3:
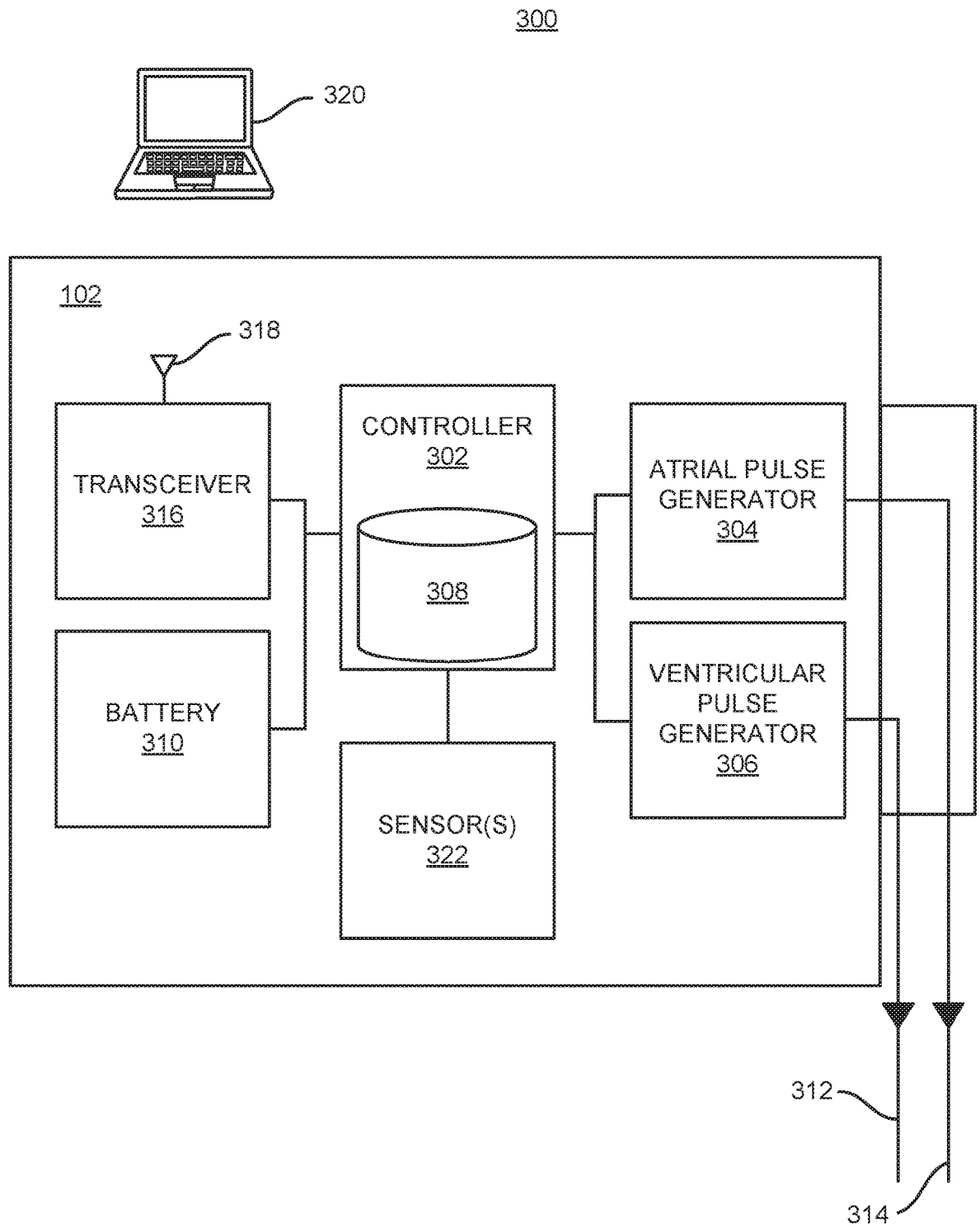
FIG. 3 is an illustration of a simplified schematic diagram of an exemplary pulse generator having features consistent with implementations of the current subject matter.

FIG. 3 is an illustration 300 of a simplified schematic diagram of an exemplary pulse generator 102 having features consistent with the current subject matter. Pulse generator 102 can include signal processing and therapy circuitry to detect various cardiac conditions. Cardiac conditions can include ventricular dyssynchrony, arrhythmias such as bradycardia and tachycardia conditions, and the like. Pulse generator 102 can be configured to sense and discriminate atrial and ventricular activity and then deliver appropriate electrical stimuli to the heart based on a sensed state of the heart.

Pulse generator 102 can include one or more components. The one or more components may be hermetically sealed within the housing 104 of pulse generator 102. Pulse generator 102 can include a controller 302, configured to control the operation of the pulse generator 102. The pulse generator 102 can include an atrial pulse generator 304 and may also include a ventricular pulse generator 306. Controller 302 can be configured to cause the atrial pulse generator 304 and the ventricular pulse generator 306 to generate electrical pulses in accordance with one or more protocols that may be loaded onto controller 302. Controller 302 can be configured to control pulse generators 304, 306, to deliver electrical pulses with the amplitudes, pulse widths, frequency, or electrode polarities specified by the therapy protocols, to one or more atria or ventricles.

Controller electronic storage 308 can store instructions configured to be implemented by the controller to control the functions of pulse generator 102.

Controller 302 can include a processor(s). The processor(s) can include any one or more of a microprocessor, a controller, a digital signal processor (DSP), an application specific integrated circuit (ASIC), a field-programmable gate array (FPGA), or equivalent discrete or analog logic circuitry. The functions attributed to controller 302 herein may be embodied as software, firmware, hardware or any combination thereof.

The pulse generator 102 can include a battery 310 to power the components of the pulse generator 102. In some variations, battery 310 can be configured to charge a capacitor. Atrial pulse generator 304 and ventricular pulse generator 306 can include a capacitor charged by the battery 310. The electrical energy stored in the capacitor(s) can be discharged as controlled by controller 302. The electrical energy can be transmitted to its destination through one or more electrode leads 312, 314. The leads can include a ventricular pulsing lead 312, an atrial pulsing lead 314, and/or other leads.

Pulse generator 102 can include one or more sensors 322. Sensor(s) 322 can be configured to monitor various aspects of a patient's physiology. Sensor(s) 322 may be embedded in the housing of pulse generator 102, incorporated into leads 312, 314 or be incorporated into separate leads. Sensors 322 of pulse generator 102 can be configured to detect, for example, signals from a patient's heart. The signals can be decoded by controller 302 of the pulse generator to determine a state of the patient. In response to detecting a cardiac arrhythmia, controller 302 can be configured to cause appropriate electrical stimulation to be transmitted through electrodes 312 and 314 by atrial pulse generator 304 and/or ventricular pulse generator 306.

Sensor(s) 322 can be further configured to detect other physiological states of the patient, for example, a respiration rate, blood oximetry, and/or other physiological states. In variations where the pulse generator 102 utilizes a plurality of electrodes, controller 302 may be configured to alter the sensing and delivery vectors between available electrodes to enhance the sensitivity and specificity of arrhythmia detection and improve efficacy of the therapy delivered by the electrical impulses from the pulse generator 102.

Pulse generator 102 can include a transceiver 316. The transceiver can include an antenna 318. The transceiver 316 can be configured to transmit and/or receive radio frequency signals. The transceiver 316 can be configured to transmit and/or receive wireless signals having any wireless communication protocol. Wireless communication protocols can include Bluetooth, Bluetooth low energy, Near-Field Communication, WiFi, and/or other radio frequency protocols. The transceiver 316 can be configured to transmit and/or receive radio frequency signals to and/or from a programmer 320. The programmer 320 can be a computing device external to the patient. Programmer 320 may comprise a transceiver configured to transmit and/or receive radio frequency signals to and/or from the transceiver 316 of the pulse generator 102. Transceiver 316 can be configured to wirelessly communicate with programmer 320 through induction, radio-frequency communication or other short-range communication methodologies.

In some variations, programmer 320 can be configured to communicate with the pulse generator 102 through longer-range remote connectivity systems. Such longer-range remote connectivity systems can facilitate remote access, by an operator, to pulse generator 102 without the operator being in close proximity with the patient. Longer-range remote connectivity systems can include, for example, remote connectivity through the Internet, and the like. When an operator connects with pulse generator 102 through longer-range remote connectivity systems, a local device can be positioned within a threshold distance of the patient. The local device can communicate using one or more radio-frequency wireless connections with the pulse generator 102. The local device can, in turn, include hardware and/or software features configured to facilitate communication between it and an operator device at which the operator is stationed. The local device can be, for example, a mobile computing device such as a smartphone, tablet, laptop, and the like. The local device can be a purpose-built local device configured to communicate with the pulse generator 102. The local device can be paired with the pulse generator 102 such that the communications between the pulse generator 102 and the local device are encrypted. Communications between the local device and the operator device can be encrypted.

Programmer 320 can be configured to program one or more parameters of the pulse generator 102. The parameter(s) can include timing of the stimulation pulses of the atrial pulse generator, timing of the stimulation pulses of the ventricular pulse generator, timing of pulses relative to certain sensed activity of the anatomy of the patient, the energy levels of the stimulation pulses, the duration of the stimulation pulses, the pattern of the stimulation pulses and other parameters. The programmer 320 can facilitate the performance of diagnostics on the patient or the pulse generator 102.

Programmer 320 can be configured to facilitate an operator of the programmer 320 to define how the pulse generator 102 senses electrical signals, for example ECGs, and the like. The programmer 320 can facilitate an operator of the programmer 320 to define how the pulse generator 102 detects cardiac conditions, for example ventricular dyssynchrony, arrhythmias, and the like. The programmer 320 can facilitate defining how the pulse generator 102 delivers therapy, and communicates with other devices.

An operator can fine-tune parameters through the programmer 320. For example, the sensitivity of sensors embodied in the housing of the pulse generator 302, or within leads, can be modified. Programmer 320 can facilitate setting up communication protocols between the pulse generator 102 and another device such as a mobile computing device. Programmer 320 can be configured to facilitate modification of the communication protocols of the pulse generator 102, such as adding security layers, or preventing two-way communication. Programmer 320 can be configured to facilitate determination of which combination of implanted electrodes are best suited for sensing and therapy delivery.

Programmer 320 can be used during the implant procedure. For example, programmer 320 can be used to determine if an implanted lead is positioned such that acceptable performance will be possible. If the performance of the system is deemed unacceptable by programmer 320, the lead may be repositioned by the physician, or an automated delivery system, until the lead resides in a suitable position. Programmer 320 can also be used to communicate feedback from sensors disposed on the leads and housing 104 during the implant procedure.

In some cases, concomitant devices such as another pacemaker, an ICD, or a cutaneous or implantable cardiac monitor, can be present in a patient, along with pulse generator 102. Pulse generator 102 can be configured to communicate with such concomitant devices through transceiver 316 wirelessly, or the concomitant device may be physically connected to pulse generator 102. Physical connection between devices may be accomplished using a lead emanating from pulse generator 102 that is compatible with the concomitant device. For example, the distal end of a lead emanating from pulse generator 102 may be physically and electrically connected to a port contained on the concomitant device. Physical connection between devices may also be accomplished using an implantable adaptor that facilitates electrical connection between the lead emanating from pulse generator 102 and the concomitant device. For example, an adapter may be used that will physically and electrically couple the devices despite not having native components to facilitate such connection. Concomitant devices may be connected using a "smart adapter" that provides electrical connection between concomitant devices and contains signal processing capabilities to convert signal attributes from each respective device such that the concomitant devices are functionally compatible with each other.

Pulse generator 102 can be configured to have a two-way conversation or a one-way conversation with a concomitant device. Controller 302 can be configured to cause the concomitant device to act in concert with pulse generator 102 when providing therapy to the patient, or controller 302 can gather information about the patient from the concomitant device. In some variations, pulse generator 102 can be configured to be triggered via one-way communication from a concomitant device to pulse generator 102.

Figure 4A:
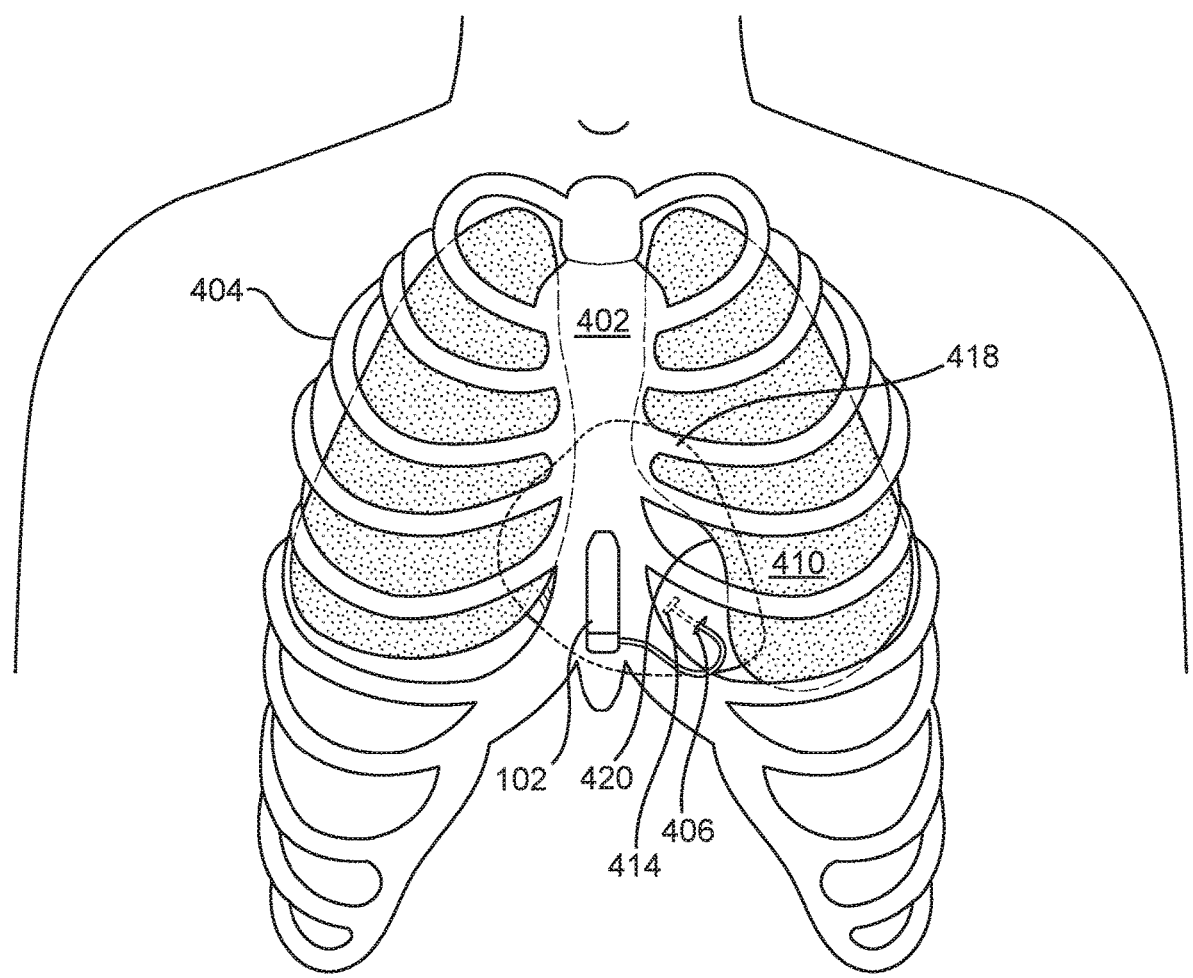
FIG. 4A is an illustration showing exemplary placements of elements of a cardiac pacing system having features consistent with the current subject matter.
Figure 4B:
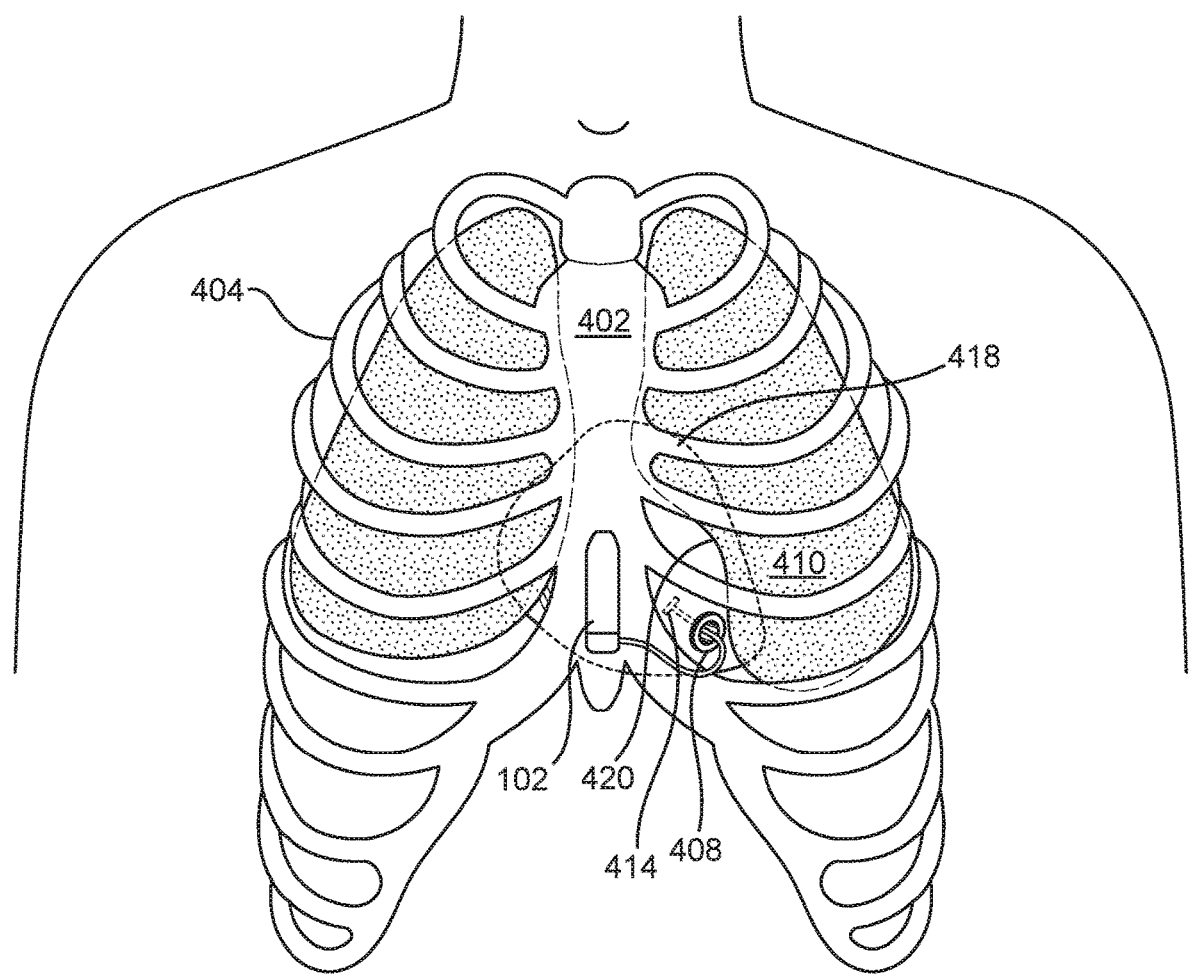
FIG. 4B is an illustration showing exemplary placements of elements of a cardiac pacing system having features consistent with the current subject matter.

FIGS. 4A and 4B are illustrations showing exemplary placements of elements of a cardiac pacing system having features consistent with the present disclosure. Pulse generator 102 can be disposed in a patient, adjacent an outer surface of ribcage 404. For example, pulse generator 102 can be disposed on the sternum 402 of the patient's ribcage 404. A lead 414, attached to pulse generator 102, may also be disposed in the patient by traversing through intercostal muscle 410 of the patient. Lead 414 may optionally pass through a receptacle 408 in intercostal muscle 410 to guide the lead, fix the lead, and/or electrically insulate the lead from the tissue of the intercostal muscle 410 (examples of such receptacles are described herein with respect to FIGS. 13-16).

In other variations, pulse generator 102 can be disposed outside of a patient's ribcage in a pectoral position, outside of the patient's ribcage in a lateral position, below (inferior to) the patient's ribcage in a subxiphoid or abdominal position, within the patient's mediastinum, or the like.

Lead 414 may be passed through the ribcage so the distal end of the lead and its electrodes are disposed on, or pass through, the inner surface of the rib or inner surface of the innermost intercostal muscle, or may alternatively traverse further within the thoracic cavity, but without physically contacting the tissue comprising the heart. This placement may be referred to herein as intracostal or intracostally.

Leads may be inserted between any two ribs within the thoracic cavity, for example, as shown in FIG. 4A. In some variations, it is desirable to insert the lead through one of the intercostal spaces associated with cardiac notch of the left lung 420. For example, between the fourth and fifth ribs or between the fifth and sixth ribs. Due to variations in anatomy, the rib spacing associated with the cardiac notch of the left lung 420 may differ. In some patients the cardiac notch of the left lung 420 may not be present or other cardiac anomalies such as dextrocardia may require the insertion through alternative rib spaces. Lead 414 may be inserted into such a location through an incision 406, as shown in FIG. 4A. Lead 414 may optionally be inserted into such a location through a receptacle 408, as shown in FIG. 4B.

Figure 4C:
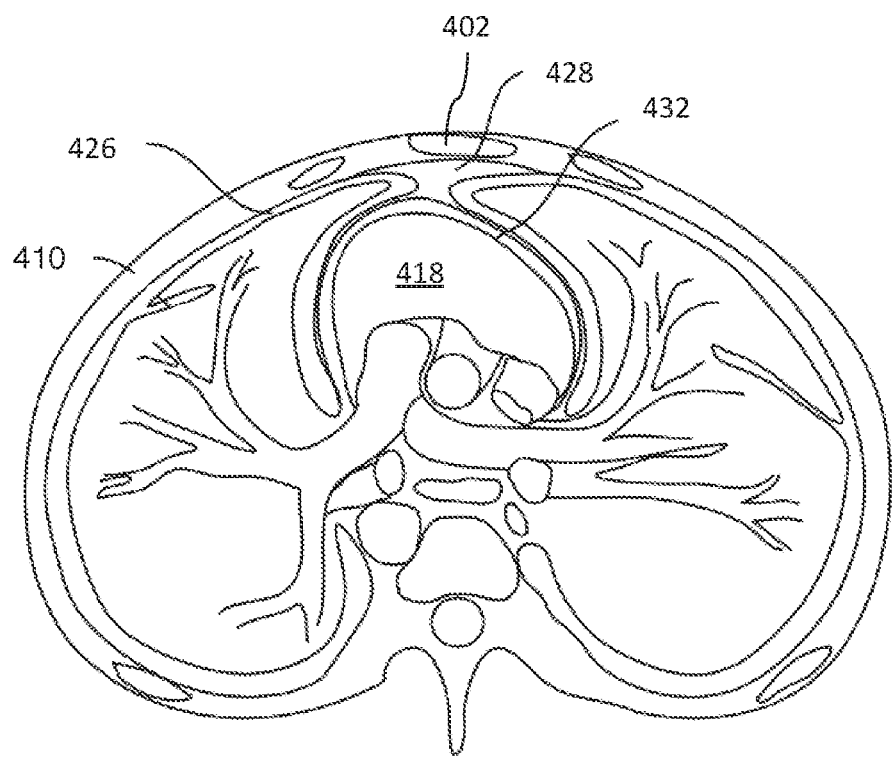
FIG. 4C is a cross-sectional illustration of a thoracic region of a patient.

Precise placement of a distal end of lead 414, which may include electrode(s) for defibrillation, pacing or sensing, is now described further with reference to the anatomical illustrations of FIGS. 4A, 4B and 4C. In some variations, the distal end of lead 414 can be located within the intercostal space or intercostal muscle 410. In such variations, the distal end of lead 414 is preferably surrounded by a receptacle 408 that electrically insulates the distal end of the lead 414 from the intercostal muscle 410. In another variation, the distal end of lead 414 may be placed just on or near the inner surface of a rib or on or near the inner surface of the innermost intercostal muscle. In such instances, and in other placements, the lead 414 may include electrical insulation disposed around the electrode. For example, the lead 414 may include an electrode that is insulated on all sides other than one exposed side. This lead configuration can facilitate a placement where the insulated portions of the lead touch the intercostal muscle, or surrounding tissue, while allowing the electrically active portion of the electrode on the lead to be directional (e.g., directed toward the pericardium and the heart). When electrical stimulation is required, the directional electrode emanates the desired electrical stimulation while electrically insulating the surrounding muscle and tissue from the stimulating energy. In some instances, the electrode may be at the distal tip of the lead, and the insulation surrounds the entire circumference of the lead, but leaves exposed the distal tip. In other instances, an electrode located away from the distal tip of the lead may be insulated over a significant portion of the lead's circumference, for example, approximately 50% or 75% of the circumference may be insulated, leaving only 50% or 25% of the electrode exposed.

The distal end of lead 414 can also be positioned so as to abut the parietal pleura of the lung 426. In other variations, the distal end of lead 414 can be positioned so as to terminate within the mediastinum 428 of the thoracic cavity of the patient, proximate the heart 418, but not physically in contact with the heart 418 or the pericardium 432 of heart 418. Alternatively, the distal end of lead 414 can be placed to abut the pericardium 432, but not physically attach to the epicardial tissue comprising the heart.

A portion of lead 414 may be configured to include a preformed particular shape (e.g., including a 45 degree angle bend, a 90 degree angle bend, a coil, or the like) that enables the preformed portion of lead 414 to be directed towards a preferred location as it is inserted into the patient. For example, the distal end of lead 414 may be preformed so it creates an angle of 90 degrees relative to the main body of lead 414. While lead 414 is being implanted, a sheath or delivery tool may be used to constrain the preformed portion of lead 414 into a straight shape. However, as lead 414 is deployed from the sheath or delivery tool, the preformed portion of lead 414 can revert to its preformed shape. In one instance, the preformed portion of lead 414 reverts to a shape that enables the distal end of lead 414 to reside along and against the posterior surface of the anterior chest wall. Alternatively, a stylet may be used to straighten the preformed shape during the insertion process. Upon removal of the stylet, the preformed shape is again assumed. Any number of preformed shapes are contemplated to facilitate the placement of lead(s) in the positions and particular orientations disclosed herein.

The distal end of lead 414 may be physically affixed to cartilage or bone found within the thoracic cavity, for example, to a rib, to cartilage of a rib, or to other bone or cartilage structure in the thoracic cavity. In one variation, the lead can be disposed such that it is wrapped around the patient's sternum 402 or a patient's rib.

For certain placements, lead 414 can be adequately fixed by direct physical contact with surrounding tissue. In other variations, an additional fixation mechanism may be used at various points along the body of the lead 414. For example, the distal end of lead 414 can incorporate a fixation mechanism such as a tine, hook, spring, screw, or other fixation device. The fixation mechanism can be configured to secure the lead in the surrounding tissue, cartilage, bone, or other tissue, to prevent the lead from migrating from its original implantation location or orientation.

Figure 5:
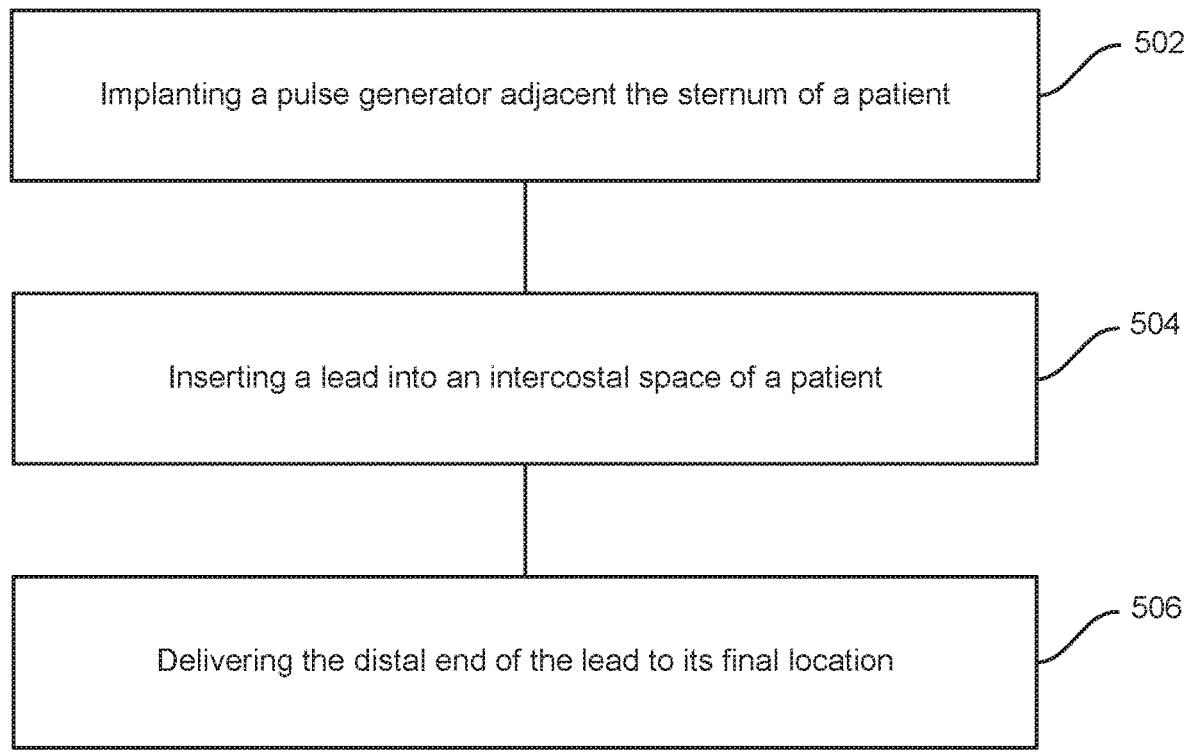
FIG. 5 is an illustration of an exemplary method of implanting a cardiac pacing system into a patient having features consistent with the current subject matter.

FIG. 5 is an illustration 500 of an exemplary method of implanting a cardiac pacing system into a patient consistent with the present disclosure. At 502, a pulse generator 102 may be implanted, in a manner described above, adjacent the sternum 402 of a patient. Optionally, pulse generator 102 may be at least partially chisel-shaped to facilitate implantation and the separation of tissue planes. At 504, a lead 414 may be inserted into an intercostal space 410 of a patient. As described above, lead 414 may optionally be inserted into a receptacle 408 disposed within intercostal space 410. At 506, the distal end of lead 414 is delivered to one of a number of suitable final locations for pacing or defibrillation, as described above.

Figure 6A:
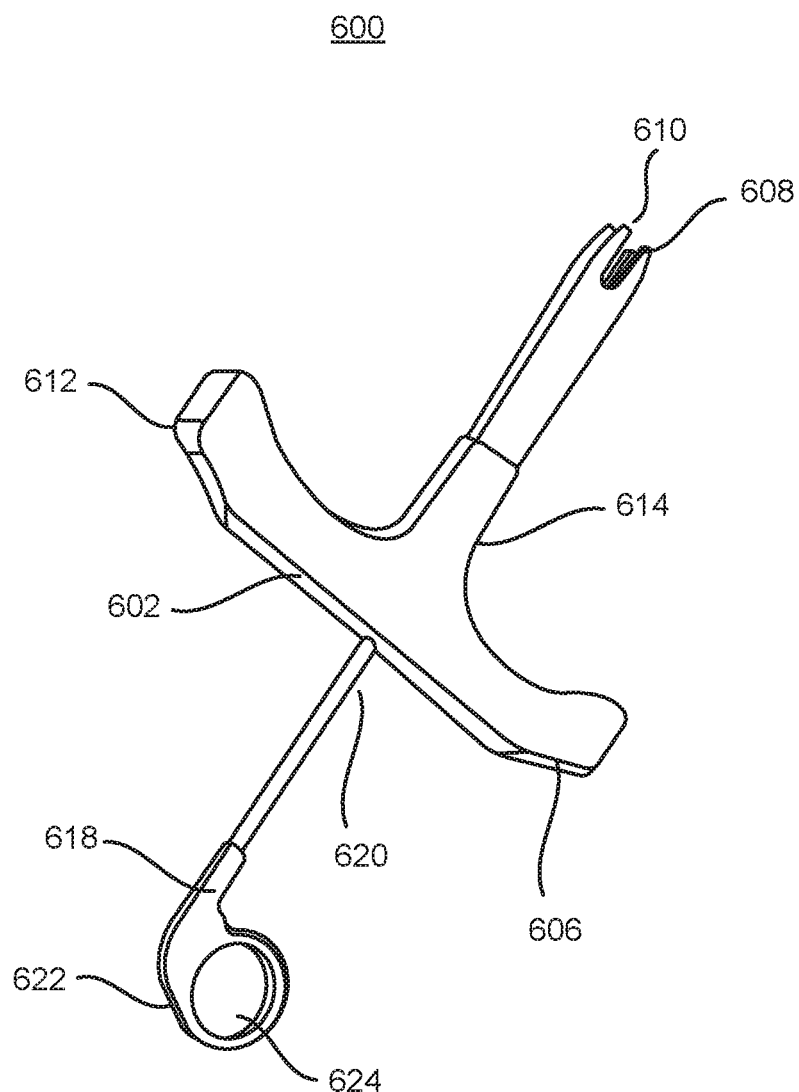
FIG. 6A is an illustration of an exemplary delivery system for a pulse generator having features consistent with implementations of the current subject matter.
Figure 6B:
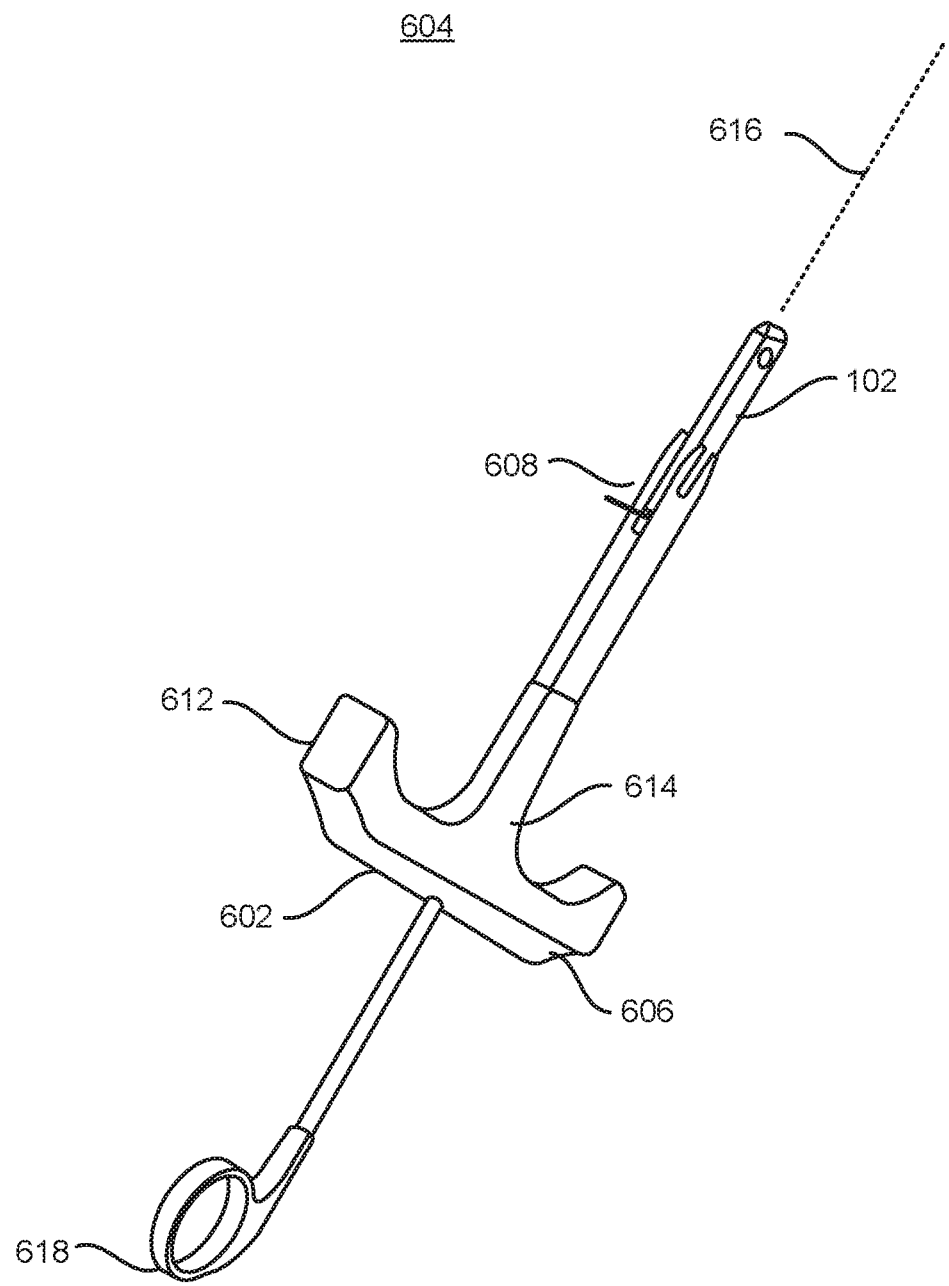
FIG. 6B is an illustration of an exemplary delivery system with a pulse generator disposed therein consistent with implementations of the current subject matter.

FIG. 6A is an illustration 600 of a pulse generator delivery system 602 for facilitating positioning of pulse generator 102 into a patient, the delivery system 602 having features consistent with the current subject matter. FIG. 6B is an illustration 604 of the delivery system 602 as illustrated in FIG. 6A with the pulse generator 102 mounted in it. Delivery system 602 can be configured to facilitate implantation of the pulse generator 102 into the thoracic region of a patient.

Delivery system 602 includes a proximal end 606 and a distal end 608. The distal end 608 of delivery system 602 contains a receptacle 610 in which the housing of the pulse generator 102 is loaded. Where the pulse generator 102 contains a connection lead, the delivery system 602 can be configured to accommodate the connection lead so that the connection lead will not be damaged during the implantation of the pulse generator 102.

When pulse generator 102 is fully loaded into delivery system 602, pulse generator 102 is substantially embedded into the receptacle 610. In some variations, a portion of the pulse generator 102's distal end can be exposed, protruding from the end of receptacle 610. The tapered shape of the distal end 106 of pulse generator 102 can be used in conjunction with the delivery system 602 to assist with separating tissue planes as delivery system 602 is used to advance pulse generator 102 to its desired location within the patient.

In some variations, the entirety of pulse generator 102 can be contained within receptacle 610 of the delivery system 602. The pulse generator 102 in such a configuration will not be exposed during the initial advancement of delivery system 602 into the patient. The distal end 608 of delivery system 602 may be designed to itself separate tissue planes within the patient as delivery system 602 is advanced to the desired location within the patient.

The pulse generator delivery system 602 may be made from a polymer, a metal, a composite material or other suitable material. Pulse generator delivery system 602 can include multiple components. Each component of the pulse generator delivery system 602 can be formed from a material suitable to the function of the component. The pulse generator delivery system 602 can be made from a material capable of being sterilized for repeated use with different patients.

Pulse generator delivery system 602 may include a handle 612. Handle 612 can facilitate advancement of delivery system 602 and pulse generator 102 into a patient's body. Handle 612 can be disposed on either side of the main body 614 of the delivery system 602, as illustrated in FIGS. 6A and 6B. In some variations, handle 612 can be disposed on just one side of the main body 614 of the delivery system 602. The handle 612 can be configured to be disposed parallel to plane of insertion and advancement 616 of pulse generator delivery system 602 within the body. In some variations, handle 612 can be located orthogonally to the plane of insertion and advancement 616 of the delivery system 602. Handle 612 can be configured to facilitate the exertion of pressure, by a physician, onto the pulse generator delivery system 602, to facilitate the advancement and positioning of the delivery system 602 at the desired location within the patient.

Pulse generator delivery system 602 can include a pulse generator release device 618. The release device 618 can be configured to facilitate disengagement of the pulse generator 102 from the delivery system 602. In some variations, release device 618 can include a plunger 620. Plunger 620 can include a distal end configured to engage with the proximal end 606 of the pulse generator delivery system 602. The plunger 620 can engage with the proximal end 606 of the pulse generator delivery system 602 when the pulse generator 102 is loaded into the receptacle 610 of the delivery system 602. The proximal end 622 of the plunger 620 can extend from the proximal end 606 of the delivery system 602.

Plunger 620 can include a force applicator 624. Force applicator 624 can be positioned at the proximal end 622 of plunger 620. Force applicator 624 can be configured to facilitate application of a force to the plunger 620 to advance the plunger 620. Advancing plunger 620 can force pulse generator 102 from the delivery system 602. In some variations, the force applicator 624 can be a ring member. The ring member can facilitate insertion, by the physician, of a finger. Pressure can be applied to the plunger 620 through the ring member, forcing the pulse generator 102 out of the receptacle 610 of the delivery system 602 into the patient at its desired location. In some variations, the proximal end 622 of the plunger 620 can include a flat area, for example, similar to the flat area of a syringe, that allows the physician to apply pressure to the plunger 620. In some variations, the plunger 620 can be activated by a mechanical means such as a ratcheting mechanism.

The distal end 608 of the pulse generator delivery device 602 can include one or more sensors. The sensor(s) can be configured to facilitate detection of a state of patient tissues adjacent distal end 608 of the pulse generator delivery device 602. Various patient tissues can emit, conduct and/or reflect signals. The emitted, conducted and/or reflected signals can provide an indication of the type of tissue encountered by the distal end 608 of the pulse generator delivery device 602. Such sensor(s) can be configured, for example, to detect the electrical impedance of the tissue adjacent the distal end 608 of the pulse generator delivery device 602. Different tissues can have different levels of electrical impedance. Monitoring the electrical impedance can facilitate a determination of the location, or tissue plane, of the distal end 608 of the delivery device 602.

In addition to delivery of the pulse generator, delivery of at least one lead for sensing and/or transmitting therapeutic electrical pulses from the pulse generator is typically required. Proper positioning of the distal end of such lead(s) relative to the heart is very important. Delivery systems are provided that can facilitate the insertion of one or more leads to the correct location(s) in the patient. The delivery systems can facilitate finding the location of the initial insertion point for the lead. The initial insertion point optionally being an intercostal space associated with a patient's cardiac notch of the left lung. The intercostal spaces associated with the cardiac notch commonly include the left-hand-side fourth, fifth and sixth intercostal spaces. Other intercostal spaces on either side of the sternum may be used, especially when the patient is experiencing conditions that prevent use of the fourth, fifth and sixth intercostal spaces, or due to anatomical variations.

When making the initial insertion through the epidermis and the intercostal muscles of the patient, it is important to avoid damaging important blood-filled structures of the patient. Various techniques can be employed to avoid damaging important blood-filled structures. For example, sensors can be used to determine the location of the blood-filled structures. Such sensors may include accelerometers configured to monitor pressure waves caused by blood flowing through the blood-filed structures. Sensors configured to emit and detect light-waves may be used to facilitate locating tissues that absorb certain wavelengths of light and thereby locate different types of tissue. Temperature sensors may be configured to detect differences in temperature between blood-filled structures and surrounding tissue. Lasers and detectors may be employed to scan laser light across the surface of a patient to determine the location of subcutaneous blood-filled structures.

Conventional medical devices may be employed to locate the desired initial insertion point into the patient. For example, x-ray machines, MRI machines, CT scanning machines, fluoroscopes, ultrasound machines and the like, may be used to facilitate determination of the initial insertion point for the leads as well as facilitate in advancing the lead into the patient.

Figure 19:
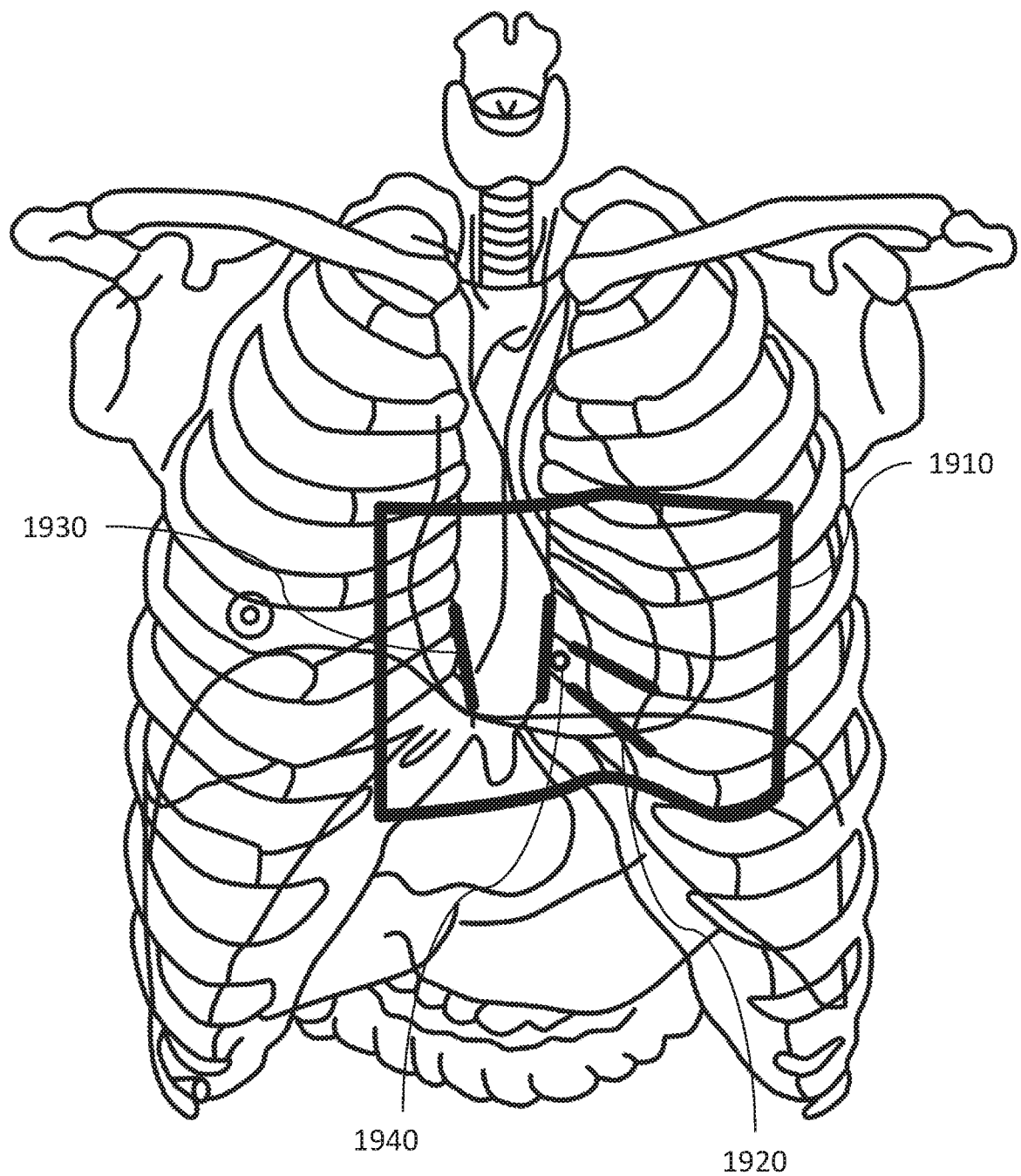
FIG. 19 is an illustration of a medical procedure guide having features consistent with the current subject matter; and, FIG. 20 is an illustration of a medical procedure guide having imaging markers consistent with the current subject matter.

FIG. 19 is an illustration of a medical procedure guide 1910 having features consistent with the current subject matter.

Medical procedure guides can be utilized to bolster the reliability of locating a desired point on a patient for performing a medical procedure. For example, a medical procedure can include, for example, inserting or delivering a lead to a portion of an anatomy of a patient. Medical procedure guides can also identify critical structures to be avoided, for example while inserting the lead during the medical procedure.

For example, the medical procedure guide 1910 may contain markers or regions on the medical procedure guide 1910 meant to be disposed over anatomical locations on the patient. Once the physician has found those anatomical locations (e.g., the xyphoid process), the physician can place the medical procedure guide 1910 so that the markers or desired regions on the medical procedure guide 1910 correlate with those anatomical locations. With the medical procedure guide 1910 properly positioned on the patient, the physician can then use markings on the medical procedure guide 1910 to locate a desired initial insertion point 1940 or to determine the position at which to commence a medical procedure. The medical procedure guide 1910 can be used with many medical procedures including, but not limited to, insertion of a cardiac therapy lead for pacing or defibrillation. In this way, the medical procedure guide 1910 can be configured to allow for puncture or incision through the guide during the medical procedure. Markings, such as critical anatomy markings, on the medical procedure guide 1910 can also indicate structures to be avoided during the lead delivery process. For example, the medical procedure guide 1910 can be configured to further facilitate a determination of the presence or absence of an interposed lung or facilitate a determination of a distance between a sternal margin and a thoracic vein or a thoracic artery.

As used herein, "markings" or "marking regions" refer to marks, recesses, ridges, or other structural features of the medical procedure guide 1910 that are added to the medical procedure guide 1910 (e.g., coloration, changes in opacity, etc.). Markings or marking regions also refer to features that are added to or subtracted from the material that makes up the medical procedure guide 1910. For example, ridges, scoring, recesses, openings and the like.

In some implementations, the medical procedure guide 1910 can have a shape configured to overlay portions of an anatomy of the patient. Portions of the anatomy can include, for example, skin, exposed organs, muscles, tissues, bones, and the like. The shape of the medical procedure guide 1910 can be rectangular, square, circular, oval, or irregular. The medical procedure guide 1910 can be similar to a sheet and have a thickness and an area bounded by a perimeter that overlays the portion of the anatomy. As shown in FIG. 19, the thickness of the medical procedure guild 1910 is variable, and that the depiction shows a greater thickness for illustrative purposes. The medical procedure guide 1910 can be flexible and configured to at least partially form to the anatomy of the patient. The medical procedure guide 1910 can be configured to be affixed to the patient, for example by the inclusion of an adhesive applied to a surface of the medical procedure guide 1910.

The medical procedure guide 1910 can also include alignment markings 1920 on the medical procedure guide 1910 to facilitate proper placement of the medical procedure guide 1910 on the patient. As one example, the alignment markings 1920 can be configured to line up with at least a portion of the patient's sternum and at least one rib.

Procedure markings 1940 can also be included on the medical procedure guide 1910 to facilitate determination of a position at which to commence a medical procedure. For example, the procedure markings 1940 can be configured to locate a position proximate the patient's sternum, in the region of a cardiac notch.

Also, imaging markers may be incorporated with the medical procedure guide 1910 to facilitate commencement or completion of the medical procedure in conjunction with imaging. As used herein, "imaging markers" refer to any markers that are added to or otherwise included with medical procedure guide 1910. A marker can be, in some implementations, an object inserted into or integral with medical procedure guide 1910. In other implementations, the marker can be a feature such as a dye or other material that can be detected by an imaging device or discerned by the human eye. For example, medical procedure guide 1910 can be used with conventional imaging devices such as CT, x-ray, fluoroscopes, MRI, and the like, that can discern the shape and/or location of imaging markers, such as radiopaque markers. In certain embodiments, the medical procedure guide 1910 may contain markers spaced at known intervals that are visible with the imaging devices.

Figure 20:
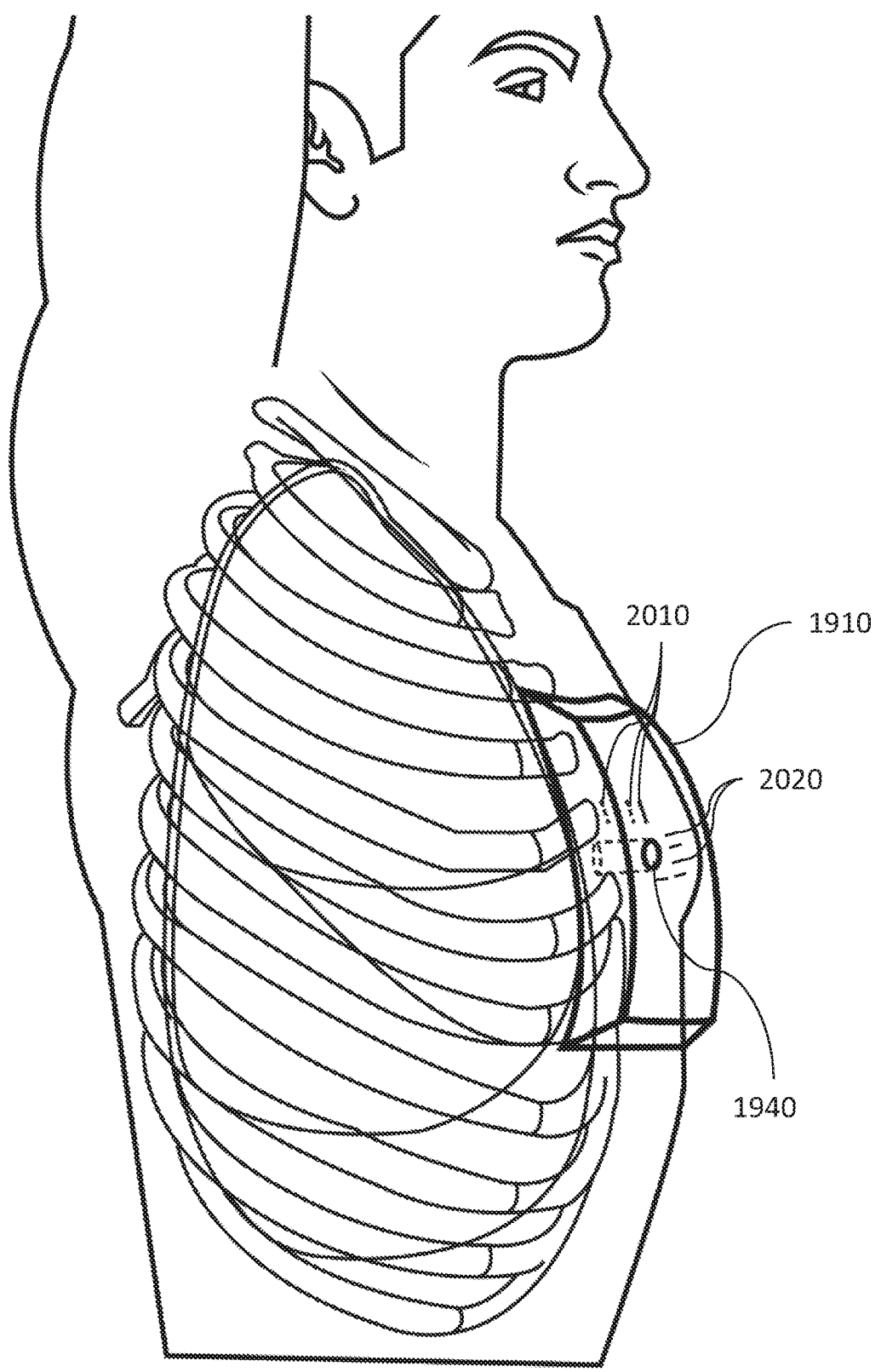

FIG. 20 is an illustration of medical procedure guide 1910 having imaging markers 2010 and 2020 consistent with the current subject matter.

In some implementations, imaging markers 2010 can be located at particular known depths within the medical procedure guide 1910 to facilitate completion of the medical procedure. This is illustrated in FIG. 20, where imaging markers 2010 are shown at several depths proximate to the procedure marking. The imaging markers 2010 can, for example, facilitate determination of a proper depth of insertion for a cardiac therapy lead, a distance between a posterior surface of a sternum and a pericardium, or the determination of the patient's sternum thickness.

In other implementations, medical procedure guide 1910 can include imaging markers 2020 oriented across the face of guide 1910, or at a common depth. As shown in FIG. 20, imaging markers 2020 may be spaced on the surface of medical procedure guide 1910. In one implementation, imaging markers 2020 may form a grid pattern, which can facilitate the location of particular anatomy relative to the grid upon imaging. These reference marks can be radiopaque and/or visible, as described herein. The imaging markers 2020 can facilitate locating a position relevant for a medical procedure, for example, locating a position to make a puncture through medical procedure guide 1910 in order to insert a cardiac therapy lead.

These imaging markers 2010 (which may be radiopaque markers) may also include a complementing marker that is visible to the eye. Radiopaque markers on or within the medical procedure guide may also be configured to be visible only in certain x-ray or fluoroscopy orientations. For example, certain radiopaque markers can be seen predominantly in a sagittal view, while others radiopaque markers can be predominantly viewed while in an AP (anterior-posterior) view. Such orientation specific radiopaque markings can ensure that medical procedure guide 1910 is properly oriented, but can also provide the ability to obtain positional and thickness measurements for the physician. For example, using medical procedure guide 1910 with x-ray or fluoroscopy, the physician can visualize the rib spacing, the presence or absence of interposed lung, the distance between the posterior surface of the sternum and the pericardium, the distance between the sternal margin to the thoracic vein or artery, and the patient's sternum thickness. Having this information, the physician can then determine the ideal intercostal spaces for insertion and ultimate placement and orientation of a lead. As another example, the medical procedure guide 1910 may include critical anatomy markings or facilitate the location critical anatomy to avoid damage during a medical procedure.

The medical procedure guide 1910 may be used with x-ray or fluoroscopy to obtain measurements for the thickness of the subcutaneous tissue between the surface of the skin and the anterior surface of the sternum. With these measurements, the physician can then determine whether the pulse generator will fit well over the sternum, or if other anatomical locations described above are better suited for the pulse generator placement. Additionally, using the medical procedure guide 1910 to obtain measurements related to the thickness of the sternum, the physician can calculate the minimum insertion depth that is necessary to obtain the entry point into the intracostal space. The physician can additionally determine the insertion depth that is necessary for the particular insertion technique (e.g., surgical, percutaneous, etc.) or lead delivery system, as described in detail below.

In one implementation, the medical procedure guide 1910 may consist of a flexible material where the skin facing side of the medical procedure guide 1910 includes a means for temporarily and reversibly adhering to the patient's skin. The medical procedure guide 1910 is positioned in the desired location as described earlier and then adhered to the patient's skin. When viewed under x-ray or fluoroscopy, the caretaker can then determine the desired rib space for lead insertion (for example, above the ventricle) and directly correlate the insertion point with the unique marker on the medical procedure guide 1910.

The medical procedure guide 1910 can be a non-sterile tool that can be used prior to sterile preparation of the patient for identifying the proper insertion point. Medical procedure guide 1910 may include any of the aforementioned alignment markings, procedure markings or imaging markers and each may be used to identify particular important locations for a medical procedure. Medical procedure guide 1910 may be designed so that the locations can be identified, for example, by puncturing through guide 1910 and thereby marking the patient, or alternatively by making markings on the patient adjacent to guide 1910, or within openings in guide 1910. Medical procedure guide 1910 may consist of a thin sterile barrier material, that once properly oriented, is placed on the patient within the sterile field. The medical procedure guide 1910 is adhered to the patient's skin and can remain in place throughout the lead insertion process. In this application, the medical procedure guide 1910 material has properties allowing for an incision by scalpel, needle or the like, to be made directly through the medical procedure guide 1910's sterile barrier material. As described above, the sterile barrier medical procedure guide 1910 may contain unique visible and radiopaque markers to assist with placement, orientation, and lead insertion.

Advancing a lead into a patient can also present the risk of damaging physiological structures of the patient. Sensors may be employed to monitor the characteristics of tissues within the vicinity of the distal end of an advancing lead. Readings from sensors associated with the characteristics of tissues can be compared against known characteristics to determine the type of tissue in the vicinity of the distal end of the advancing lead.

Sensors, such as pH sensors, thermocouples, accelerometers, electrical impedance monitors, and the like, may be used to detect the depth of the distal end of the electrode in the patient. Physiological characteristics of the body change the further a lead ventures into it. Measurements performed by sensors at, or near, the distal end of the advancing lead may facilitate the determination of the type of tissue in the vicinity of the distal end of the lead, as well as its depth into the patient.

Various medical imaging procedures, may be used on a patient to determine the location of the desired positions in the heart for the distal end of the lead(s). This information can be used, in conjunction with sensor readings, of the kind described herein, to determine when the distal end of the lead has advanced to a desired location within the patient.

Components may be used to first create a channel to the desired location for the distal end of the lead. Components can include sheathes, needles, cannulas, balloon catheters and the like. A component may be advanced into the patient with the assistance of sensor measurements to determine the location of the distal end of the component. Once the component has reached the desired location, the component may be replaced with the lead or the lead may be inserted within the component. An example of a component can include an expandable sheath. Once the sheath has been advanced to the desired location, a cannula extending the length of the sheath may be expanded, allowing a lead to be pass through the cannula. The sheath may then be removed from around the lead, leaving the lead in situ with the distal end of the lead at the desired location.

Determination of the final placement of the distal end of a lead is important for the delivery of effective therapeutic electrical pulses for pacing the heart. The present disclosure describes multiple technologies to assist in placement of a lead in the desired location. For example, the use of sensors on the pulse generator, on the distal end of leads, or on delivery components. In addition, when a lead or component is advanced into a patient, balloons may be employed to avoid damaging physiological structures of the patient. Inflatable balloons may be disposed on the distal end of the lead or component, on the sides of a lead body of the lead, or may be circumferentially disposed about the lead body. The balloons may be inflated to facilitate the displacement of tissue from the lead to avoid causing damage to the tissue by the advancing lead. A lead delivery assembly may also be used to facilitate delivery of the lead to the desired location. In some variations, the lead delivery assembly may be configured to automatically deliver the distal end of the lead to the desired location in the patient.

FIG. 7 is an illustration 700 of an exemplary process flow illustrating a method of delivering a lead having features consistent with the present disclosure. At 702, the location of blood-filled structures, in the vicinity of an intercostal space, can be determined. The intercostal space can be an intercostal space associated with the cardiac notch of the patient. Determining the location of the blood-filed structures may be facilitated by one or more sensors configured to detect the location of blood-filled structures.

At 704, a region can be chosen for advancing of a lead through intercostal muscles associated with the cardiac notch. The region chosen may be based on the determined location of blood-filled structures of the patient in that region. It is important that damage to blood-filled structures, such as arteries, veins, and the like, is avoided when advancing a lead into a patient.

At 706, a lead can be advanced through the intercostal muscles associated with the cardiac notch of the patient. Care should be taken to avoid damaging important physiological structures. Sensors, of the kind described herein, may be used to help avoid damage to important physiological structures.

At 708, advancement of the lead through the intercostal muscles can be ceased. Advancement may be ceased in response to an indication that the distal end of the lead has advanced to the desired location. Indication that the distal end of the lead is at the desired location may be provided through measurements obtained by one or more sensors of the kind described herein.

Figure 8A:
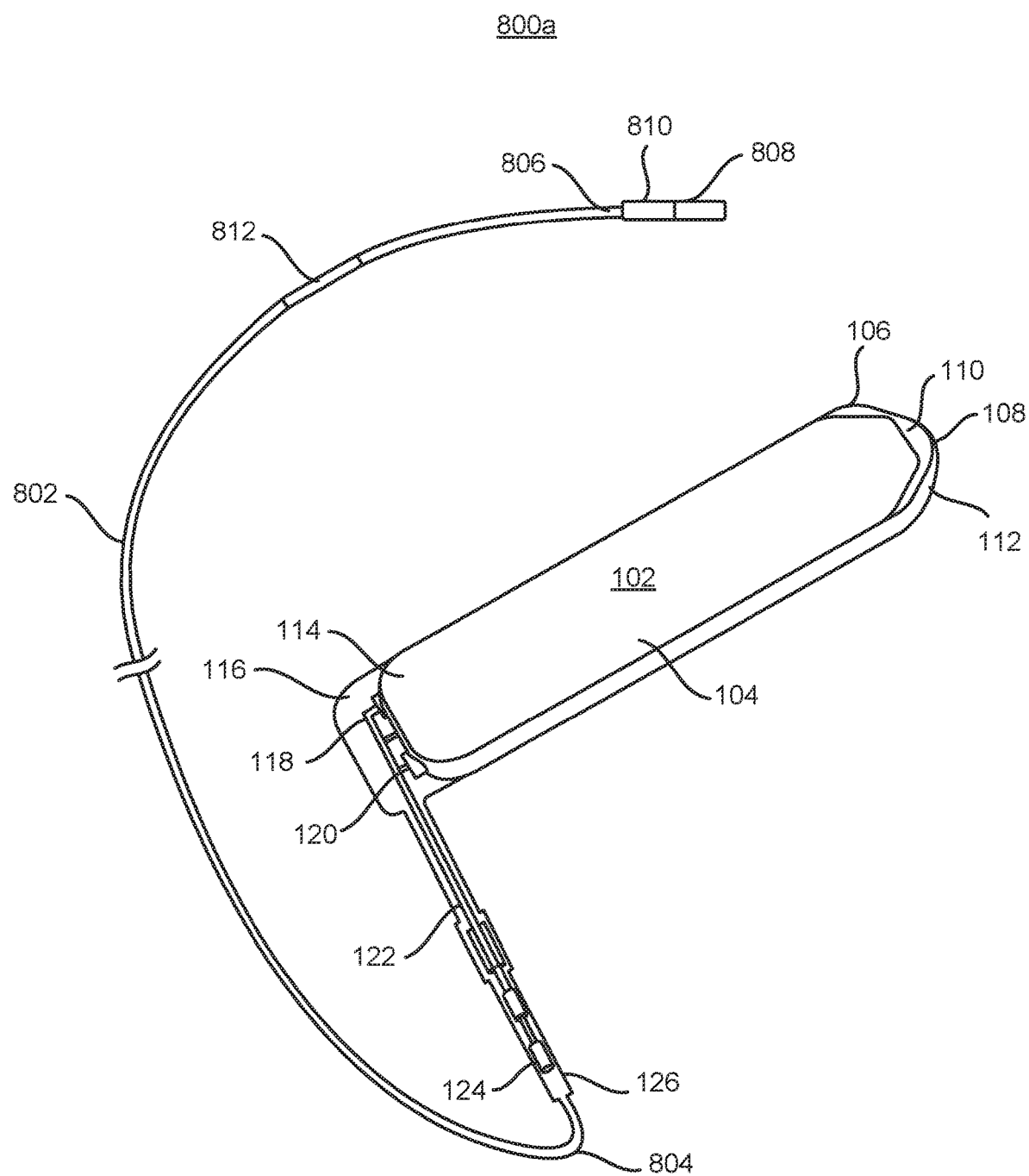
FIG. 8A is an illustration of an exemplary lead having features consistent with the current subject matter.

The lead advanced through the intercostal muscles associated with the cardiac notch of the patient can be configured to transmit therapeutic electrical pulses to pace or defibrillate the patient's heart. FIG. 8A is an illustration 800a of an exemplary lead 802 having features consistent with the present disclosure. For the lead to deliver therapeutic electrical pulses to the heart for pacing or defibrillating the heart, a proximal end 804 of lead 802 is configured to couple with the pulse generator 102. The proximal end 804 of lead 802 may be configured to couple with a connection port 124. The connection port can be configured to couple the proximal end 804 of lead 802 to one or more conductors, such as conductors 118 and 120. When the proximal end 804 of lead 802 couples with connection port 124, a sealed housing may be formed between them. In some variations, the materials of connection port 124 and the proximal end 804 of lead 802 may be fused together. In some variations, the proximal end 804 of lead 802 may be configured to be pushed into the sealed housing 126, or vice versa. Optionally, the external diameter of the inserted member may be slightly greater than the internal diameter of the receiving member causing a snug, sealed fit between the two members. Optionally, a mechanism, such as a set-screw or mechanical lock, may be implemented upon the connection port 124 or proximal lead end 804 in order to prevent unintentional disconnection of the lead 802 from pulse generator 102.

Also shown in FIG. 8A is the distal end 806 of lead 802. The distal end 806 of lead 802 may comprise an electrode 808. In some variations, lead 802 may include a plurality of electrodes. In such variations, lead 802 may include a multiple-pole lead. Individual poles of the multiple-pole lead can feed into separate electrodes. Electrode 808 at the distal end 806 of lead 802 may be configured to deliver electrical pulses to pace or defibrillate the heart when located in the desired position for pacing the heart. Electrodes used for sensing cardiac activity may be oriented on one side of the distal end 806 of lead 802 so that they are facing towards the pericardium and heart, and away from the skeletal muscles in the anterior chest wall and/or surrounding intracostal tissue. Electrodes used for sensing extracardiac activity may be oriented on one or both sides of the distal end 806 of lead 802 or circumferentially around the lead 802. In certain applications, directing electrodes away from the pericardial surface can result in enhanced sensing of extracardiac signals.

The distal end 806 of lead 802 can include one or more sensors 810. Sensor(s) 810 can be configured to monitor physiological characteristics of the patient while the distal end 806 of lead 802 is being advanced into the patient. Sensors can be disposed along the length of lead 802. For example, sensor 812 is disposed some distance from the distal end 806. In such example, sensor 812 may reside in the subcutaneous tissue between the anterior surface of the ribcage and the surface of the skin, providing unique sensing from such a location. Such sensors incorporated onto the lead can detect subtle physiological, chemical and electrical differences that distinguish the lead's placement within the desired location, as opposed to other locations in the patient's thoracic cavity.

In some variations, the proximal end 804 of lead 802 may be coupled with pulse generator 102 prior to the distal end 806 of lead 802 being advanced through the intercostal space of the patient. In some variations, the proximal end 804 of the lead 802 may be coupled with pulse generator 102 after the distal end 806 of lead 802 has been advanced to the desired location.

To assist in the placement of the lead, various medical instruments may be used. The medical instruments may be used alone, or in combination with sensors disposed on the lead that is being placed. Medical instruments may be used to help the physician to access the desired location for the placement of a lead and/or confirm that the distal end of the lead has reached the desired location. For example, instruments, such as an endoscope or laparoscopic camera, with its long, thin, flexible (or rigid) tube, light and video camera can assist the physician in confirming that the distal end 806 of lead 802 has reached the desired location within the thoracic cavity. Other tools known to one skilled in the art such as a guidewire, guide catheter, or sheath may be used in conjunction with medical instruments, such as the laparoscopic camera, and may be advanced alongside and to the location identified by the medical instruments. Medical instruments such as a guidewire can be advanced directly to the desired location for the distal end of the lead with the assistance of acoustic sound, ultrasound, real-time spectroscopic analysis of tissue, real-time density analysis of tissue or by delivery of contrast media that may be observed by real-time imaging equipment.

In some variations, the patient may have medical devices previously implanted that may include sensors configured to monitor physiological characteristics of the patient. The physiological characteristics of the patient may change based on the advancement of the lead through the intercostal space of the patient. The previously implanted medical device may have sensors configured to detect movement of the advancing lead. The previously implanted medical device can be configured to communicate this information back to the physician to verify the location of the advancing lead.

Sensors disposed on the lead, such as sensors 810 disposed on distal end 806 of the lead may be used to facilitate the delivery of the lead to the desired location. Sensor(s) 810 can be configured to facilitate determination of a depth of the distal end 806 of lead 802. As described above, the depth of the desired location within the patient can be determined using one or more medical instruments. This can be determined during implantation of the lead 802 or prior to the procedure taking place.

Although sensor(s) 810 is illustrated as a single element in FIG. 8A, sensor(s) 810 can include multiple separate sensors. The sensors 810 can be configured to facilitate placement of the distal end 806 of the lead 802 at a desired location and verification thereof.

Sensor(s) 810 can be configured to transmit sensor information during advancement to the desired location. Sensor(s) 810 may transmit signals associated with the monitored physiological characteristics of the tissue within the vicinity of the distal end 806 of the lead 802. In some variations, the signals from sensor(s) 810 may be transmitted to a computing device(s) configured to facilitate placement of the lead 802 in the desired location. In such variations, the computing device(s) can be configured to assess the sensor information individually, or in the aggregate, to determine the location of the distal end 806 of lead 802. The computing device(s) can be configured to present alerts and/or instructions associated with the position of the distal end 806 of lead 802.

In some variations, lead 802 can be first coupled with connection port 124 of pulse generator 102. Signals generated by sensor(s) 810 can be transmitted to a computing device(s) using transceiver 316 in pulse generator 102, as illustrated in FIG. 3.

An accelerometer may be used to facilitate delivery of the distal end 806 of lead 802 to the desired location. An accelerometer may be disposed at the distal end 806 of lead 802. The accelerometer may be configured to monitor the movement of the distal end 806 of lead 802. The accelerometer may transmit this information to a computing device or the physician. The computing device, or the physician, can determine the location of the distal end 806 of the lead 802 based on the continuous movement information received from the accelerometer as the lead 802 is advanced into the patient. The computing device or the physician may know the initial entry position for lead 802. The movement information can indicate a continuous path taken by the lead 802 as it advanced into the body of the patient, thereby providing an indication of the location of the distal end 806 of lead 802. Pressure waves from the beating heart may differ as absorption changes within deepening tissue planes. These pressure wave differences may be used to assess the depth of the distal end of the electrode.

The accelerometer can also be configured to monitor acoustic pressure waves generated by various anatomical structures of the body. For example, the accelerometer can be configured to detect acoustic pressure waves generated by the heart or by other anatomical structures of the body. The closer the accelerometer gets to the heart, the greater the acoustic pressure waves generated by the heart will become. By comparing the detected acoustical pressure waves with known models, a location of the distal end 806 of lead 802 can be determined.

Pressure waves or vibrations can be artificially generated to cause the pressure waves or vibrations to traverse through the patient. The pressure waves or vibrations can be generated in a controlled manner. The pressure waves or vibrations may be distorted as they traverse through the patient. The level of type of distortion that is likely to be experienced by the pressure waves or vibrations may be known. The pressure waves or vibrations detected by the accelerometer can be compared to the known models to facilitate determination or verification of the location of the distal end 806 of lead 802.

Different tissues within a body exhibit different physiological characteristics. The same tissues situated at different locations within the body can also exhibit different physiological characteristics. Sensors, disposed on the distal end 806, of lead 802 can be used to monitor the change in the physiological characteristics as the distal end 806 is advanced into the body of the patient. For example, the tissues of a patient through which a lead is advanced can demonstrate differing resistances, physiological properties, electrical impedance, temperature, pH levels, pressures, and the like. These different physiological characteristics, and the change in physiological characteristics, experienced as a sensor traverses through a body can be known or identified. For example, even if the actual degree is not known ahead of time, the change in sensor input when the sensor traverses from one tissue media to another may be identifiable in real-time. Consequently, sensors configured to detect physiological characteristics of a patient can be employed to facilitate determining and verifying the location of the distal end 806 of lead 802.

Different tissues can exhibit different insulative properties. The insulative properties of tissues, or the change in insulative properties of tissues, between the desired entry-point for the lead and the desired destination for the lead can be known. Sensor 810 can include an electrical impedance detector. An electrical impedance detector can be configured to monitor the electrical impedance of the tissue in the vicinity of the distal end 806 of lead 802. The electrical impedance of the tissue monitored by the electrical impedance detector can be compared with the known insulative properties of the tissues between the entry point and the destination, to determine the location of the distal end of lead 802 or a transition from one tissue plane to another may be recognized by a measurable change in the measured impedance.

Varying levels of electrical activity can be experienced at different locations with the body. Electrical signals emitted from the heart, or other muscles can send electrical energy through the body. This electrical energy will dissipate the further it gets from its source. Various tissues will distort the electrical energy in different ways. Sensors configured to detect the electrical energy generated by the heart and/or other anatomical structures can monitor the electrical energy as the lead is advanced. By comparing the monitored electrical energy with known models, a determination or verification of the location of the distal end 806 of lead 802 can be made. The sensors may be configured to identify sudden changes in the electrical activity caused by advancement of the sensor into different tissue planes.

Tissues throughout the body have varying pH levels. The pH levels of tissues can change with depth into the body. Sensor(s) 810 can include a pH meter configured to detect the pH levels of the tissue in the vicinity of the sensor(s) 810 as the sensor(s) advance through the patient. The detected pH levels, or detected changes in pH levels, can be compared with known models to facilitate determination or verification of the location of the distal end 806 of lead 802. The pH meter may be configured to identify sudden changes in the pH level caused by advancement of the meter into different tissue planes.

Different tissues can affect vibration-waves or sound-waves in different ways. Sensor(s) 810 can include acoustic sensors. The acoustic sensors can be configured to detect vibration waves or sound waves travelling through tissues surrounding sensor(s) 810. The vibration waves can be emitted by vibration-emitting devices embedded the lead 802. The vibration waves can be emitted by vibration-emitting devices located on a hospital gurney, positioned on the patient, or otherwise remote from lead 802. Sensor(s) 810 can be configured to transmit detected vibration-wave information to a computing device configured to determine the location of the distal end 806 of lead 802 based on the detected vibration-wave information.

Different tissues can have different known effects on the emitted electromagnetic waves. Sensors can be used to detect the effect that the tissue in the vicinity of the sensors have on the electromagnet waves. By comparing the effect that the tissue has on the electromagnetic waves with known electromagnetic effects, the identity of the tissue can be obtained and the location of the lead can be determined or verified. For example, sensor(s) 810 can include electromagnetic wave sensors. Electromagnetic wave sensors can include an electromagnetic wave emitter and an electromagnetic wave detector. The electromagnetic waves will be absorbed, reflected, deflected, and/or otherwise affected by tissue surrounding sensor(s) 810. Sensor(s) 810 can be configured to detect the change in the reflected electromagnetic waves compared to the emitted electromagnetic waves. By comparing the effect the tissue in the vicinity of the sensor(s) 810 has on the electromagnetic waves with known models, a determination verification of the location of lead 802 can be made. The sensors may be configured to identify sudden changes in the electromagnetic activity caused by advancement of the sensor into different tissue planes.

Figure 9A:
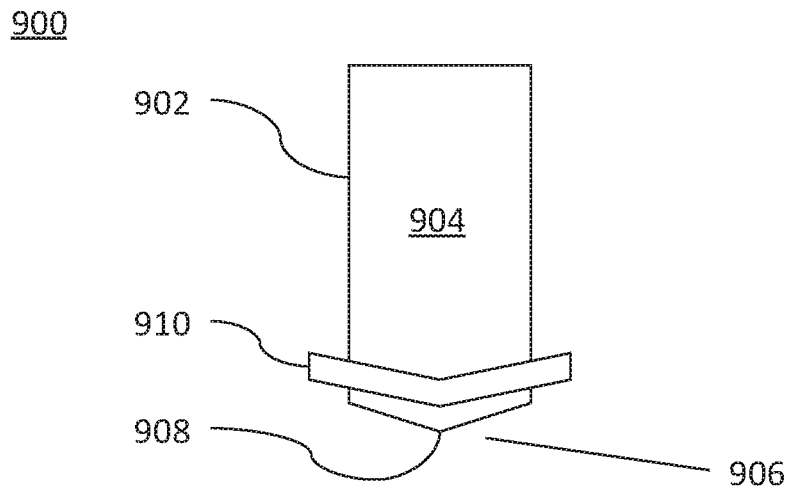
FIG. 9A is an illustration of the distal end of an exemplary delivery system having features consistent with the current subject matter.

FIG. 9A is an illustration 900 of the distal end of an exemplary delivery system 902 having features consistent with the presently described subject matter. While FIG. 9A is described with reference to a delivery system, one of ordinary skill in the art can appreciate and understand that the technology described herein could be applied directly to the end of a lead, such as lead 802. The present disclosure is intended to apply to a delivery system, such as delivery system 902, as well as a lead, such as lead 802.

Delivery system 902 can facilitate placement of the distal end of a lead, such as lead 802 illustrated in FIG. 8, to a desired location by use of electromagnetic waves, such as light waves. Delivery system 902 may comprise a delivery catheter body 904. Delivery catheter body 904 may be configured to facilitate advancement of delivery catheter body 904 into the patient to a desired location. The distal tip 906 of delivery catheter body 904 may comprise a light source 908. Light source 908 can be configured to emit photons having a visible wavelength, infrared wavelength, ultraviolet wavelength, and the like. Delivery catheter body 904 may comprise a light detector 910. Light detector 910 may be configured to detect light waves, emitted by the light source 908, reflected by tissues surrounding distal tip 906 of delivery catheter body 904.

Figure 9B:
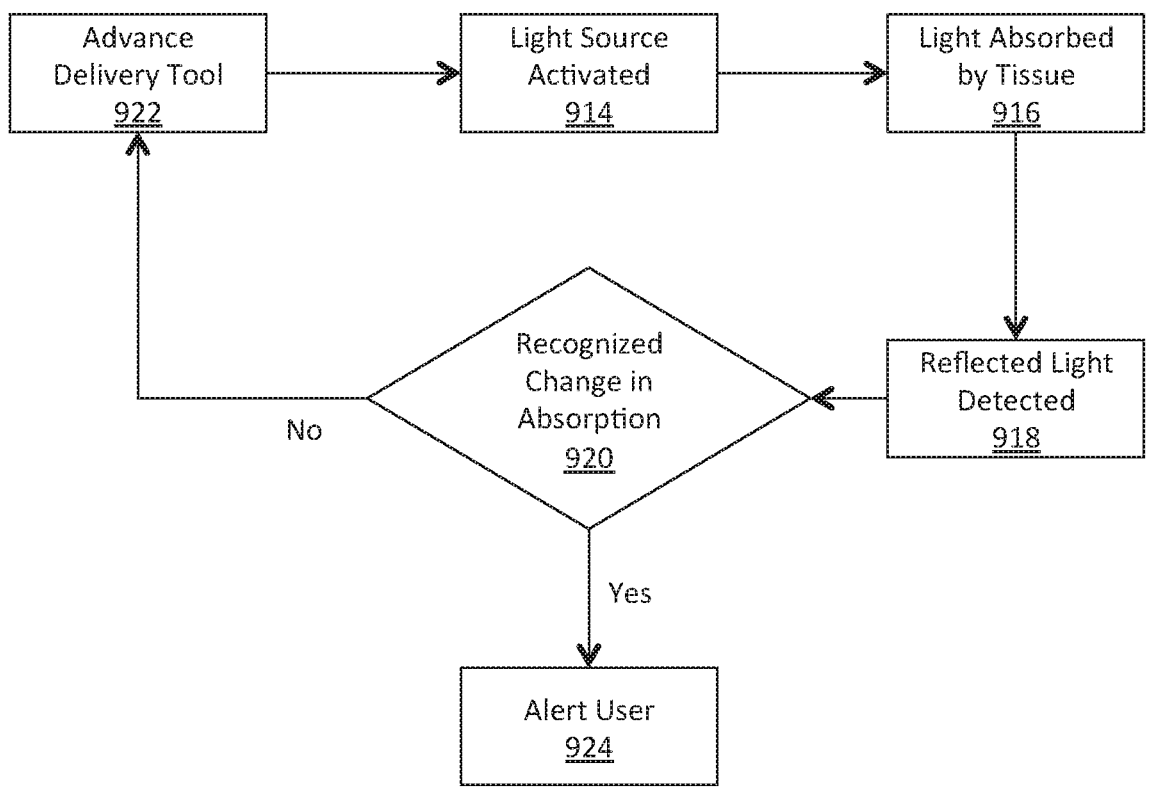
FIG. 9B is an illustration of an exemplary process for using the delivery system illustrated in FIG. 9A.

FIG. 9B is an illustration 912 of an exemplary process for using the delivery system illustrated in FIG. 9A. Light detector 910 can be configured to detect light waves reflected by the tissue adjacent the distal end 906 of delivery system 902. Information associated with the detected light waves may be transmitted to a computing device. The computing device can be configured to interpret the information transmitted from light detector 910 and determine a difference between the light emitted and the light detected.

At 914, light source 908 can be activated. Light source 908 may emit light-waves into the tissue in the general direction of the intended advancement of delivery system 902. At 916, the tissue can absorb a portion of the emitted light waves. At 918, light detector 910 can detect the reflected light waves, reflected by tissues surrounding light source 908. At 920, a determination of a change in the absorption of the light waves by tissues surrounding the distal tip 906 of delivery system 902 can be made.

At 922, in response to an indication that the absorption of light waves has not changed, delivery system 902 can be configured to advance a delivery system, such as delivery system 902, into the patient. In some variations, a physician can advance delivery system 902 into the patient. In other variations, the delivery system 902 can be advanced into the patient automatically.

At 924, in response to an indication that the absorption of light waves has changed, an alert can be provided to the physician. In some variations, the alert can be provided to the physician through a computing device configured to facilitate positioning of delivery system 902 into the patient.

In some variations, a computing device may be configured to facilitate positioning of delivery system 902 into the patient. The computing device can be configured to alert the physician to the type of tissue in the vicinity of distal tip 906 of delivery system 902. In some variations, the computing device can be configured to alert the physician when the distal tip 906 reaches a tissue having characteristics consistent with the desired location of the distal tip 906 of delivery system 902. For example, when the characteristics of the tissue in the vicinity of the distal tip 906 match those within the intercostal tissues, or a particular location within the medistiunum, an alert may be provided.

Blood vessels, both venous and arterial, absorb red, near infrared and infrared (IR) light waves to a greater degree than surrounding tissues. When illuminating the surface of the body with red, near infrared and infrared (IR) light waves, blood rich tissues, for example veins, will absorb more of this light than other tissues, and other tissues will reflect more of this light than the blood rich tissues. Analysis of the pattern of reflections can enable the blood rich tissues to be located. A positive or negative image can be projected on the skin of the patient at the location of the vein. In some variations, the vein can be represented by a bright area and the absence of a vein can be represented as a dark area, or vice versa.

Delivery system 902 can include a subcutaneous visualization enhancer. The subcutaneous visualization enhancer may be configured to enhance visualization of veins, arteries, and other subcutaneous structures of the body. The subcutaneous visualization enhancer can include moving laser light sources to detect the presence of blood-filled structures, such as venous or arterial structures below the surface of the skin. The subcutaneous visualization enhancer can include systems configured to project an image onto the surface of the skin that can show an operator the pattern of the detected subcutaneous blood-filled structures. Laser light from laser light sources can be scanned over the surface of the body using mirrors. A light detector can be configured to measure the reflections of the laser light and use the pattern of reflections to identify the targeted blood rich structures.

Such subcutaneous visualization enhancers can be used to facilitate determination of the location for the initial approach for inserting a lead, such as lead 802, through the intercostal space associated with the cardiac notch of the patient. In some variations, the visualization enhancers can be disposed remote from the delivery system and/or can be configured to enhance visualization enhancers disposed on the delivery system.

With the provision of a visualization of the detected subcutaneous structures, the physician can assess the position of subcutaneous structures such as the internal thoracic artery, or other structures, of the body while concurrently inserting components of the delivery system into the body, while avoiding those subcutaneous structures.

In some variations, during advancement of lead 802 through the intercostal space associated with the cardiac notch, sensor(s) 810 can be configured to transmit obtained readings to a computing device for interpretation. In some variations, the computing device is pulse generator 102. In some variations, pulse generator 102 is used to transmit the readings to an external computing device for interpretation. In any event, the sensor information from the various sensors can be used individually, or accumulatively, to determine the location of the distal end of lead 802.

Figure 10:
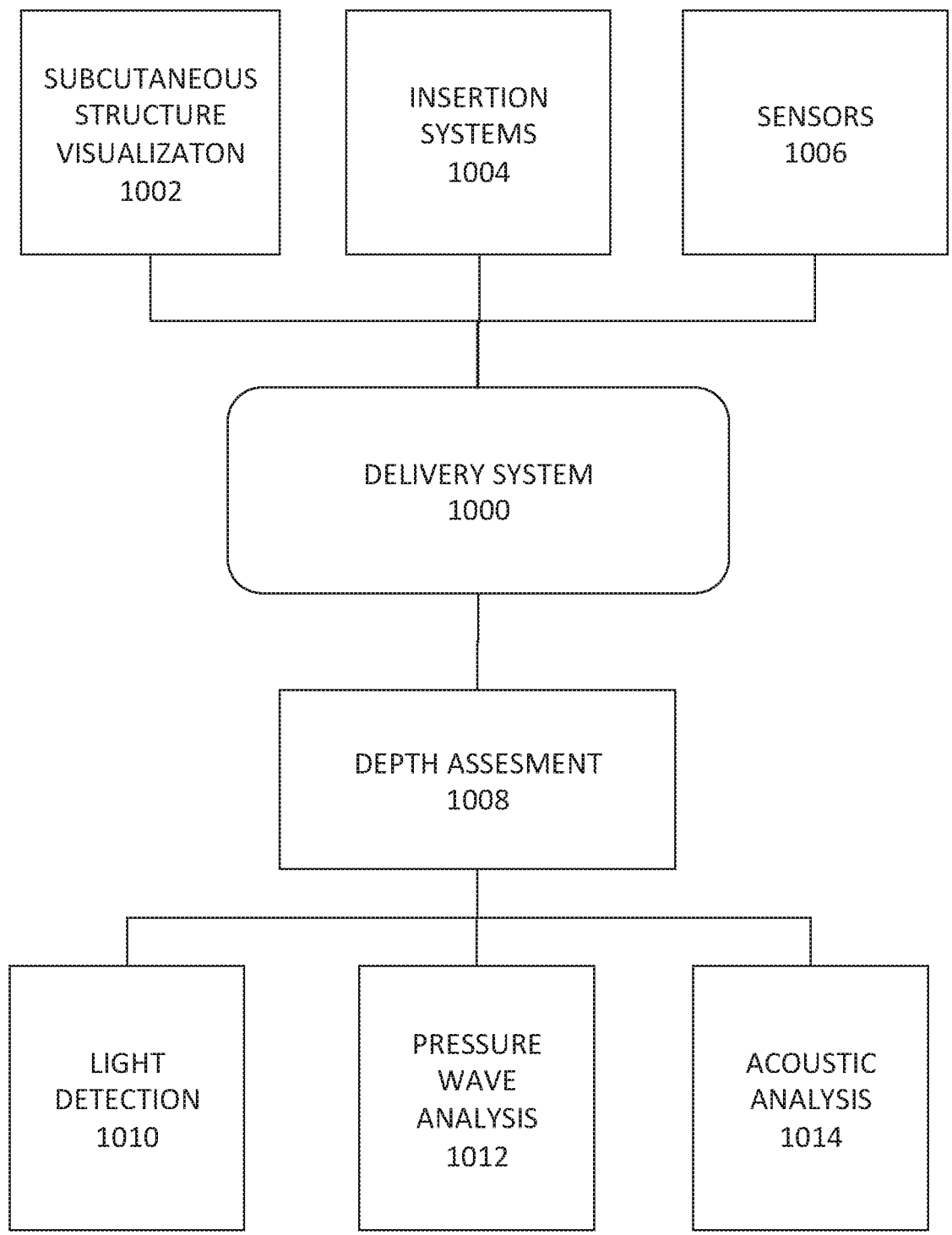
FIG. 10 is a schematic illustration of an exemplary delivery control system having features consistent with the current subject matter.

FIG. 10 is a schematic illustration of a delivery control system 1000 having features consistent with the current subject matter. The delivery control system 1000 can be configured to automatically deliver a lead to the desired position within the patient. For example, the delivery control system 1000 can be configured to automatically deliver a distal tip of a lead through the intercostal space associated with the cardiac notch.

Delivery control system 1000 can be configured to receive a plurality of inputs. The inputs can come from one or more sensors disposed in, or on, the patient. For example, delivery control system 1000 can be configured to receive subcutaneous structure visualization information 1002, information associated with delivery insertion systems 1004, information associated with sensors 1006, and the like.

Delivery control system 1000 can be configured to use remote sensors 1006 to facilitate determination of the insertion site for the lead. Sensors 1006 can be disposed in various instruments configured to be inserted into the patient. Sensors 1006 can also be disposed in various instruments configured to remain external to the patient.

Delivery control system 1000 can be configured to perform depth assessments 1008. The depth assessments 1008 can be configured to determine the depth of the distal end of an inserted instrument, such as a lead 802 illustrated in FIG. 8A. Depth assessments 1008 can be configured to determine the depth of the distal end of the inserted instrument through light detection systems 1010, pressure wave analysis 1012, acoustic analysis, and the like.

Depth assessments 1008 can be configured to determine the depth of the delivery system, or lead, though pressure wave analysis systems 1012. Pressure waves can be detected by accelerometers as herein described.

Depth assessments 1008 can be configured to determine the depth of the delivery system though acoustic analysis systems 1014. Acoustic analysis system 1014 can be configured to operate in a similar manner to a stethoscope. The acoustic analysis system 1014 can be configured to detect the first heart sound (S1), the second heart sound (S2), or other heart sounds. Based on the measurements obtained by the acoustic analysis system 1014, a depth and/or location of the distal end of a delivery system and/or inserted medical component can be determined. The acoustic analysis system 1014 can be configured to measure the duration, pitch, shape, and tonal quality of the heart sounds. By comparing the duration, pitch, shape, and tonal quality of the heart sounds with known models, a determination or verification of the location of the lead can be made. Sudden changes in the degree of heart sounds may be used to indicate advancement into a new tissue plane.

In some variations, the lead can include markers or sensors that facilitate the correct placement and orientation of the lead. Certain markers such as a visual scale, radiopaque, magnetic, ultrasound markers, and the like, can be position at defined areas along the length of the lead so that the markers can be readily observed by an implanting physician, or automated system, on complementary imaging instruments such as fluoroscopy, x-ray, ultrasound, or other imaging instruments known in the art. Through the use of these markers, the physician, or automated implantation device, can guide the lead to the desired location within the intercostal muscle, pleural space, mediastinum, or other desired position, as applicable, and also ensure the correct orientation.

Figure 11A:
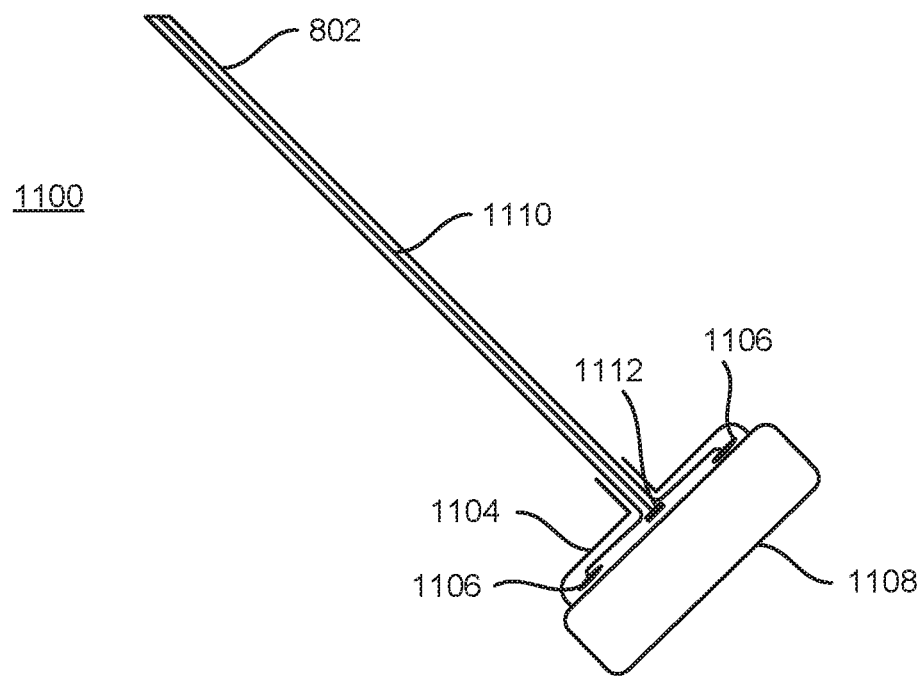
FIGS. 11A and 11B are illustrations of an exemplary lead having features consistent with the current subject matter.
Figure 11B:
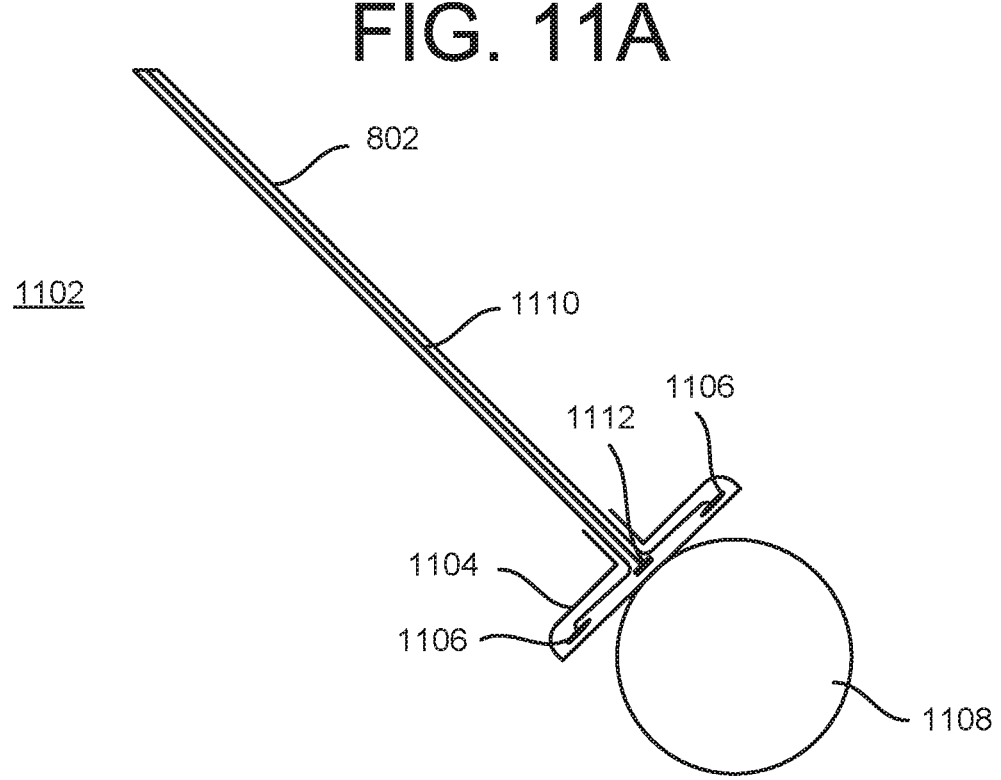

Avoiding damage to tissues in the vicinity of the path-of-travel for the lead is important. Moving various tissues from the path of the lead without damaging them is also important. FIGS. 11A and 11B are illustrations 1100 and 1102 of an exemplary lead 802 having features consistent with the present disclosure for moving and avoiding damage to tissues during lead delivery. Lead 802 can comprise a distal tip 1104. Distal tip 1104 can include at least one electrode and/or sensor 1106.

Having leads directly touch the tissue of a patient can be undesirable and can damage the tissue. Consequently, the distal tip 1104 of lead 802 can include an inflatable balloon 1108. Balloon 1108 can be inflated when the distal tip 1104 of lead 802 encounters an anatomical structure obstructing its path, or prior to moving near sensitive anatomy during lead delivery. The balloon may be configured to divert the obstacle and/or the lead to facilitate circumventing the anatomical structure or may indicate that the lead has reached its intended destination.

To inflate the balloon, lead 802 can include a gas channel 1110. At the end of gas channel 1110 there can be a valve 1112. Valve 1112 can be controlled through physical manipulation of a valve actuator, through electrical stimulation, through pressure changes in gas channel 1110 and/or controlled in other ways. In some variations, the valve 1112 may be configured at the proximal end of the lead 802.

When positioning lead 802 into a patient, lead 802 may cause damage to, or perforations of, the soft tissues of the patient. When lead 802 is being installed into a patient, distal tip 1104 of lead 802 can encounter soft tissue of the patient that should be avoided. In response to encountering the soft tissue of the patient, gas can be introduced into gas channel 1110, valve 1112 can be opened and balloon 1108 can be inflated, as shown in FIG. 11B. Inflating balloon 1108 can cause the balloon to stretch and push into the soft tissue of the patient, moving the soft tissue out of the way and/or guiding distal tip 1104 of lead 802 around the soft tissue. When distal tip 1104 of lead 802 has passed by the soft tissue obstruction, valve 1112 can be closed and the balloon deflated.

Figure 12:
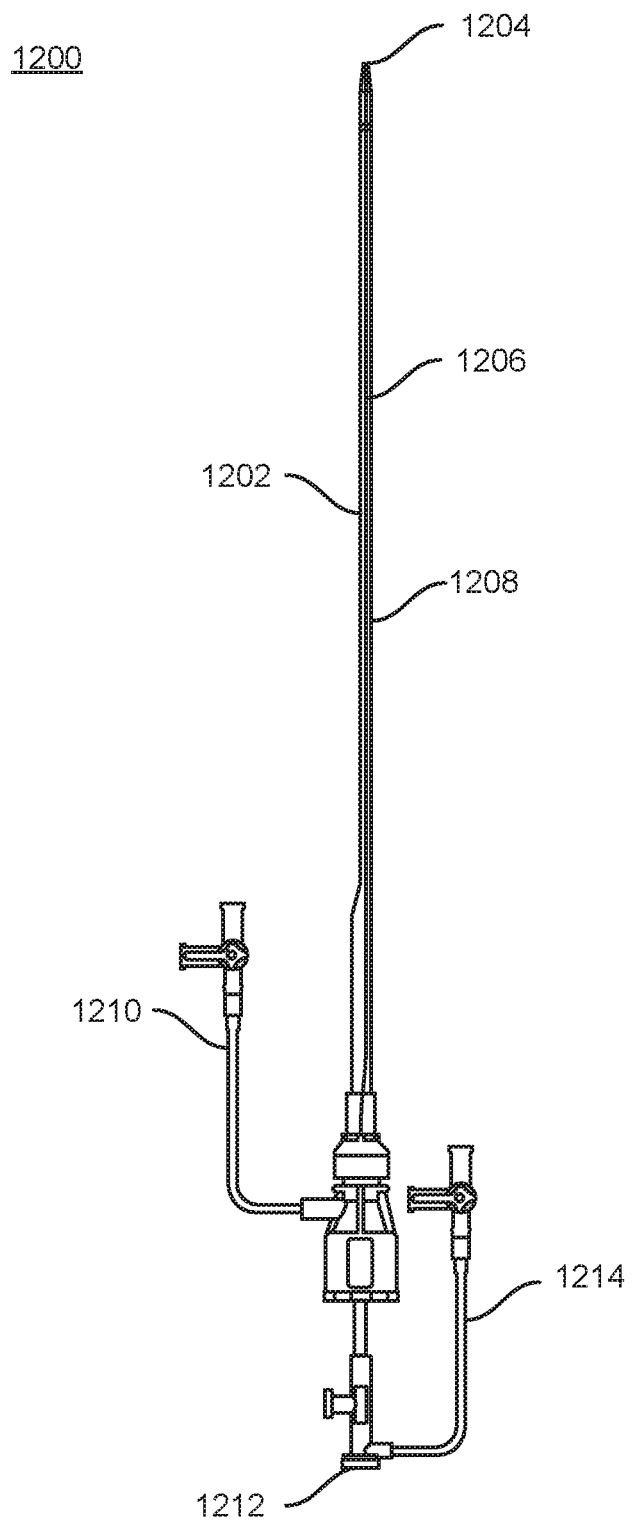
FIG. 12 is an illustration of an exemplary sheath for delivering a lead, the sheath having features consistent with the current subject matter.

In some variations, a delivery component or system is used to facilitate delivery of a lead, such as lead 802, to the desired location. FIG. 12 is an illustration 1200 of an exemplary delivery system for a lead having features consistent with the present disclosure. An example of the delivery system is an expandable sheath 1202. Expandable sheath 1202 can be inserted into the patient at the desired insertion point, identified using one or more of the technologies described herein. Expandable sheath 1202 can include a tip 1204. In some variations, tip 1204 may be radiopaque. A radiopaque tip 1204 may be configured to facilitate feeding of the expandable sheath 1202 to a desired location using one or more radiography techniques known in the art and described herein. Such radiography techniques can include fluoroscopy, CT scan, and the like.

Tip 1204 can include one or more sensors for facilitating the placement of the lead. The sensors included in tip 1204 of the expandable sheath 1202 can be the same or similar to the sensors described herein for monitoring physiological characteristics of the body and other characteristics for facilitating positioning of a lead in a body.

Expandable sheath 1202 can include a channel 1206 running through a hollow cylinder 1208 of expandable sheath 1202. When tip 1204 of expandable sheath 1202 is at the desired location, gas or liquid can be introduced into hollow cylinder 1208. The gas or liquid can be introduced into hollow cylinder 1208 through a first port 1210. Hollow cylinder 1208 can expand, under the pressure of the gas or liquid, causing channel 1206 running through hollow cylinder 1208 to increase in size. A lead, such as lead 802 illustrated in FIG. 8A, can be inserted into channel 1206 through a central port 1212. Hollow cylinder 1208 can be expanded until channel 1206 is larger than the lead. In some variations, channel 1206 can be expanded to accommodate leads of several French sizes. Once the lead is in the desired place, expandable sheath 1202 can be removed, by allowing the lead to pass through channel 1206. In some variations, liquid or gas can be introduced into or removed from channel 1006 through a second port 1214.

Using expandable sheath 1202 can provide an insertion diameter smaller than the useable diameter. This can facilitate a reduction in the risk of damage to tissues and vessels within the patient when placing the lead.

When electricity is brought within the vicinity of muscle tissue, the muscle will contract. Consequently, having a lead for carrying electrical pulses traversing through intercostal muscle tissue may cause the intercostal muscle tissue to contract. Electrical insulation can be provided in the form of a receptacle disposed in the intercostal muscle, where the receptacle is configured to electrically insulate the intercostal muscle from the lead.

Figure 13:
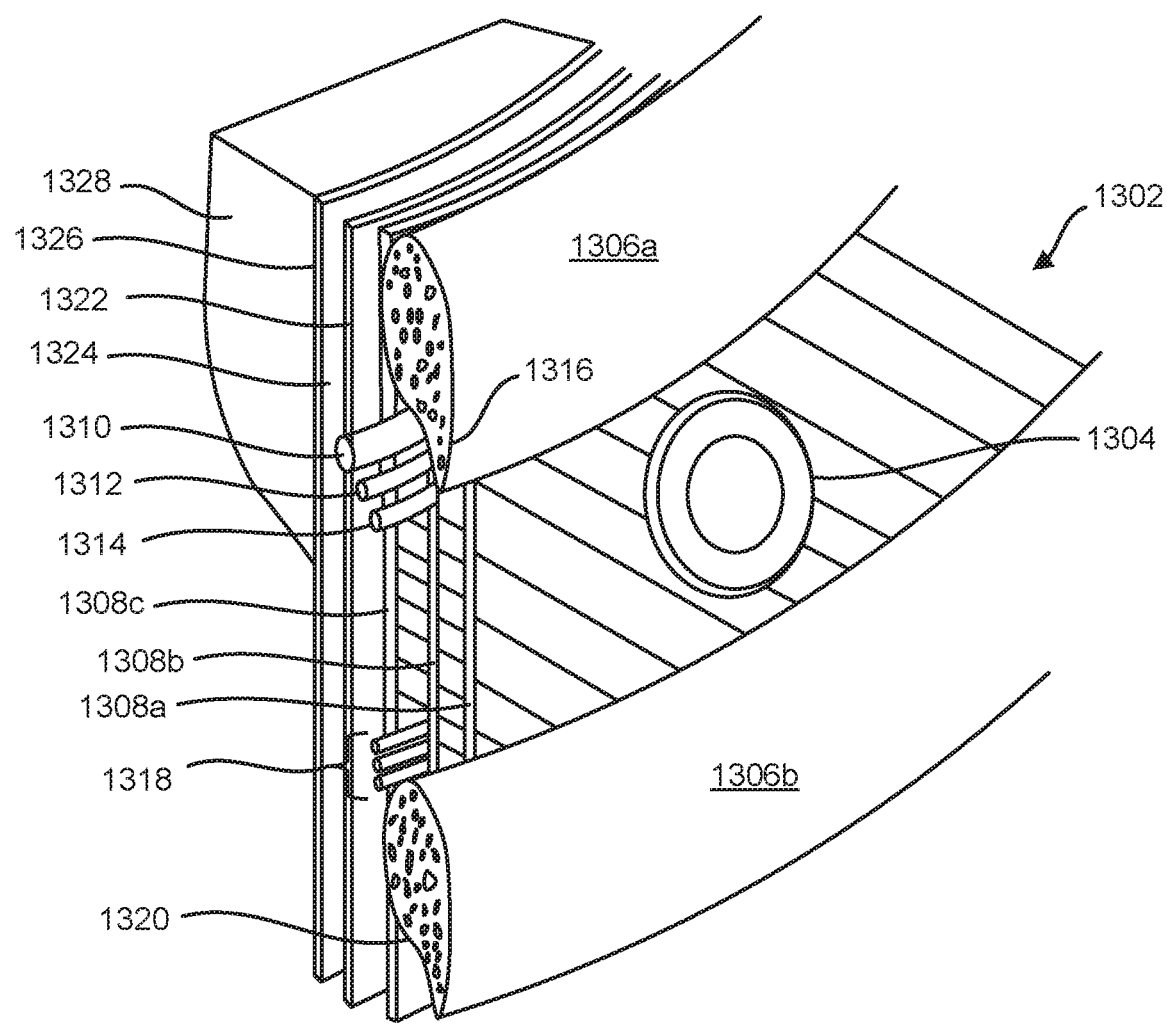
FIG. 13 is an illustration of an intercostal space associated with the cardiac notch of the left lung with an exemplary lead fixation receptacle having features consistent with the current subject matter inserted therein.

FIG. 13 is an illustration 1300 of an intercostal space 1302 associated with the cardiac notch of the left lung with an exemplary lead receptacle 1304 having features consistent with the present disclosure. Lead receptacle 1304 can facilitate the placement of leads, and/or other instruments and avoid the leads and/or instruments physically contacting the intercostal tissue. When the distal end of the lead is positioned to terminate in the intercostal muscle, the lead can be passed through lead receptacle 1304 that has been previously placed within the patient's intercostal muscles. Lead receptacle 1304 can be configured to be electrically insulated so that electrical energy emanating from the lead will not stimulate the surrounding intercostal and skeletal muscle tissue, but will allow the electrical energy to traverse through and stimulate cardiac tissue.

The intercostal space 1302 is the space between two ribs, for example, rib 1306a and rib 1306b. Intercostal muscles 1308a, 1308b and 1308c can extend between two ribs 1306a and 1306b, filling intercostal space 1302. Various blood vessels and nerves can run between the different layers of intercostal muscles. For example, intercostal vein 1310, intercostal artery 1312, the intercostal nerve 1314 can be disposed under a flange 1316 of upper rib 1306a and between the innermost intercostal muscle 1308c and its adjacent intercostal muscle 1308b. Similarly, collateral branches 1318 can be disposed between the innermost intercostal muscle 1308c and its adjacent intercostal muscle 1308b.

The endothoracic facia 1320 can abut the inner-most intercostal muscle 1308c and separate the intercostal muscles from the parietal pleura 1322. The pleural cavity 1324 can be disposed between the parital pleura 1322 and the visceral pleura 1326. The visceral pleura 1326 can abut the lung 1328.

Figure 14:
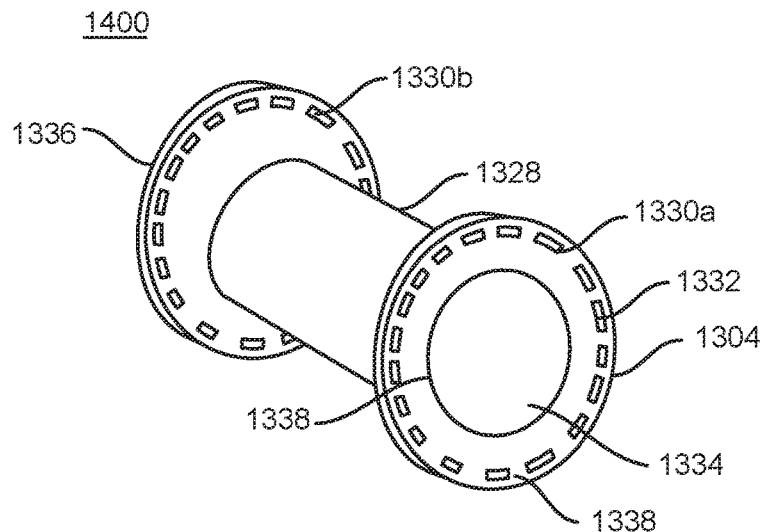
FIG. 14 is an illustration of an exemplary lead fixation receptacle having features consistent with the current subject matter.

FIG. 14 is an illustration 1400 of an exemplary lead fixation receptacle 1304 illustrated in FIG. 13, having features consistent with the present disclosure.

Lead receptacle 1304 may comprise a cylindrical body, or lumen 1328, from an outer side of an outermost intercostal muscle to an inner side of an innermost intercostal muscle of an intercostal space. Lumen 1328 may be configured to support a lead traversing through it. Lumen 1328 may comprise an electrically insulating material configured to inhibit traversal of electrical signals through walls of lumen 1328. In some variations, end 1336 of the receptacle 1304 may pass through the innermost intercostal muscle 1308c. In some variations, end 1338 of receptacle 1304 can pass through outermost intercostal muscle 1308a.

Lumen 1328 can terminate adjacent the pleural space 1324. In some variations, the lumen 1328 can terminate in the mediastinum. In some variations, receptacle 1304 can be configured to be screwed into the intercostal muscles 1308a, 1308b, and 1308c. Receptacle 1304 can also be configured to be pushed into the intercostal muscles 1308a, 1308b and 1308c.

Lead receptacle 1304 may include a fixation flange 1330a. Fixation flange 1330a may be disposed on the proximal end of the lumen 1328 and configured to abut the outermost intercostal muscle 1308a. Lead receptacle 1304 may include a fixation flange 1330b. Fixation flange 1330b can be disposed on the distal end of the lumen 1328 and configured to abut the outermost intercostal muscle 1308c. Lead receptacle 1304 can be implanted into the intercostal muscles 1308a, 1308b, and 1308c by making an incision in the intercostal muscles 1308a, 1308b, and 1308c, stretching the opening and positioning lead receptacle 1304 into the incision, taking care to ensure that the incision remains smaller than the outer diameter of flanges 1330a and 1330b. In some variations flanges 1330a and 1330b can be configured to be retractable allowing for removal and replacement of the lead fixation receptacle 1304.

Lead receptacle 1304 can be fixed in place by using just flanges 1330a and 1330b. Lead receptacle 1304 may also be fixed in place by using a plurality of surgical thread eyelets 1332. Surgical thread eyelets 1332 can be configured to facilitate stitching lead receptacle 1304 to the intercostal muscles 1308a and 1308c to fix lead receptacle 1304 in place.

Receptacle 1304 can include an internal passage 1334. Internal passage 1334 can be configured to receive one or more leads and facilitate their traversal through the intercostal space 1302.

Lead receptacle 1304 can be formed from an electrically insulating material. The electrically insulating material can electrically isolate the intercostal muscles 1308a, 1308b and 1308c from the leads traversing through lead receptacle 1304.

Lead receptacle 1304 can be formed from materials that are insulative. The material can include certain pharmacological agents. For example, antibiotic agents, immunosuppressive agents to avoid rejection of lead receptacle 1304 after implantation, and the like. In some variations, lead receptacle 1304 can be comprised of an insulative polymer coated or infused with an analgesic. In some variations, the lead receptacle 1304 can be comprised of an insulative polymer coated or infused with an anti-inflammatory agent. The polymer can be coated or infused with other pharmacological agents known to one skilled in the art to treat acute adverse effects from the implantation procedure or chronic adverse effects from the chronic implantation of the lead or receptacle within the thoracic cavity.

Figure 15:
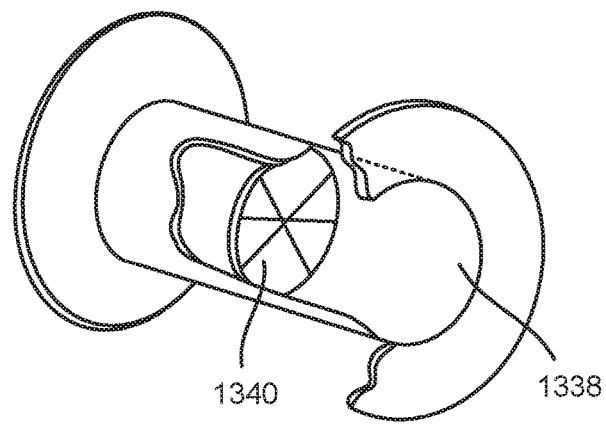
FIG. 15 is an illustration of an exemplary lead fixation receptacle having features consistent with the current subject matter.

FIG. 15 is an illustration of lead receptacle 1304 having features consistent with the present disclosure. Lead fixation receptacle can comprise a septum 1340, or multiple septums disposed traversely within lumen 1338. Septum 1340 can be selectively permeable such that when a lead is inserted through septum 1340, septum 1340 can be configured to form a seal around the lead traversing through lumen 1338 to prevent the ingress or egress of gas, fluid, other materials, and the like, through lumen 1338. Septum 1340 may optionally permit the egress of certain gas and fluid but prevent ingress of such materials through lumen 1338.

In some variations, the lead receptacle can comprise multiple lumens. For example, lead receptacle can comprise a second lumen configured to traverse from an outermost side of an outermost intercostal muscle to an innermost side of an innermost intercostal muscle. Second lumen can be configured to facilitate dispensing of pharmacological agents into the thorax of the patient.

The lumens for such a lead receptacle can be used for differing purposes in addition to the passage of a single lead into the pleural space or mediastinum. The multiple lumens can provide access for multiple leads to be passed into the pleural space or mediastinum.

Figure 16:
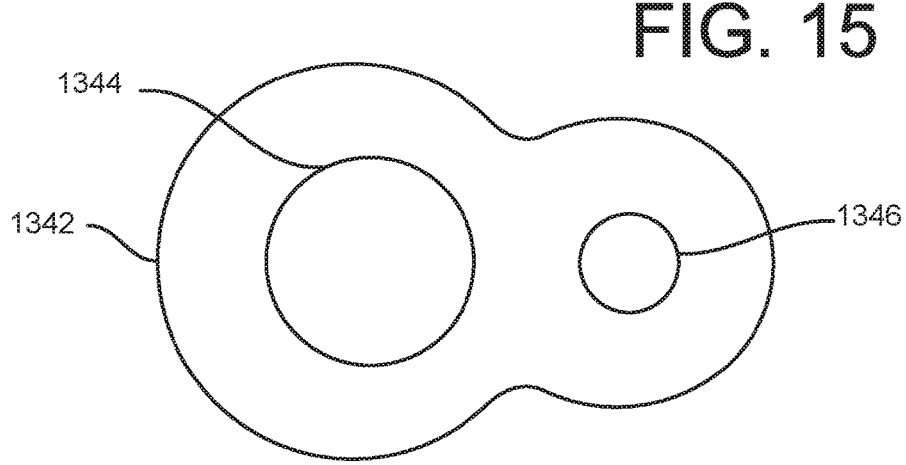
FIG. 16 is an illustration of an exemplary lead fixation receptacle having features consistent with the current subject matter.

FIG. 16 is an illustration of an exemplary lead fixation receptacle 1342 having features consistent with the present disclosure. Lead fixation receptacle 1342 can include a first lumen 1344, similar to lumen 1338 of the lead receptacle 1304 illustrated in FIGS. 14 and 15. Lead fixation receptacle 1342 can include an additional lumen 1346. Additional lumen 1346 can be provided as a port to provide access to the thoracic cavity of the patient. Access can be provided to facilitate dispensing of pharmacological agents, such as pharmacological agents to treat various adverse effects such as infection or pain in the area surrounding lead receptacle 1342, pleural space, mediastinum, and/or other areas surrounding the thoracic cavity of the patient. Additional lumen 1346 can provide access for treatment of other diseases or disorders affecting organs or other anatomical elements within the thoracic cavity. For example, additional lumen 1346 can facilitate the evacuation of gas or fluid from the thorax, and the like.

The lead receptacle as described with reference to FIGS. 13-16 can be fixated to cartilage, or bone within the thoracic cavity. In some variations, the lead receptacle can be configured to be disposed between the intercostal muscles and a rib, thereby potentially reducing damage to the intercostal muscles caused by its insertion. The lead receptacle can be in passive contact with tissue surrounding the cardiac notch. For example, the lead receptacle can abut the superficial facia on the outermost side and the endothoracic facia or the parietal pleura on the innermost side.

In some variations, the lead receptacle can be actively fixed into position using one end of the lead receptacle. For example, only one flange can include surgical thread holes to facilitate sewing of the flange into the intercostal muscles.

Active fixation, whether at flanges, or along the lumen of the lead fixation receptacle, can include, for example, the use of tines, hooks, springs, screws, flared wings, flanges and the like. Screws can be used to screw the lead fixation receptacle into bone or more solid tissues within the thoracic cavity. Hooks, tines, springs, and the like, can be used to fix the lead fixation receptacle into soft tissues within the thoracic cavity.

In some variations the lead receptacle can be configured to facilitate in-growth of tissue into the material of which the lead fixation receptacle is comprised. For example, the lead fixation receptacle can be configured such that bone, cartilage, intercostal muscle tissue, or the like, can readily grow into pockets or fissures within the surface of the lead receptacle. Facilitating the growth of tissue into the material of the lead receptacle can facilitate fixation of the receptacle.

In some variations, the receptacle can be configured to actively fix between layers of the intercostal muscle. With reference to FIG. 13, the layered nature of the intercostal muscle layers 1308a, 1308b and 1308c can be used to facilitate fixation of the lead receptacle into the intercostal space. For example, flanges can be provided that extend between the intercostal muscle layers. Incisions can be made at off-set positions at each layer of intercostal muscle such that when the lead receptacle is inserted through the incisions, the intercostal muscles apply a transverse pressure to the lead receptacle keeping it in place. For example, a first incision can be made in the first intercostal muscle layer 1308a, a second incision can be made in the second intercostal muscle layer 1308b, offset from the first incision, and a third incision can be made to the third intercostal muscle layer 1308c in-line with the first incision. Inserting the lead receptacle through the incisions, such that the lead receptacle is situated through all three incisions, will cause the second intercostal muscle layer 1308b to apply a transverse pressure to the lead receptacle that is countered by the first intercostal muscle layer 1308a and the third intercostal muscle layer 1308c, facilitating keeping the lead receptacle in place.

Sensing and detection will be performed using one or more available signals to determine when pacing should be delivered or inhibited. Cardiac signals will be measured from one or more electrodes. Additional non-cardiac sensors may also be used to enhance the accuracy of sensing and detection. Such sensors include, but are not limited to rate response sensors, posture/positional sensors, motion/vibration sensors, myopotential sensors and exogenous noise sensors. One or more algorithms will be utilized to make decisions about pacing delivery and inhibition. Such algorithms will evaluate available signal attributes and relationships, including but not limited to analysis of morphology, timing, signal combinations, signal correlation, template matching or pattern recognition.

A pulse generator, such as pulse generator 102 illustrated in FIG. 1, can be configured to monitor physiological characteristics and physical movements of the patient. Monitoring can be accomplished through sensors disposed on, or in, the pulse generator, and/or through sensors disposed on one or more leads disposed within the body of the patient. The pulse generator can be configured to monitor physiological characteristics and physical movements of the patient to properly detect heart arrhythmias, dyssynchrony, and the like.

Sensor(s) can be configured to detect an activity of the patient. Such activity sensors can be contained within or on the housing of the pulse generator, such as pulse generator 102 illustrated in FIG. 1. Activity sensors can comprise one or more accelerometers, gyroscopes, position sensors, and/or other sensors, such as location-based technology, and the like. Sensor information measured by the activity sensors can be cross-checked with activity information measured by any concomitant devices.

In some variations, an activity sensor can include an accelerometer. The accelerometer can be configured to detect accelerations in any direction in space. Acceleration information can be used to identify potential noise in signals detected by other sensor(s), such as sensor(s) configured to monitor the physiological characteristics of the patient, and the like, and/or confirm the detection of signals indicating physiological issues, such as arrhythmias or other patient conditions.

In some variations, a lead, such as lead 802 in FIG. 8, can be configured to include sensors that are purposed solely for monitoring the patient's activity. Such sensors may not be configured to provide additional assistance during the implantation procedure. These sensors can include pulmonary, respiratory, minute ventilation, accelerometer, hemodynamic, and/or other sensors. Those sensors known in the art that are used to real-time, or periodically monitor a patient's cardiac activity can be provided in the leads. These sensors are purposed to allow the implanted device to sense, record and in certain instances, communicate the sensed data from these sensors to the patient's physician. In alternative embodiments, the implanted medical device may alter the programmed therapy regimen of the implanted medical device based upon the activity from the sensors.

In some variations, sensors, such as sensors 810 and 812 of FIG. 8A, may be configured to detect the condition of various organs and/or systems of the patient. Sensor(s) 810, 812 can be configured to detect movement of the patient to discount false readings from the various organs and/or systems. Sensor(s) 810, 812 can be configured to monitor patient activity. Having a distal end 806 of lead 802 positioned in the cardiac notch abutting the parietal pleura, sensor(s) 810, 812 can collect information associated with the organs and/or systems of the patient in that area, for example the lungs, the heart, esophagus, arteries, veins and other organs and/or systems. Sensor(s) 810 can include sensors to detect cardiac ECG, pulmonary function, sensors to detect respiratory function, sensors to determine minute ventilation, hemodynamic sensors and/or other sensors. Sensors can be configured independently to monitor several organs or systems and/or configured to monitor several characteristics of a single organ simultaneously. For example, using a first sensor pair, the implanted cardiac pacing system may be configured to monitor the cardiac ECG signal from the atria, while simultaneously, a second sensor pair is configured to monitor the cardiac ECG signal from the ventricles.

A lead disposed in the body of a patient, such as lead 802 of FIG. 8A, can include sensors at other areas along the lead, for example, sensors 812. The location of sensors 812 along lead 802 can be chosen based on proximity to organs, systems, and/or other physiological elements of the patient. The location of sensors 812 can be chosen based on proximity to other elements of the implanted cardiac pacing system.

Additional leads may be used to facilitate an increase in the sensing capabilities of the implantable medical device. In one embodiment, in addition to at least one lead disposed within the intercostal muscle, pleural space or mediastinum, another lead is positioned subcutaneously and electrically connected to the implantable medical device. The subcutaneously placed lead can be configured to enhance the implantable medical device's ability to sense and analyze far-field signal's emitted by the patient's heart. In particular, the subcutaneous lead enhances the implantable medical device's ability to distinguish signals from particular chambers of the heart, and therefore, appropriately coordinate the timing of the required pacing therapy delivered by the implantable medical device.

Additional leads in communication with the implantable medical device or pulse generator, and/or computing device, can be placed in other areas within the thoracic cavity in order to enhance the sensing activity of the heart, and to better coordinate the timing of the required pacing therapy delivered by the implantable medical device. In certain embodiments, these additional leads are physically attached to the implantable medical device of the present disclosure.

The leads used to deliver therapeutic electrical pulses to pace the heart can comprise multiple poles. Each pole of the lead can be configured to deliver therapeutic electrical pulses and/or obtain sensing information. The different leads can be configured to provide different therapies and/or obtain different sensing information. Having multiple sensors at multiple locations can increase the sensitivity and effectiveness of the provided therapy.

Figure 8B:
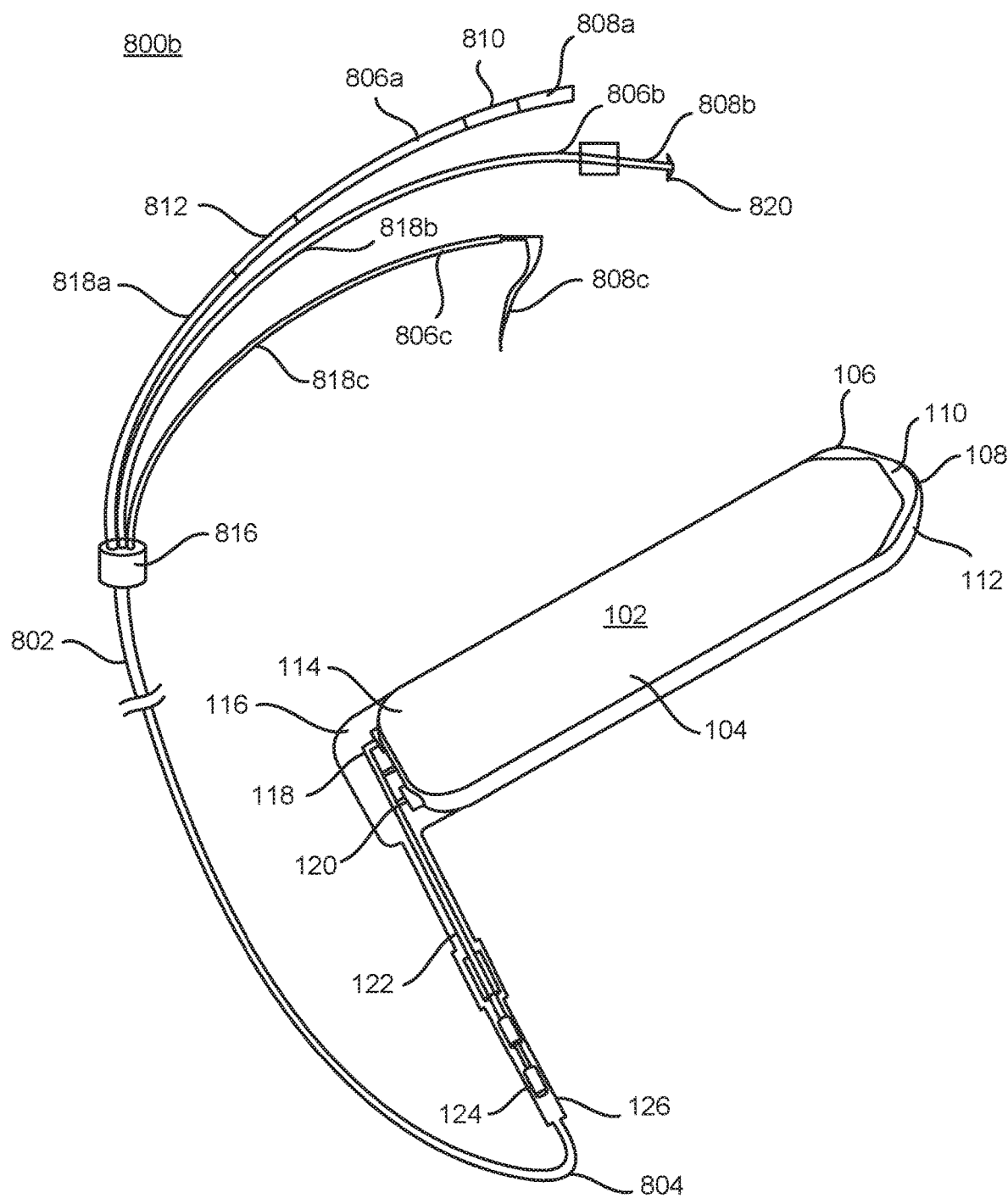
FIG. 8B is an illustration of an exemplary lead having features consistent with the current subject matter.

FIG. 8B is an illustration 800b of an exemplary lead 802 having features consistent with the present disclosure. In some variations, lead 802 can comprise a yoke 816. The yoke can be configured to maintain a hermetically sealed housing for the internal electrical cables of lead 802, while facilitating splitting of the internal electrical cables into separate end-leads 818a, 818b, 818c. Yoke 816 can be disposed toward distal end of lead 802. While three end-leads 818a, 818b, 818c are illustrated in FIG. 8B, the current disclosure contemplates fewer end-leads as well as a greater number of end-leads emanating from yoke 816.

The different end-leads 818a, 818b, 818c, can include different electrodes and/or sensors. For example, end-lead 818b can include an electrode 808b at the distal end 806b of end-lead 818b that differs from electrode 808a at distal end 806a of end-lead 818a. Electrode 808b can have flanges 820. Flanges 820 can be configured to act as an anchor, securing the distal end 806b of end-lead 818b in position within the patient. Electrode 808b with flanges 820 can be suitable for anchoring into high-motion areas of the body where end-lead 818b would otherwise move away from the desired location without the anchoring effect provided by flanges 820. Similarly, electrode 808c at the distal end 806c of end-lead 818c can be configured for a different function compared to the electrodes at the end of other end-leads.

Lead 802 can be a multi-pole lead. Each pole can be electronically isolated from the other poles. The lead 802 can include multiple isolated poles, or electrodes, along its length. The individual poles can be selectively activated. The poles may include sensors for monitoring cardiac or other physiological conditions of the patient, or electrodes for deliver therapy to the patient.

The sensing characteristics of a patient can change over time, or can change based on a patient's posture, a multi-pole lead permits the implantable medical device facilitate monitoring a patient's state through multiple sensing devices, without requiring intervention to reposition a lead. Furthermore, a multi-pole lead can be configured to facilitate supplementary sensing and therapy delivery vectors, such as sensing or stimulating from one pole to a plurality of poles, sensing or stimulating from a plurality of poles to a single pole, or sensing or stimulating between a plurality of poles to a separate plurality of poles. For example, should one particular vector be ineffective at treating a particular arrhythmia, the implantable medical device, or pulse generator, can be configured to switch vectors between the poles on the lead and reattempt therapy delivery using this alternative vector. This vector switching is applicable for sensing. Sensing characteristics can be monitored, and if a sensing vector becomes ineffective at providing adequate sensing signals, the implantable medical device can be configured to switch vectors or use a combination of one or more sensor pairs to create a new sensing signal.

In some variations, at yoke 816, each of the poles of the multi-pole lead can be split into their separate poles. Each of the end-leads emanating from the yoke 816 can be associated with a different pole of the multi-pole lead.

Some of the end-leads emanating from yoke 816 can be configured for providing sensor capabilities of and/or therapeutic capabilities to the patient's heart. Others of the end-leads emanating from yoke 816 can be configured to provide sensor capabilities and/or therapeutic capabilities that are unrelated to the heart. Similarly, the cardiac pacing system herein described can include leads 802, or medical leads, that provide functionality unrelated to the heart.

In some variations, the lead can be bifurcated. A bifurcated lead can comprise two cores within the same lead. In some variations, the different cores of the bifurcated lead can be biased to bend in a predetermined manner and direction upon reaching a cavity. Such a cavity can, for example, be the mediastinum. Bifurcated lead cores can be comprised of shape memory materials, for example, nitinol or other material known in the art to deflect in a predetermined manner upon certain conditions. The conditions under which the bifurcated lead cores will deflect include electrical stimulation, pressure, temperature, or other conditions. In some variations, each core of the bifurcated lead can be configured so that it is steerable by the physician, or an automated system, to facilitate independent advancement of each core of the bifurcated lead, in different directions.

In some variations, sensors from the cardiac pacing system may be selected to optimize sensing characteristics of the cardiac signals. Sensing signals, comprised from one or more sensor pairs may be selected via manual operation of the programming system or automatic operation of the implanted cardiac pacing system. Sensing signals may be evaluated using one of several characteristics including signal amplitude, frequency, width, morphology, signal-to-noise ratio, and the like.

The cardiac pacing system can be configured to use multiple sensors to generate one or more input signals, optionally apply filtering of varying levels to these signals, perform some form of verification of acceptance upon the signals, use the signals to measure levels of intrinsic physiological activity to, subsequently, make therapy delivery decisions. Methods to perform such activities in part or in total include hardware, software, and/or firmware based signal filters, signal amplitude/width analysis, timing analysis, morphology analysis, morphological template comparison, signal-to-noise analysis, impedance analysis, acoustic wave and pressure analysis, or the like. The described analyses may be configured manually via the programming system or via automatic processes contained with the operation software of the cardiac pacing system.

As previously discussed, placing the distal end of the pacing lead in the proper location is important for successful monitoring of a patient's heart and for efficient delivery of therapy. Furthermore, during placement of the lead, a physician must avoid damaging important blood vessels and other anatomical structures of the patient. The provision of a stable platform from which to deliver the leads can reduce the likelihood of collateral damage to anatomical structures of the patient. However, if a delivery platform is remote from the patient, the patient can move relative to the platform. The present disclosure describes a lead delivery system configured for placement on an anatomical structure of the patient, thereby reducing the risk of altering the relative location between the delivery system and the patient during delivery. When the term lead delivery system is used in the present disclosure, it is contemplated that such may also be capable of delivering components other than leads, for example, the lead delivery system may also be utilized in conjunction with delivery assist components. The lead delivery system may also be referred to as a component delivery system.

Figure 17A:
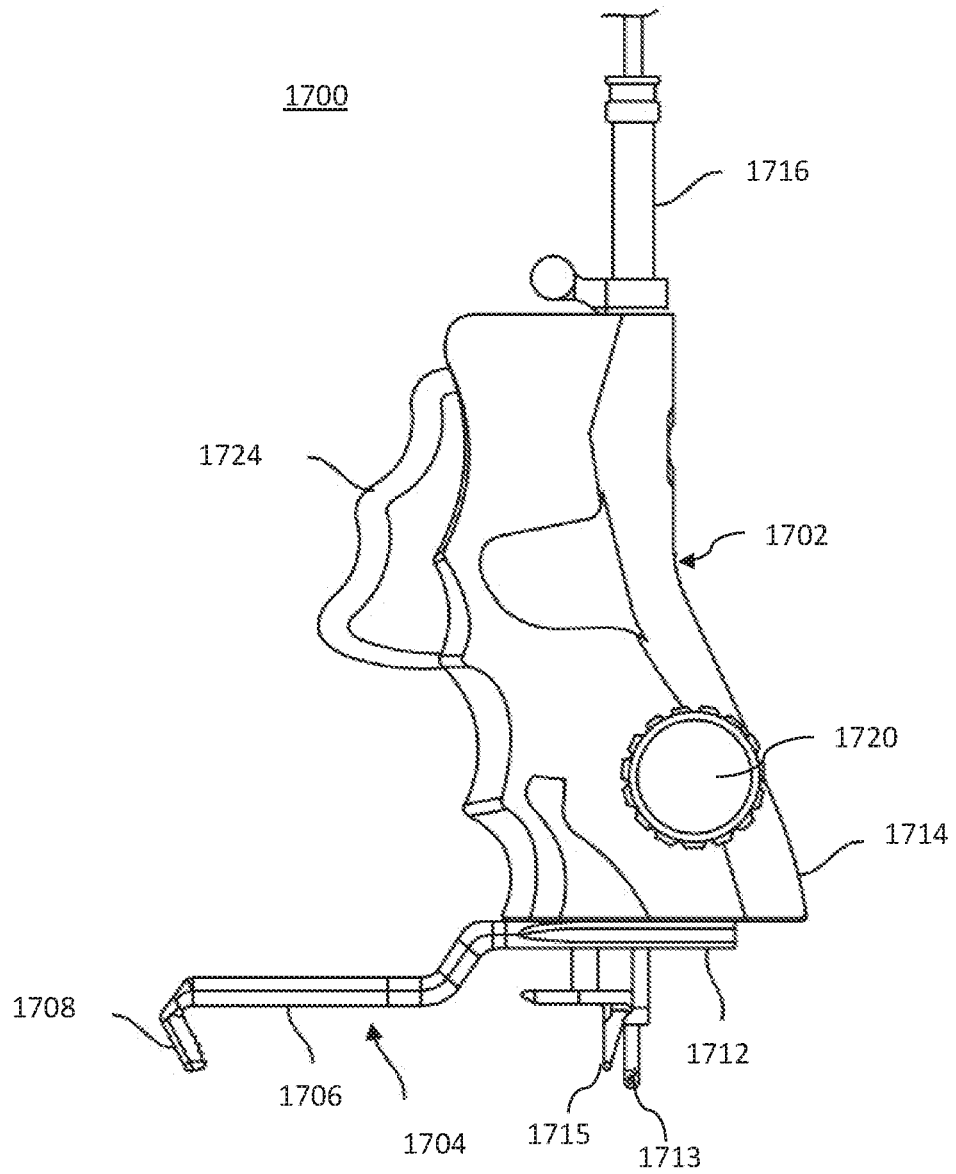
FIG. 17A is an illustration of a side view of an exemplary lead delivery system for facilitating delivery of a lead, the lead delivery system having features consistent with the current subject matter.
Figure 17B:
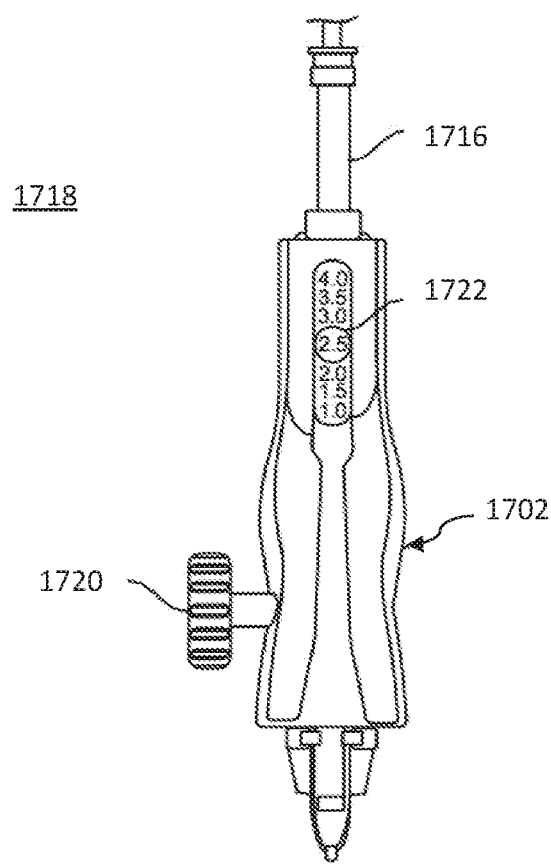
FIG. 17B is an illustration of a front view of the exemplary lead delivery system illustrated in FIG. 17A.
Figure 17C:
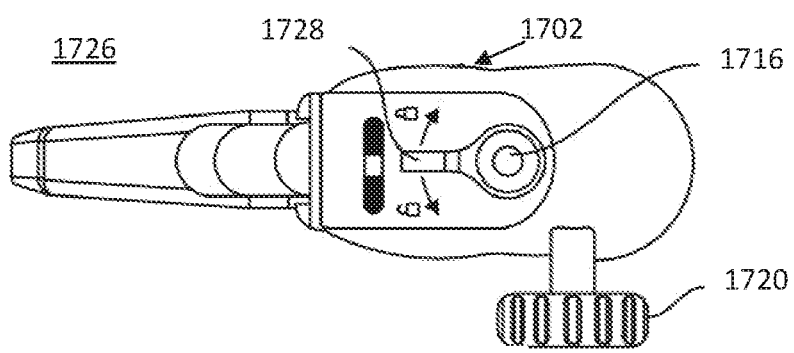
FIG. 17C is an illustration of a top-down view of the exemplary lead delivery system illustrated in FIG. 17.

FIG. 17A is an illustration 1700 of a side view of an exemplary lead delivery system 1702 for facilitating delivery of a lead, having features consistent with the present disclosure. Lead delivery system 1702 can be provided to facilitate placement of one or more leads into the patient. In some variations, lead delivery system 1702 can be configured to facilitate placement of the lead(s) into and/or through an intercostal space of the patient. For example, lead delivery system 1702 can be configured to facilitate placement of the lead(s) into the intercostal spaces of the patient to the right-hand side of the sternum. Alternatively, lead delivery system 1702 can be configured to facilitate placement of the lead(s) into the intercostal spaces of the patient to the left-hand side of the sternum. Optionally, lead delivery system 1702 can be configured to facilitate placement of the lead(s) into the intercostal space of the patient in the region of the cardiac notch and further through to the mediastinum. FIG. 17B is an illustration 1718 of a front view of the exemplary lead delivery system 1702 illustrated in FIG. 17A. FIG. 17C is an illustration 1726 of a top-down view of the exemplary lead delivery system 1702 illustrated in FIG. 17A.

Lead delivery system 1702 can be configured to be affixed to a patient at a desired location such that it remains stationary relative to the patient. Stable fixation to the patient provides an additional benefit where multiple medical instruments are used in concert with lead delivery system 1702. For example, if a device for assisting in lead delivery is first inserted into delivery system 1702 prior to insertion of the lead itself, the physician will have increased confidence that the system did not move between insertion of the two devices. Optionally, lead delivery system 1702 can be handheld and not affixed to the patient.

Lead delivery system 1702 may include base 1712 and lead delivery device 1714. Base 1712 can be configured to secure lead delivery device 1714 to one or more anatomical structures of the patient. In some variations, lead delivery system 1702 can be secured to an anatomical structure of the patient by use of an adhesive. For example, base 1712 can include an adhesive pad. In some variations, an adhesive pad can be reversibly secured to the patient. Proper placement of the adhesive pad to the patient can be accomplished based upon well-known anatomical landmarks, by imaging equipment, or the like.

Lead delivery system 1702 may also be secured to the patient by way of a screw mechanism that securely, but reversibly, affixes lead delivery system 1702 to bone, cartilage or other material within the patient's body.

In some variations, base 1712 of lead delivery system 1702 can include a clamp 1704. Clamp 1704 can be configured to secure base 1712 to the patient. Clamp 1704 can be configured to secure lead delivery device 1714 to one or more anatomical structures of the patient. Clamp 1704 can include a movable clamp platform 1706 and a stationary platform 1715. A hook portion 1708 can be disposed at one end of clamp platform 1706. Hook portion 1708 can be configured to engage with a known anatomical region of the patient. For example, hook portion 1708 can be configured to extend or retract to forcibly engage with the edge of the patient's sternum, while the opposite edge of the patient's sternum engages with stationary platform 1715. At least a portion of clamp platform 1706 may rest on the sternum of the patient. In some variations, the patient's sternum will be exposed, and clamp 1704 can be secured directly to the sternum. In some variations, clamp platform 1706 can include an adhesive portion configured to be disposed between a clamp platform 1706 and the patient to cause clamp platform 1706 to stick to the patient.

In some variations, clamp 1704 can be configured to clamp onto a single rib, multiple ribs, the xyphoid, or other anatomical structures. Clamp 1704 can be engaged around any portion of the chosen anatomical structure. For example, clamp 1704 can be configured to clamp on to the sides of an anatomical structure. In some variations, clamp 1704 can be configured to clamp on the top and bottom of an anatomical structure. In some variations, clamp 1704 can be configured to engage outwardly to secure lead delivery system 1702 between two anatomical structures. When secured to two anatomical structures, lead delivery system 1702 can be secured by expansion forces exerted by clamp 1704 outwardly from clamp platform 1706, against the two anatomical structures. For example, clamp 1704 can be configured to facilitate exerting an outward pressure against two ribs of the patient. The resultant force exerted back against clamp 1704 can keep clamp 1704 in place, relative to the patient.

Clamp 1704 can be tightened when clamp 1704 has been positioned on, around, and/or between the intended anatomical structure(s). In some variations, a screw, an adjustable latch, a ratcheting mechanism, or the like, can be used to adjust clamp 1704. The pressure of clamping clamp 1704 on the anatomical structure may be adjusted with an adjustment handle 1720. Adjustment handle 1720 can also be configured to make adjustments, or refinements, to the location of lead delivery system 1702 as it may become necessary to fine tune the position of lead delivery system 1702 after it has been secured to an anatomical structure of the patient.

As previously noted, it is important to avoid certain critical structures and vessels during lead delivery, such as the heart, lungs, pericardium, internal thoracic artery, and other major vessels of the anterior thoracic region. Exemplary lead delivery system 1702, depicted in FIG. 17, can facilitate the avoidance of critical structures through its locating the lead insertion point proximate the lateral margin of the sternum, especially when system 1702 is clamped to a patient's sternum (utilizing, for example, stationary platform 1715 and retractable hook 1708, as discussed further below). In this implementation, distal end 1713 of cannula 1716 is located proximate stationary platform 1715 and will result in a lead insertion location proximate the lateral margin of the sternum.

Lead delivery devices and systems of the present disclosure are not required to have a clamp 1704, as depicted in FIG. 17, or to necessarily be a fixed to the patient in any way. For example, lead delivery devices and systems similar to those previously described and depicted in FIG. 12 and FIG. 17 (without clamp 1704) may be used without fixation to the patient. Such systems have been described, for example, as facilitating the insertion of lead(s) to the side of the sternum and in the region of the cardiac notch. In one implementation, lead delivery systems 1702 can effect such placement by way of a physician (or other trained healthcare provider) palpating the lateral margin of the sternum, at an intercostal space, prior to making an incision or other method for point of entry (e.g., puncture). Alternatively, lead delivery systems 1702 may be configured to allow for a distal end of the system to be pressed against the sternum of a patient and slid until reaching the lateral margin, then dropping through the intercostal muscles to create a path for lead(s). For example, in one implementation, following the physician identifying an insertion point above a patient's sternum, stationary platform 1715 may be inserted through the incision down to the sternum. The physician may then slide the distal tip of stationary platform 1715 across and against the sternum of the patient until reaching the lateral margin, wherein the pressure applied to the lead delivery device 1714 causes stationary platform 1715 to rest against the sternum, and the distal tip of stationary platform 1715 to insert through the intercostal muscles at the lateral margin of the sternum. The bottoming out of stationary platform 1715 against the sternum prevents over insertion of lead delivery system 1702, and specifically the distal tip of stationary platform 1715. Once positioned, distal end 1713 of cannula 1716 can be inserted to deploy lead(s) as described herein.

In one implementation, such a distal end may be configured to puncture the tissue, for example with a relatively blunt access tip, to facilitate entry into the intercostal space without requiring a surgical incision to penetrate through the intercostal muscles. A blunt access tip, while providing the ability to puncture and push through tissue, does not cut, thereby reducing the potential for damage to the pericardium or other internal organs the tip may contact should such contact occur.

Lead delivery systems configured for lead insertion proximate the lateral margin of the sternum may optionally be designed to effect lead placement to a substernal location. For example, a distal end of the lead delivery system may be shaped or curved, or may be articulable to move after passing the sternum. Alternatively, the lead itself may be articulable in a similar manner.

When lead delivery systems 1702 are configured to be pressed against the sternum of the patient, slid across the sternum until reaching the lateral margin, and then dropped down through the intercostal tissue immediately lateral to the sternal margin, this process may be utilized after a physician has made an incision above the sternum. Such an incision may have been made, for example, to insert a pulse generator, as previously described. In such cases, the lead delivery system may easily traverse the sternum prior to puncturing the intercostal muscles and creating a path to the mediastinum for insertion of lead(s). Proper lead delivery system and lead insertion depth determinations in such cases are facilitated by the fact that sternum and rib cage thicknesses are similar across patient populations. As such, the insertion depth of the lead delivery system may be set at a nominal sternum thickness or slightly less, and thereafter be adjusted deeper to ensure that the lead delivery system does not extend too far within the mediastinum. However, in some cases, lead delivery systems may be utilized in a percutaneous manner, without an incision above the sternum (or without an incision at other entry locations described herein). In these cases, the thickness of a patient's subcutaneous tissue must be accounted for.

Numerous methods for proper lead depth determination have been described herein including systems, methods and software for automating the lead delivery process. These and other implementations may be modified to further account for subcutaneous tissue thickness estimations. In one example, an implanting physician may assess the thickness of subcutaneous tissue based upon specific patient attributes such as height, weight, sex, waist size, chest size, sternum length, etc. These patient attributes may be assessed individually or in combination to predict subcutaneous tissue thickness. Alternatively, direct measurement of the subcutaneous tissue thickness may be made by means such as a needle probe, ultrasound, CT scan, Mill, or the like. Information related to items such as the distance between the posterior surface of the sternum and the pericardium, the distance between the sternal margin to the thoracic vein or artery, and sternum thickness may then be used by the physician, or by an automated delivery system, to adjust the intended lead implantation location, orientation and depth.

With further reference to FIG. 17, exemplary lead delivery system 1702 can include a lead delivery device 1714 configured to facilitate delivery of a lead into the patient to a desired location. Lead delivery device 1714 can include a lead advancer, which can be configured to incrementally advance a lead into a patient. The lead may be advanced into a patient by a predefined amount. The lead advancer can be configured to facilitate the delivery of leads to the correct position, orientation and depth within the patient.

Leads delivered by lead delivery system 1702 may be leads configured to deliver therapeutic electrical pacing to the heart of the patient. Leads delivered by lead delivery system 1702 can also be leads configured to obtain physiological information about the patient, such as heart function, lung function, the performance of various blood vessels, and the like.

Lead delivery device 1714 can be configured to advance a lead through an intercostal space of the patient and, optionally, into the mediastinum of the patient. Lead delivery device 1714 can be configured to position the distal end of the lead at any of the positions described in the present disclosure. Lead delivery device 1714 can also be configured to control an angle at which a lead is inserted into the patient.

Lead delivery system 1702 can include a cannula 1716, which may extend through the length of lead delivery device 1714. Cannula 1716 can also extend through the lead advancer. Cannula 1716 can be configured to receive a lead for insertion and may be configured to accompany a lead as it is inserted into the patient. In some variations, cannula 1716 can be configured to receive delivery assist components (discussed below) for insertion into the patient. In some variations, lead delivery system 1702 can include multiple cannulas for simultaneous delivery of leads and/or delivery assist components into the patient.

In some variations, a screw, an adjustable latch, a ratcheting mechanism, or the like, can be used to adjust the distance between the distal end 1713 of cannula 1716 and stationary platform 1715. Such adjustments or refinements may become necessary to fine tune the position of lead delivery system 1702 and the location of the distal end 1713 of cannula 1716 after it has been secured to an anatomical structure of the patient In some instances, a smaller cannula opening may ease the insertion through tissue. As such, in additional variations, the size of the cannula opening may be variably controlled by the operator. The cannula may, for example, be comprised of two cannula halves, or multiple cannula segments, that expand or separate to a desired opening size. The variably selected cannula opening size may be controlled via screw, an adjustable latch, a ratcheting mechanism, lever, or the like, in order to facilitate delivery of a variety of lead shapes and sizes.

Lead delivery system 1702 may utilize delivery assist component(s) such as a needle, a guide wire, guide catheter, sheath, expandable catheter, balloon catheter and the like. A delivery assist component can be configured to facilitate delivery of a lead into the patient. Delivery assist components may be configured to be inserted into a patient and advanced to the desired location prior to lead insertion. Alternatively, a delivery assist component can be configured to be inserted into the patient with a lead and advanced with the lead to the desired location. The delivery assist component can be used to create space and minimize damage to surrounding tissue prior to, or in connection with, the deployment of a lead into the patient. The delivery assist component can be removed from the patient once the lead has been placed at the desired location. Delivery assist components can be inserted into the patient by the lead delivery system 1702 in much the same way as a lead. Delivery assist components may incorporate sensors. Such sensors can include the sensor types described in the present disclosure for use on leads to monitor the location of leads with respect to patient anatomy. It is understood that delivery assist components may interact with lead delivery system 1702 in much the same way as leads themselves, as described herein.

Careful advancement of the component into the patient is desirable. Lead delivery system 1702 can include a lead advancer, which can be configured to incrementally advance a lead into a patient in response to an interaction by an operator. Limiting movement of the lead advancing into the body can avoid accidental perforation and damage to anatomical structures. In some variations, lead delivery system 1702 can include a trigger 1724, which can be configured to activate a ratcheting mechanism to advance the lead. One pull on trigger 1724 connected to the ratcheting mechanism can cause the lead to be advanced a known, prescribed, amount. For example, the amount can be set to 1 mm, 2 mm, or the like. In some variations, this length can be set or programmed by the physician. In some variations, a partial pull on trigger 1724 can result in a partial advancement of the lead by a partial amount of the set amount. For example, where depressing the trigger fully can result in an advancement of 1 mm and therefore a partial depression of the trigger can be set to cause the result of an advancement of 0.5 mm. The lead delivery system 1702 can include a limit on the number of trigger 1724 pulls permitted within an interval. For example, the lead delivery system 1702 may restrict the physician from pulling trigger 1724 more than one time per second. In another option, the lead delivery system 1702 may require the physician to actively set a trigger limit in order to permit trigger 1724 pulls in excess of the permitted interval.

Lead delivery system 1702 can include a locking mechanism activated by a locking switch 1728 that can reversibly lock a lead with respect to the lead delivery system 1702. When locked, the lead being delivered to the patient can be engaged with delivery system 1702 such that it cannot be moved independent of movement from, say, the ratcheting system. When unlocked, the lead can move freely within cannula 1716 of lead delivery system 1702. Lead delivery system 1702 can be further configured to only permit movement of the lead in one direction when locking switch 1728 is in the unlocked position.

Where a delivery assist component is used and unlocked from lead delivery system 1702, the physician can remove the delivery assist component, such as a needle, from cannula 1716. The physician may then insert another delivery assist component, or a lead, into cannula 1716 of lead delivery system 1702. The physician can lock the lead, or the new delivery assist component, for example, into the ratcheting mechanism of lead delivery system 1702. The physician, or an automated system, can then advance the lead within the patient to a depth indicated by the previous component's readout. In some variations, the physician can use the previous depth readout with sensors or physical markers on the lead to ensure proper placement of the lead.

While the lead is being inserted into the patient to the desired location, the movement of the lead can be metered. Transverse movement of the lead can be metered as well the depth of the lead into the patient. Metering the movement of the lead can avoid excessive movement of the lead. In some variations, movement can be metered by a ratcheting mechanism and the magnitude of the movement of the lead can be presented to the operator. For example, a reading indicating the amount of movement can be presented to the operator, such as through reading window 1722.

In some variations, lead delivery system 1702 can be configured to coordinate with real-time imaging equipment to assess the relative location of the lead being delivered by lead delivery system 1702.

Sensor(s) associated with lead delivery system 1702 can facilitate delivery. Sensor(s) can be disposed on the lead delivery device 1714, remote from the lead delivery device 1714, such as on a gurney, or in an operating room, on the lead itself, or in other locations.

Sensor(s) may be utilized to help determine an appropriate insertion point for the lead by, for example, identifying blood-filled vessels such as arteries and veins below the surface of the skin. An example of such identification of subcutaneous vessels is described in relation to FIGS. 9A and 9B. Similarly, sensors can be used to identify the location of ribs, or other anatomy. The use of sensors of the types identified herein facilitate determination of an appropriate insertion point that will avoid damage to critical anatomy.

Sensor(s) can also utilized to determine a proper depth in the patient for the distal end of the lead, or proper positioning with respect to specific anatomy. As previously described, different tissues within the patient's body can demonstrate varying characteristics. The differing physiological characteristics of the tissues of the body can facilitate placement of the delivery system and/or lead at the desired location. Lead delivery system 1702 can be configured to monitor the physiological characteristics of the tissues surrounding the distal end, or advancing end, of the lead and/or delivery assist component being delivered to the desired position. Physiological sensors, such as pressure sensors, impedance sensors, accelerometers, pH sensors, temperature sensors, and the like, can monitor the characteristics of the anatomy at the end of the implanted, or advancing, lead or device. Lead delivery system 1702 can be configured to determine the location of the lead being implanted based on the detected physiological characteristics as has been described with reference to FIGS. 10-13 and at other locations within the present disclosure.

Lead delivery system 1702 can be configured to provide real-time feedback to an implanting physician based on readings from the above-mentioned sensors. Feedback can be provided with indicators, alarms or the like.

Figure 18:
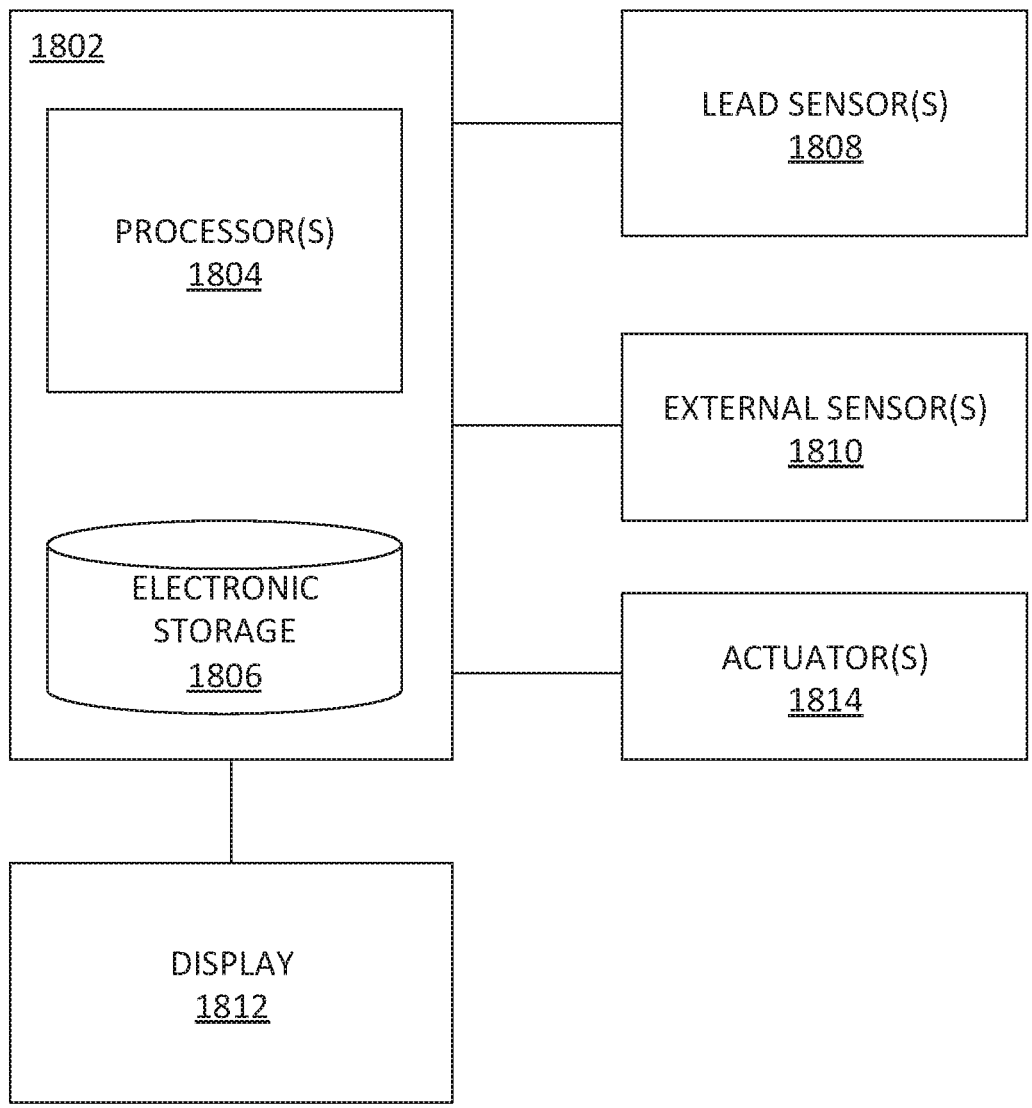
FIG. 18 is an illustration of a schematic diagram showing components of an exemplary lead delivery system having features consistent with the current subject matter.

Lead delivery system 1702 can be automated. Automating the lead delivery system can allow a physician to set up the system and then rely on sensors and computer control of lead delivery system 1702 to deliver the lead to the desired location. In some variations, the lead delivery system 1702 can be semi-automatic, where measurements and advancements made by lead delivery system 1702 occur automatically, but only after the physician reviews certain measurements or replies to prompts provided by lead delivery system 1702. FIG. 18 is an illustration of a schematic diagram 1800 showing components of lead delivery system 1702 having features consistent with the current subject matter. Lead delivery system 1702 can include, or be associated with, a computing device 1802 that can be configured to control the operation of delivery system 1702. Computing device 1802 can include processor(s) 1804 configured to cause computing device 1802 to transmit signals to the various elements of the lead delivery system 1702 and/or other devices to control lead delivery system 1702. Computing device 1802 can also be configured to control other devices in concert with lead delivery system 1702.

Computing device 1802 can include electronic storage 1806 to store computer-readable instructions for execution by processor(s) 1804. The computer-readable instructions can cause processor(s) 1804 to perform functions consistent with the present disclosure. The functions that can be performed include the functions described herein attributable to a physician.

Sensors disposed on an advancing lead, a delivery assist component, or the lead delivery system 1702 (all referred to as component sensors 1808 in FIG. 18), can be used to facilitate the identification of an insertion point, and the delivery of a lead, as discussed herein. External sensor machinery 1810 such as x-ray machines, fluoroscopy machines, ultrasound machines, and the like, can also be used to assist in the lead delivery process.

Computing device 1802 can be in communication with one or more component sensors 1808 and/or external sensors 1810. Computing device 1802 may communicate with such sensors through wired or wireless communication systems. As described throughout the present disclosure, such sensors can be used by computing device 1802 to determine an insertion point that is optimally placed with respect to anatomy such as the sternum, ribs, or critical arteries. The sensors can also be used by computing device 1802 to determine a safe path of advancement and fixation for a lead, which will avoid damage to critical structures and provide optimal distal end placement for effective pacing and sensing. Optimal placement effected by an automated delivery system 1702, in conjunction with computing device 1802 can result in the distal end of a lead being placed in any of the locations described within the present disclosure (for example, intercostally into the mediastinum, or to just beyond the innermost intercostal muscle, etc.).

Computing device 1802 can be further configured to control one or more actuators 1814 disposed on a lead delivery system 1702. The lead delivery system can comprise motors configured to advance or retract a delivery assist component and/or lead, or to effect lateral movements, or to change the angle of advancement or retraction of the lead.

Computing device 1802 and automated lead delivery system can be further configured to present information via indicators, alarms or on a screen associated with the placement of a lead and/or delivery assist component. Computing device 1802 can be in electronic communication with a display 1812. Computing device 1812 can be configured to cause a presentation on display 1812 of information associated with the advancing lead. For example, measurements obtained by sensor(s) 1808 and/or 1810 can be processed by processor(s) 1804 to provide images or representations of anatomy in the vicinity of an advancing lead. Computing device 1802 can be configured to cause presentation of warnings on display 1812. For example, computing device 1802 can be configured to cause an indication to be presented on display 1812 that the end of the lead has reached the desired location within the patient. Display 1812 can display an indication of damage to tissues caused by an advancing lead. Display 1812 can display an indication of future potential damage of tissues allowing the operator to stop the procedure or determine solutions to circumvent problems. In some variations, processor(s) 1804 can be configured to determine solutions to circumvent problems and cause the solutions to be presented on the display 1812.

While components have been described herein in their individual capacities, it will be readily appreciated the functionality of individually described components can be attributed to one or more other components or can be split into separate components. This disclosure is not intended to be limiting to the exact variations described herein, but is intended to encompass all implementations of the presently described subject matter.

In the descriptions above, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results.

We claim:

1. A lead for implantation in a patient, the lead comprising:
   a directional electrode configured for implantation on or near the inner surface of a rib or the inner surface of the innermost intercostal muscle and not physically in contact with the heart or the pericardium of the heart, the directional electrode having an electrically active portion configured to emanate stimulating energy from an exposed portion of the directional electrode toward the pericardium and the heart; and
   an electrically insulating portion around at least part of a circumference of the lead, the electrically insulating portion configured to insulate surrounding muscle and/or tissue from the stimulating energy when the lead is implanted in the patient.

2. The lead of claim 1, wherein the electrically insulating portion surrounds the entire circumference of the lead but leaves exposed a distal tip of the lead so that the directional electrode is at the distal tip of the lead.

3. The lead of claim 1, wherein the directional electrode is electrically insulated on all sides other than one exposed side.

4. The lead of claim 1, wherein the directional electrode is located away from a distal tip of the lead.

5. The lead of claim 4, wherein the directional electrode is electrically insulated over a significant portion of the lead's circumference.

6. The lead of claim 4, wherein, at the location of the directional electrode, approximately 50% of the circumference of the lead is electrically insulating, leaving approximately 50% of the circumference of the lead exposed.

7. The lead of claim 4, wherein, at the location of the directional electrode, approximately 75% of the circumference of the lead is electrically insulating, leaving approximately 25% of the circumference of the lead exposed.

8. A method of implanting a lead in a patient, the lead having a directional electrode and an electrically insulating portion around at least part of a circumference of the lead, the directional electrode having an electrically active portion configured to emanate stimulating energy from an exposed portion of the directional electrode, the method comprising:
   placing the lead in the patient such that the electrically insulating portion of the lead is on or near an inner surface of a rib or an inner surface of the innermost intercostal muscle of the patient and not physically in contact with the heart or the pericardium of the heart where the electrically insulating portion insulates the intercostal muscle from the stimulating energy; and
   directing the directional electrode of the lead toward a heart of the patient.

9. The method of claim 8, wherein placing the lead in the patient further comprises implanting the lead through an intercostal space of the patient in a region of a cardiac notch.

10. The method of claim 8, wherein the placing of the lead results in the electrically insulating portion touching the intercostal muscle.

11. The method of claim 8, wherein placing the lead further includes the lead being proximate the heart, but not being physically in contact with the heart or a pericardium of the heart.

12. A cardiac pacing system comprising:
    a lead implanted in a patient through an intercostal space and on or near an inner surface of a rib or an inner surface of an innermost intercostal muscle in a region of a cardiac notch of the patient and not physically in contact with the heart or the pericardium of the heart, the lead comprising:
      a directional electrode having an electrically active portion configured to emanate stimulating energy from an exposed portion of the directional electrode toward the pericardium and the heart; and
      an electrically insulating portion around at least part of a circumference of the lead, the lead implanted such that the electrically insulating portion insulates surrounding muscle and/or tissue from the stimulating energy.

13. The cardiac pacing system of claim 12, wherein the electrically insulating portion surrounds the entire circumference of the lead but leaves exposed a distal tip of the lead so that the directional electrode is at the distal tip of the lead.

14. The cardiac pacing system of claim 12, wherein the directional electrode is electrically insulated on all sides other than one exposed side.

15. The cardiac pacing system of claim 12, wherein the directional electrode is located away from a distal tip of the lead.

16. The cardiac pacing system of claim 15, wherein the directional electrode is electrically insulated over a significant portion of the lead's circumference.

17. The cardiac pacing system of claim 15, wherein, at the location of the directional electrode, approximately 50% of the circumference of the lead is electrically insulating, leaving approximately 50% of the circumference of the lead exposed.

18. The cardiac pacing system of claim 15, wherein, at the location of the directional electrode, approximately 75% of the circumference of the lead is electrically insulating, leaving approximately 25% of the circumference of the lead exposed.

* * * * *